(12) United States Patent
Allison et al.

(10) Patent No.: US 7,304,051 B2
(45) Date of Patent: Dec. 4, 2007

(54) QUINOXALINE COMPOUNDS

(75) Inventors: Brett D. Allison, Del Mar, CA (US); Michael D. Hack, San Diego, CA (US); Victor K. Phuong, San Diego, CA (US); Michael H. Rabinowitz, San Diego, CA (US); Mark D. Rosen, San Diego, CA (US)

(73) Assignee: Janssen Pharmaceutica N.V. (BE)

( * ) Notice: Subject to any disclaimer, the term of this patent is extended or adjusted under 35 U.S.C. 154(b) by 294 days.

(21) Appl. No.: 10/910,925

(22) Filed: Aug. 4, 2004

(65) Prior Publication Data

US 2005/0038032 A1 Feb. 17, 2005

Related U.S. Application Data

(60) Provisional application No. 60/494,074, filed on Aug. 8, 2003.

(51) Int. Cl.
- A01N 43/00 (2006.01)
- A01N 43/46 (2006.01)
- A61K 31/55 (2006.01)

(52) U.S. Cl. ............ 514/215; 514/217.05; 514/217.07; 514/234.8; 514/249; 540/546; 540/593; 540/599; 544/119; 544/353

(58) Field of Classification Search ...................... None
See application file for complete search history.

(56) References Cited

U.S. PATENT DOCUMENTS

| | | | |
|---|---|---|---|
| 5,847,125 A | 12/1998 | McDonald | |
| 6,239,131 B1 | 5/2001 | Shinozaki et al. | |
| 2004/0235849 A1* | 11/2004 | Beyreuther et al. | 514/249 |
| 2006/0069286 A1* | 3/2006 | Allison et al. | 564/80 |

FOREIGN PATENT DOCUMENTS

| | | |
|---|---|---|
| WO | WO 95/04720 | 2/1995 |
| WO | WO 02087568 A1 | 11/2002 |
| WO | WO 02088073 A1 | 11/2002 |
| WO | WO 02100825 A2 | 12/2002 |
| WO | WO 04/13087 | 2/2004 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Hawley's Condensed Chemical Dictionary, 13th ed., Richard J. Lewis, Sr., © 1997 by Van Nostrand Reinhold. p. 587.*
Swift and Smith "Cholecystokinin Analog, JMV-180, Stimulates Growth of Pancreatic Cancer" Digestive Diseases and Sciences, vol. 39(5), pp. 1007-1013 (May 1994).*
Malecka-Panas "The Role of Gastrin in Colorectal Carcinogenesis" International Review of Allergology & Clinical Immunology, vol. 6(4), pp. 151-156 (2000). ABSTRACT.*
Konturek et al, "H. Pylori, Atrophic Gastritis, Cytokines, Gastrin, COX-2, PPAR Gamma and Impaired Apoptosis in Gastric Carcinogenesis" Medical Science Monitor, vol. 9(7), pp. SR53-SR66 (Jul. 2003). ABSTRACT.*
Haigh et al, "Gastrin Induces Proliferation in Barrett's Metaplasia Through Activation of the CCK2 Receptor" Gastroenterology, vol. 124, pp. 615-625 (Mar. 2003).*
Lehy et al, "Histomorphological Characteristics of Gastric Mucosa in Patients with Zollinger-Ellison Syndrome or Autoimmune Gastric Atrophy: Role of Gastrin and Atrophying Gastritis" Microscopy Research Tech., vol. 48(6), pp. 327-338 (Mar. 29, 2000). ABSTRACT.*
Tonini et al, "Novel Therapeutic Strategies in Acid-Related Disorders," Expert Opinion on Therapeutic Patents, vol. 13(5), pp. 639-649 (2003). ABSTRACT.*
Lewin et al, "Primary Gastrin Cell Hyperplasia. Report of Five Cases and a Review of the Literature" American Journal of Surgical Pathology, vol. 8(11), pp. 821-832 (Nov. 1984).*
Romanenko et al, "Condensed and Bonded Quinoxalines IV. New Path to Arylamides (1,2-Dihydro—2-hydroxyquinoxalyl-3) Acetic Acid" Khimiya Geterotsiklicheskikh Soyedineniy, vol. 2, pp. 264-266 (1973) ENGLISH TRANSLATION.*
Cameroni et al, "Structure of Various Nitro Derivatives of 7-Chloro-1,2,4-benzothiadiazine-1,1-dioxide" Gazzetta Chimica Italiana, vol. 96(4), pp. 349-358 (1966). As Abstracted by CAS Online (STN).*
Black, J.W. and S.B. Kalindjian. Gastrin Agonists and Antagonists. Pharmacol. Toxicol. 2002, 91:275-281.
de Tullio, P. et al. Therapeutic and Chemical Developments of Cholecystokinin Receptor Ligands. Exp. Opin. Invest. Drugs 2000, 9(1):129-146.
Herranz, R. Cholecystokinin Antagonists: Pharmacological and Therapeutic Potential. Med. Res. Rev. 2003, 23(5):559-605.
McDonald, I.M. CCK2 Receptor Antagonists. Exp. Opin. Ther. Patents. 2001, 11(3):445-462.

(Continued)

*Primary Examiner*—Zachary C Tucker

(57) ABSTRACT

Amidophenyl-sulfonylamino-quinoxaline compounds of formula (I)

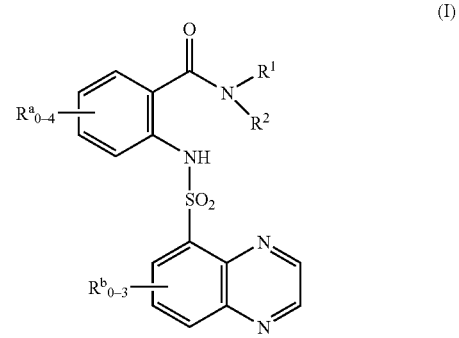

are CCK2 modulators useful in the treatment of CCK2 mediated diseases.

36 Claims, No Drawings

OTHER PUBLICATIONS

Morton, M.F. et al. Pharmacological Comparison of the Alternatively Spliced Short and Long CCK2 Receptors. Br. J. Pharmacol. 2003, 140(1):218-224.

Revel, L. and F. Makovec. Update on Nonpeptide CCK-B Receptor Antagonists. Drugs Future. 1998, 23(7):751-766.

Tracy, H.J. and R.A. Gregory. Physiological Properties of a Series of Peptides Structurally Related to Gastrin 1. Nature (London) 1964, 204:935-938.

Varnavas, A. et al. Anthranilic Acid Based CCK1 Antagonists: The 2-Indole Moiety May Represent a "Needle" According to the Recent Homonymous Concept. Eur. J. Med. Chem. 2004, 39:85-97.

Varnavas, A. et al. Anthranilic Acid Derivatives: A New Class of Non-Peptide CCK1 Receptor Antagonists. Bioorg. Med. Chem. 2003, 11:741-751.

Varnavas, A. et al. Synthesis of N-Terminal Substituted Anthranilic Acid Dimer Derivatives for Evaluation on CCK Receptors. Il Farmaco. 2001, 56:555-564.

PCT International Search Report, dated Dec. 14, 2004, for PCT Int'l. Appln. No. PCT/US2004/025153.

Varnavas, A. et al., "Synthesis of new anthranilic acid dimer derivatives and their evaluation on CCK receptors", Il Farmaco, Rome Italy, vol. 55, No. 5, 2000, pp. 369-375.

\* cited by examiner

QUINOXALINE COMPOUNDS

This application claims priority to provisional application, which is U.S. Ser. No. 60/494,074, filed Aug. 8, 2003. The complete disclosures of the aforementioned related U.S. patent applications are hereby incorporated herein by reference for all purposes.

FIELD OF THE INVENTION

There is provided by the present invention compounds that are CCK2 receptor modulators. More particularly, there is provided by the present invention quinoxalines that are CCK2 receptor modulators useful for the treatment of disease states mediated by CCK2 receptor activity.

BACKGROUND OF THE INVENTION

This invention relates to gastrin and cholecystokinin (CCK) receptor ligands. The invention also relates to methods for preparing such ligands and to compounds that are useful intermediates in such methods. The invention further relates to pharmaceutical compositions comprising such ligands and methods for preparing such pharmaceutical compositions.

The gastrins and cholecystokinins are structurally related neuropeptides that exist in gastrointestinal tissue, gastrinomas and, in the case of the cholecystokinins, the central nervous system (J. H. Walsh, Gastrointestinal Hormones, L. R. Johnson, ed., Raven Press, New York, 1994, p. 1).

Several forms of gastrin are found including 34-, 17- and 14-amino acid species with the minimum active fragment being the C-terminal tetrapeptide (TrpMetAspPhe-NH2), which is reported in the literature to have full pharmacological activity (H. J. Tracy and R. A. Gregory, Nature (London), 1964, 204:935-938). Much effort has been devoted to the synthesis of analogs of this tetrapeptide (and the N-protected derivative Boc-TrpMetAspPhe-NH2) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33. A review of CCK receptors, ligands and the activities thereof may be found in P. de Tullio et al. (Exp. Opin. Invest. Drugs, 2000, 9(1):129-146).

Gastrin and cholecystokinin are key regulators of gastrointestinal function. In addition, cholecystokinin is a neurotransmitter in the brain. Gastrin is one of the three primary stimulants of gastric acid secretion. In addition to the acute stimulation of gastric acid, gastrin has a trophic effect on the gastrointestinal mucosa and is implicated as a trophic hormone of several adenocarcinomas, including pancreatic, colorectal, esophageal and small cell lung.

Cholecystokinin stimulates intestinal motility, gallbladder contraction, and pancreatic enzyme secretion, and is known to have trophic actions on the pancreas thus increasing, inter alia, pancreatic enzyme production. Cholecystokinin also inhibits gastric emptying and has various effects in the central nervous system, including regulation of appetite and pain.

Gastrin acts on CCK2 (otherwise known as gastrin/CCK-B receptors) whereas cholecystokinin acts on both CCK2 and CCK1 receptors (otherwise known as cholecystokinin/CCK-A receptors). Compounds that bind to cholecystokinin and/or gastrin receptors are important because of their potential pharmaceutical use as antagonists of the natural peptides or mimetics of the natural peptides acting as partial or full agonists at the cholecystokinin and/or gastrin receptors. A selective gastrin receptor antagonist has not yet been marketed. However, several are currently undergoing clinical evaluation. JB95008 (gastrazole) is being developed by The James Black Foundation and Johnson & Johnson Pharmaceutical Research & Development LLC for the potential treatment of advanced pancreatic cancer (pancreatic adenocarcinoma), and is currently in Phase II clinical trials. ML Laboratories and Panos are developing L-365,260 (Colycade), which is in Phase II clinical trials for pain. Other potential indications included eating disorders and cancer. YF-476 (formerly YM-220), under joint development by Yamanouchi and Ferring Research Institute, is in Phase I clinical trials for gastro-esophageal reflux disease (GERD). In Phase I trials, Zeria Pharmaceutical is investigating Z-360, an orally available 1,5-benzodiazepine derivative (WO-09825911), as a potential treatment for gastroduodenal ulcers and reflux esophagitis. CR 2945 (itriglumide), an orally active anthranilic acid derivative, has been investigated by Rotta in Phase I trials for anxiety disorders, cancer (particularly colon cancer) and peptic ulcer.

Gastrimmune, Aphton Corporation's anti-gastrin vaccine, which works by chemical neutralization of the hormone, is undergoing late stage clinical trials for cancer indications, in particular, pancreatic and gastric tumors.

In addition to those indications described above, gastrin (CCK2) antagonists have been proposed for the following gastrin-related disorders: gastrointestinal ulcers, Barrett's esophagus, antral G cell hyperplasia, pernicious anaemia, Zollinger-Ellison syndrome, and other conditions in which lower gastrin activity or lower acid secretion is desirable.

Cholecystokinin (CCK1) receptors have been shown to mediate cholecystokinin-stimulated gallbladder contraction, pancreatic enzyme secretion, satiety, gastric emptying inhibition and regulation of peristalsis, indicating a key role in the integrated physiological gastrointestinal response to a meal. In addition, there is evidence that cholecystokinin receptors mediate a mitogenic action of cholecystokinin on some adenocarcinomas. Consequently, selective cholecystokinin receptor antagonists, for example, devazepide (Merck), lorglumide (Rotta), 2-NAP (JBF), dexloxiglumide (Rotta), and lintitript (Sanofi) have been examined in the clinic for potential applications in, inter alia, irritable bowel syndrome, chronic constipation, non-ulcer dyspepsia, acute and chronic pancreatitis, biliary disease and pancreatic cancer. Additional roles of cholecystokinin receptors include the regulation of appetite and metabolism, indicating potential therapeutic applications in the treatment of disorders such as obesity and anorexia nervosa. Other possible uses are in the potentiation of opiate (for example morphine) analgesia and in the treatment of cancers, especially of the pancreas. Moreover, ligands for cholecystokinin/gastrin receptors in the brain have been claimed to possess anxiolytic activity, and gastrin receptor antagonists would be expected to act as neurological agents towards the relief of anxiety and related neuroses and psychoses.

SUMMARY OF THE INVENTION

The invention features a quinoxaline sulfonamide compound of formula (I):

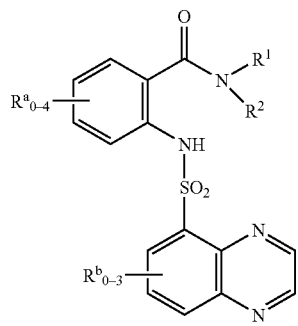

(I)

wherein $R^1$ and $R^2$ are each independently selected from the group consisting of a) H, $C_{1-7}$alkyl, $C_{2-7}$alkenyl, $C_{2-7}$alkynyl, $C_{3-7}$cycloalkyl, $C_{3-7}$cycloalkenyl, benzo-fused$C_{4-7}$cycloalkyl where the point of attachment is a carbon atom adjacent to the ring junction, $C_{3-7}$cycloalkyl$C_{1-7}$alkyl, b) naphthyl-$(CR^s{}_2)$—, benzoyl$C_{0-3}$alkyl-$(CR^s{}_2)$—, phenyl, said phenyl optionally fused at two adjacent carbon atoms to $R^f$, phenyl-$(CR^s{}_2)$—, said phenyl optionally fused at two adjacent carbon atoms to $R^f$, $R^f$ is a linear 3- to 5-membered hydrocarbon moiety having 0 or 1 unsaturated bonds and having 0, 1 or 2 carbon members which is a carbonyl, c) $Ar^6$—$(CR^s{}_2)$—, where $Ar^6$ is a 6-membered heteroaryl having carbon as a point of attachment, having 1 or 2 heteroatom members which are —N= and optionally benzo fused, d) $Ar^5$—$(CR^s{}_2)$—, where $Ar^5$ is a 5-membered heteroaryl having carbon as a point of attachment, having 1 heteroatom member selected from the group consisting of O, S, >NH or >N$C_{1-4}$alkyl, having 0 or 1 additional heteroatom member which is —N= and optionally benzofused, e) $Ar^{6-6}$—$(CR^s{}_2)$—, where $Ar^{6-6}$ is phenyl having the point of attachment and fused to a 6-membered heteroaryl having 1 or 2 heteroatom members which are —N=, f) $Ar^{6-5}$—$(CR^s{}_2)$—, where $Ar^{6-5}$ is phenyl having the point of attachment and fused to a 5-membered heteroaryl having 1 heteroatom member selected from the group consisting of O, S, >NH or >N$C_{1-4}$alkyl and having 0 or 1 additional heteroatom member which is —N=, g) $C_{1-4}$alkylO- and HS$C_{1-4}$alkyl, where $R^1$ and $R^2$ are not simultaneously H and, except in positions where $R^s$ is indicated, each of a) to g) is substituted with 0, 1, 2, or 3 of $R^q$, $R^q$ is independently selected from the group consisting of $C_{1-4}$alkyl, hydroxy, fluoro, chloro, bromo, iodo, trifluoromethyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy and $C_{1-4}$alkylS-, $R^s$ is independently selected from the group consisting of H, $C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, HS—$C_{1-4}$alkyl, $C_{1-4}$alkylO—$C_{1-4}$alkyl, $C_{1-4}$alkylS-$C_{1-4}$alkyl and phenyl;

or, alternatively, $R^1$ and $R^2$ may be taken together with the nitrogen to which they are attached and are selected from the group consisting of i) 10-oxa-4-aza-tricyclo[5.2.1.0$^{2,6}$]dec-4-yl, optionally mono- or di-substituted with $R^p$, $R^p$ is independently selected from the group consisting of hydroxy, $C_{1-4}$alkyl, hydroxy$C_{1-4}$alkyl, phenyl, mono-, di- or tri-halo substituted phenyl and hydroxyphenyl, ii) a 4-7 membered heterocyclic ring said heterocyclic ring having 0 or 1 additional heteroatom members separated from the nitrogen of attachment by at least one carbon member and selected from O, S, —N=, >NH or >NR$^p$, having 0, 1 or 2 unsaturated bonds, having 0, 1 or 2 carbon members which is a carbonyl, optionally having one carbon member which forms a bridge and having 0, 1 or 2 substituents $R^p$, iii) a benzo fused 4-7 membered heterocyclic ring said heterocyclic ring having 0 or 1 additional heteroatom members separated from the nitrogen of attachment by at least one carbon member and selected from O, S, —N=, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents $R^p$, iv) a 4-7 membered heterocyclic ring said heterocyclic ring having 0 or 1 additional heteroatom members separated from the nitrogen of attachment by at least one carbon member and selected from O, S, —N=, >NH or >NR$^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N=, >NH or >NR$^p$, having 0, 1 or 2 unsaturated bonds, having 0, 1 or 2 carbon members which is a carbonyl and having 0, 1 or 2 substituents $R^p$;

v) 8-oxo-1,5,6,8-tetrahydro-2H,4H-1,5-methano-pyrido[1,2-a][1,5]diazocin-3-yl, optionally having 0, 1 or 2 substituents $R^p$;

$R^a$ is independently selected from the group consisting of $C_{1-6}$alkyl, $C_{2-6}$alkenyl, $C_{3-6}$cycloalkyl, phenyl, furanyl, thienyl, benzyl, pyrrol-1-yl, —OH, —O$C_{1-6}$alkyl, —O$C_{3-6}$cycloalkyl, -Ophenyl, -Obenzyl, —SH, —S$C_{1-6}$alkyl, —S$C_{3-6}$cycloalkyl, -Sphenyl, -Sbenzyl, —CN, —NO$_2$, —N(R$^y$)R$^z$ (wherein R$^y$ and R$^z$ are independently selected from H, $C_{1-4}$alkyl or $C_{1-6}$cycloalkyl$C_{1-4}$alkyl), —(C=O)$C_{1-4}$alkyl, —SCF$_3$, halo, —CF$_3$, —OCF$_3$, and —COO$C_{1-4}$alkyl, or, alternatively, two adjacent R$^a$, may be taken together with the carbons of attachment to form a fused ring and selected from the group consisting of phenyl, pyridyl and pyrimidinyl;

or alternatively, R$^2$ and one of R$^a$ can be taken together to be —CH$_2$— or >C=O and to form a fused ring to the phenyl;

$R^b$ is, independently, selected from the group consisting of $C_{1-4}$alkyl and halogen;

and enantiomers, diastereomers, hydrates, solvates and pharmaceutically acceptable salts, esters and amides thereof.

The invention also features pharmaceutical compositions containing such compounds and methods of using such compositions in the treatment or prevention of disease states mediated by CCK2 receptor activity.

DETAILED DESCRIPTION

Preferably, $R^1$ and $R^2$ are independently selected from the group consisting of H, a) $C_{1-7}$alkyl, ethenyl, propenyl, butenyl, ethynyl, propynyl, cyclobutyl, cyclopentyl, cyclohexyl, cycloheptyl, cyclopentenyl, cyclohexenyl, indan-1-yl, 1,2,3,4-tetrahydro-naphthalen-1-yl, 6,7,8,9-tetrahydro-5H-benzocyclohepten-5-yl, cyclobutyl$C_{1-4}$alkyl, cyclopentyl$C_{1-4}$alkyl, cyclohexyl$C_{1-4}$alkyl, cycloheptyl$C_{1-4}$alkyl, b) phenyl, 6,7,8,9-tetrahydro-5H-benzocyclohepten-1,2,3 or 4-yl, optionally 5,6,7,8 or 9 oxo substituted, 5,6,7,8-tetrahydro-naphthalen-1,2,3 or 4-yl, optionally 5,6, 7 or 8 oxo substituted, benzyl, 6,7,8,9-tetrahydro-5H-benzocyclohepten-1,2,3 or 4-ylmethyl, optionally 5,6,7,8 or 9 oxo substituted, 5,6,7,8-tetrahydro-naphthalen-1,2,3 or 4-ylmethyl, optionally 5,6,7 or 8 oxo substituted, 1-phenyleth-1-yl, benzhydryl, naphthylmethyl, benzoylmethyl, 1-benzoyleth-1-yl, c) pyridylmethyl, pyrazinylmethyl, pyrimidinylmethyl, pyridazinylmethyl, quinolin-2,3 or 4-ylmethyl, isoquinolin-1,3 or 4-ylmethyl, quinazolin-2 or 4-ylmethyl, quinoxalin-2 or 3-ylmethyl, d) furanylmethyl, thiophenylmethyl, 1-(H or $C_{1-4}$alkyl) pyrrolylmethyl, oxazolylmethyl, thiazolylmethyl, pyrazolylmethyl, imidazolylmethyl, isoxazolylmethyl, isothiazolylmethyl, benzofuran-2 or 3-ylmethyl, benzothiophen-2 or 3-ylmethyl, 1-(H or $C_{1-4}$alky)-1H-indol-2 or 3-ylmethyl, 1-(H or $C_{1-4}$alkyl)-1H-benzimidazol-2-ylmethyl, benzooxazol-2-ylmethyl, benzothiazol-2-ylmethyl, e) quinolin-5,6,7 or 8-ylmethyl, isoquinolin-5,6,7 or 8-ylmethyl, quinazolin-5,6,7 or 8-ylmethyl, quinoxalin-5,6,7 or 8-ylmethyl, f) benzofuran-4,5,6 or 7-ylmethyl, benzothiophen-4,5,6 or 7-ylmethyl, 1-(H or $C_{1-4}$alky)-1H-indol-4,5,6 or 7-ylmethyl, 1-(H or $C_{1-4}$alkyl)-1H-benzimidazol-4,5,6 or 7-ylmethyl, benzooxazol-4,5,6 or 7-ylmethyl, benzothiazol-4,5,6 or 7-ylmethyl, g) $C_{1-4}$alkylO- and HS$C_{1-4}$alkyl, where each of a) to g) is substituted with 0, 1, 2, or 3 of $R^q$ and for those groups in which $R^s$ is hydrogen, up to one $R^s$ may be other than hydrogen.

Most preferably, $R^1$ and $R^2$ are independently selected from the group consisting of hydrogen, methyl, ethyl, butyl, hexyl, phenyl, 6,7,8,9-tetrahydro-5H-benzocyclohepten-2-yl, optionally 5,6,7,8 or 9 oxo substituted, benzyl, 1-phenyleth-1-yl, furanylmethyl, benzoylethyl, 1-benzoyleth-1-yl, methylO-, cyclohexyl, cyclohexylmethyl, pyridylethyl, naphthylmethyl, 1,2,3,4-tetrahydro-naphthalen-1-yl, benzhydryl, where each member is substituted with 0, 1, 2, or 3 of $R^q$ and, optionally, for those groups in which $R^s$ is hydrogen, up to one $R^s$ may be other than hydrogen.

Specific $R^1$ and $R^2$ are independently selected from the group consisting of hydrogen, methyl, ethyl, butyl, phenyl, benzyl, 2-bromobenzyl, 2-chlorobenzyl, 4-chlorobenzyl, 2,4-dichlorobenzyl, 3,4-dichlorobenzyl, 2,6-dichlorobenzyl, 2,4,6-trichlorobenzyl, 2-fluorobenzyl, 4-fluorobenzyl, 2,4-difluorobenzyl, 2,6-difluorobenzyl, 2,4,6-trifluorobenzyl, 2-chloro-4-fluorobenzyl, 2-fluoro-4-bromobenzyl, 2-fluoro-4-chlorobenzyl, 2-methylbenzyl, 2-methylsulfanylbenzyl, 2-trifluoromethylbenzyl, 1-phenyleth-1-yl, 1-phenylprop-1-yl, 1-(4-bromophenyl)eth-1-yl, 1-(4-fluorophenyl)eth-1-yl, 1-(2,4-dibromophenyl)eth-1-yl, 1-(2,4-dichlorophenyl)eth-1-yl, 1-(3,4-dichlorophenyl)eth-1-yl, 1-(2,4-difluorophenyl)eth-1-yl, 2-fluoro-1-(2,4-difluorophenyl)eth-1-yl, 2-fluoro-1-(4-fluorophenyl)eth-1-yl, 1-(4-methylphenyl)eth-1-yl, 1-methyl-1-phenyleth-1-yl, 2,2,2-trifluoro-1-phenyleth-1-yl, 2,2,2-trifluoro-1-(2,4-difluorophenyl)eth-1-yl, 1-phenyl-2-dimethylaminoeth-1-yl, 1-benzoyleth-1-yl, cyclohexyl, 1-cyclohexyleth-1-yl, furan-2-ylmethyl, naphth-1-ylmethyl, methoxy, methylSethyl, 6-methyl-6-hydroxyhept-2-yl, pyrid-2-ylethyl, 1,2,3,4-tetrahydro-naphthalen-1-yl, 1-phenyl-2-hydroxyeth-1-yl, benzhydryl, 4-hydroxymethylpiperidin-1-yl, 1-furan-2-yl-2-phenyleth-1-yl and 9-oxo-6,7,8,9-tetrahydro-5H-benzocyclohepten-2-yl.

It is preferred that one of $R^1$ and $R^2$ is H or $C_{1-4}$alkyl where the other is not H or $C_{1-4}$alkyl. It is also preferred that one of $R^1$ and $R^2$ is H, methyl or ethyl.

In another preferred embodiment, at least one of $R^1$ and $R^2$ are selected from the groups consisting of

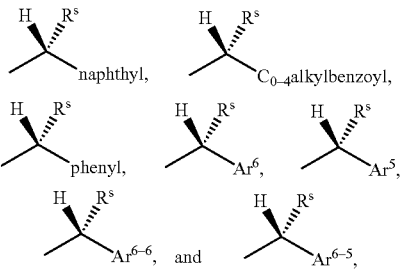

with the proviso that said $R^s$ is not hydrogen, said phenyl is optionally fused at two adjacent carbon atoms to $R^f$ and, except in positions where "$R^s$" or "H" is specifically indicated, each member is substituted with 0, 1, 2, or 3 of $R^q$.

Preferably, $R^f$ is selected from the group consisting of —CH$_2$CH$_2$CH$_2$—, —CH$_2$CH$_2$CH$_2$CH$_2$—, —CH$_2$CH$_2$CH$_2$CH$_2$CH$_2$— and —(C=O)CH$_2$CH$_2$CH$_2$—.

Preferably, $R^s$ is selected from the group consisting of hydrogen, methyl, ethyl, propyl, trifluoromethyl, haloethyl, aminomethyl, methylaminomethyl, dimethylaminomethyl, hydroxymethyl, methoxymethyl, thiomethyl, methylthiomethyl and phenyl.

Most preferably, $R^s$ is selected from the group consisting of H, methyl, ethyl, hydroxymethyl, fluoromethyl and dimethylaminomethyl.

Preferably, $R^q$ is selected from the group consisting of methyl, ethyl, propyl, t-butyl, hydroxy, fluoro, chloro, bromo, iodo, trifluoromethyl, aminomethyl, methylaminomethyl, dimethylaminomethyl, hydroxymethyl, methoxymethyl, thiomethyl, methylthiomethyl, methoxy, ethoxy, methylmercapto and ethylmercapto.

Most preferably, $R^q$ is selected from the group consisting of methyl, hydroxy, fluoro, chloro, bromo, iodo and trifluoromethyl.

Preferably, $R^1$ and $R^2$ taken together with the nitrogen to which they are attached are selected from the group consisting of i) 10-oxa-4-aza-tricyclo[5.2.1.0$^{2,6}$]dec-4-yl, ii) 2-pyrrolin-1-yl, 3-pyrrolin-1-yl, pyrrolidin-1-yl, 2-imidazolin-1-yl, 3-(H or $R^p$)imidazolidin-1-yl, piperidin-1-yl, morpholin-4-yl, thiomorpholin-4-yl, 3-(H or $R^p$)piperazin- 1-yl, azepan-1-yl, thiazolidin-3-yl, oxazolidin-3-yl, 2,5-dihydro-pyrrol-1-yl, azetidin-1-yl, where each member of ii) in each ring has 0 or 1 unsaturated bond and has 0, 1 or 2 carbon members which is a carbonyl, iii) 3,4-dihydro-2H-quinolin-1-yl, 3,4-dihydro-2H-quinolin-2-yl, 2,3-dihydro-indol-1-yl, 1,3-dihydro-isoindol-2-yl, 1-oxo-1,3-dihydro-isoindol-2-yl, tetrahydro-benzo[b, c or d]azepin-1-yl, 2,3-dihydro-benzo[e or f][1,4]oxazepin-4-yl, where each member of iii) in each ring has 0 or 1 unsaturated bond and has 0, 1 or 2 carbon members which are a carbonyl, iv) decahydro-quinolin-1-yl, octahydro-isoquinolin-2-yl, octahydro-[1 or 2]pyrindin-1 or 2-yl, octahydro-indol-1-yl, octahydro-isoindol2-yl, hexahydro-cyclopenta[b]pyrrol-1-yl, hexahydro-cyclopenta[c]pyrrol-2-yl, (5,6,7 or 8-H or $R^p$)-decahydro-[1,5 or 1,6 or 1,7 or 1,8]naphthyridin-1-yl, (5,6,7 or 8-H or $R^p$)-decahydro-[2,5 or 2,6 or 2,7 or 2,8] naphthyridin-2-yl, 1-H or $R^p$-octahydro-pyrrolo[2,3-c]pyridin-6-yl, 2-H or $R^p$-octahydro-pyrrolo[3,4-c]pyridin-5-yl, 1-H or $R^p$-octahydro-pyrrolo[3,2-c]pyridin-5-yl, 1-H or $R^p$-octahydro-pyrrolo[2,3-b]pyridin-7-yl, 6-H or $R^p$-octahydro-pyrrolo[3,4-b]pyridin-1-yl, 1-H or $R^p$-octahydro-pyrrolo[3,2-b]pyridin-4-yl, 5-H or $R^p$-octahydro-pyrrolo[3,4-c]pyridin-2-yl, 6-H or $R^p$-octahydro-pyrrolo[2,3-c]pyridin-1-yl, 1-H or $R^p$-octahydro-pyrrolo[3,4-b]pyridin-6-yl, 7-H or $R^p$-octahydro-pyrrolo[2,3-b]pyridin-1-yl, octahydro-1,5-methano-pyrido[1,2-a][1,5]diazocin-3-yl, where each member of iv) in each ring has 0, 1 or 2 carbon members which is a carbonyl, each ring of attachment has 0 or 1 unsaturated bonds and each secondary ring has 0, 1 or 2 unsaturated bonds, v) 8-oxo-1,5,6,8-tetrahydro-2H,4H-1,5-methano-pyrido[1,2-a][1,5]diazocin-3-yl, where each member of i), ii), iii), iv) or v) is further substituted with 0, 1 or 2 of $R^p$.

Most preferably, $R^1$ and $R^2$ taken together with the nitrogen to which they are attached are selected from the group consisting of 10-oxa-4-aza-tricyclo[5.2.1.0$^{2,6}$]dec-4-yl, 2-pyrrolin-1-yl, 3-pyrrolin-1-yl, pyrrolidin-1-yl, 2-imidazolin-1-yl, imidazolidin-1-yl, piperidin-1-yl, morpholin-4-yl, thiomorpholin-4-yl, piperazin-1-yl, azepan-1-yl, tetrahydrobenzo[c]azepin-1-yl, tetrahydro-halobenzo[c]azepin-1-yl, 2,3-dihydro-benzo[f][1,4]oxazepin-4-yl, 2,3-dihydro-halobenzo[f][1,4]oxazepin-4-yl, thiazolidin-3-yl, oxazolidin-3-yl, 2,5-dihydro-pyrrol-1-yl, 8-oxo-1,5,6,8-tetrahydro-2H,4H-1,5-methano-pyrido[1,2-a][1,5]diazocin-3-yl, azetidin-1-yl, octahydro-quinolin-1-yl, 3,4-dihydro-2H-quinolin-1-yl, 3,4-dihydro-2H-quinolin-2-yl, where each member is further substituted with 0, 1 or 2 of $R^p$.

Specific $R^1$ and $R^2$ taken together with the nitrogen to which they are attached are selected from the group consisting of 1-methyl-10-oxa-4-aza-tricyclo[5.2.1.0$^{2,6}$]dec-4-yl, azetidin-1-yl, pyrrolidin-1-yl, 2-hydroxymethylpyrrolidin-1-yl, 2,4-dimethyl-3-ethylpyrrolidin-1-yl, piperidin-1-yl, 2-methylpiperidin-1-yl, 4-hydroxypiperidin-1-yl, 4-hydroxymethylpiperidin-1-yl, 4-phenylpiperidin-1-yl, azepan-1-yl, tetrahydro-benzo[c]azepin-1-yl, 7-fluoro-tetrahydro-benzo[c]azepin-1-yl, 2,3-dihydro-benzo[f][1,4]oxazepin-4-yl, 8-fluoro-2,3-dihydro-benzo[f][1,4]oxazepin-4-yl, 6,8-difluoro-2,3-dihydro-benzo[f][1,4]oxazepin-4-yl, 4-(2-hydroxyphenyl)piperazin-1-yl, morpholin-4-yl, 2-methylmorpholin-4-yl, 2,6-dimethylmorpholin-4-yl, octahydro-isoquinolin-2-yl, decahydro-quinolin-1-yl, thiazolidin-3-yl, 2,5-dimethyl-2,5-dihydro-pyrrol-1-yl, 8-oxo-1,5,6,8-tetrahydro-2H,4H-1,5-methano-pyrido[1,2-a][1,5]diazocin-3-yl and 3,4-dihydro-2H-quinolin-2-yl.

Preferably, $R^p$ is selected from the group consisting of hydroxy, methyl, ethyl, propyl, hydroxymethyl, hydroxyethyl, phenyl, p-halophenyl, m-halophenyl, o-halophenyl, phenyl and p-hydroxyphenyl.

Most preferably, $R^p$ is selected from the group consisting of hydroxy, methyl, ethyl, hydroxymethyl, hydroxyethyl, phenyl, mono-fluorosubstituted phenyl and mono-chlorosubstituted phenyl.

Preferably, $R^a$ is selected from the group consisting of methyl, ethyl, propyl, ethenyl, propenyl, cyclopropyl, cyclobutyl, phenyl, furanyl, thienyl, pyrrol-1-yl, benzyl, methoxy, ethoxy, propoxy, cyclopropoxy, cyclobutoxy, cyclopentoxy, phenoxy, benzoxy, —SH, -Smethyl, -Sethyl, —S-t-butyl, -Scyclopropyl, -Sphenyl, -Sbenzyl, nitro, cyano, amino, dimethylamino, (cyclohexylmethyl)amino, acetyl, —SCF$_3$, I, F, Cl, Br, trifluoromethyl, —OCF$_3$ and carboxymethyl.

Preferably, there is one $R^a$. More preferably, there is one $R^a$ positioned on the ring para to the amide substituent.

Preferably, where two adjacent $R^a$ are taken together with the carbons of attachment to form a fused ring, the fused ring is phenyl.

Most preferably, $R^a$ is selected from the group consisting of nitro, cyano, F, Cl, Br, fused phenyl, I, CF$_3$, methoxy, ethoxy, propoxy, i-propoxy, ethenyl, cyclopentoxy, 2-propenyl, phenyl, furanyl, thienyl, amino, pyrrol-1-yl, dimethylamino, (cyclohexylmethyl)amino, —SCH$_3$, -Sethyl, —S-t-butyl, -Sbenzyl, —SCF$_3$, i-propyl and methyl.

Preferably, $R^b$ is absent or selected from the group consisting of methyl, ethyl, I, F, Cl and Br.

Most preferably, $R^b$ is absent.

Pharmaceutically acceptable salts include amino addition salts that are pharmacologically effective. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. See example, S. M. Berge, et al., "Pharmaceutical Salts," J. Pharm. Sci., 1977, 66:1-19, which is incorporated herein by reference.

Preferred compounds of the present invention are selected from the group consisting of:

| EX | CHEMICAL NAME |
|---|---|
| 1 | (R)-4-Bromo-N-[1-(2,4-dichlorophenyl)-ethyl]-2-(quinoxaline-5-sulfonylamino)-benzamide; |
| 2 | (R)-4-Bromo-N-[1-(2,4-difluoro-phenyl)-ethyl]-2-(quinoxaline-5-sulfonylamino)-benzamide; |
| 3 | (R)-4-Chloro-N-[1-(2,4-difluorophenyl)-ethyl]-2-(quinoxaline-5-sulfonylamino)-benzamide; |
| 5 | (R)-4,5-Dichloro-N-[1-(2,4-difluorophenyl)ethyl]-2-(quinoxaline-5-sulfonylamino)-benzamide; |
| 7 | (R)-4-Chloro-N-[1-(4-fluorophenyl)-ethyl]-2-(quinoxaline-5-sulfonylamino)-benzamide; |
| 8 | (R)-4-Bromo-N-[1-(4-fluorophenyl)-ethyl]-2-(quinoxaline-5-sulfonylamino)-benzamide; |
| 9 | (S)-4-Chloro-N-[1-(2,4-dichlorophenyl)ethyl]-2-(quinoxaline-5-sulfonylamino)-benzamide; |
| 15 | (R)-N-[1-(2,4-Difluorophenyl)-ethyl]-4-iodo-2-(quinoxaline-5-sulfonylamino)-benzamide; |
| 16 | 4-Bromo-N-(2-chloro-4-fluoro-benzyl)-2-(quinoxaline-5-sulfonylamino)-benzamide; |
| 17 | 4-Bromo-N-(2,4-difluoro-benzyl)-2-(quinoxaline-5-sulfonylamino)-benzamide; |
| 29 | (S)-4-Chloro-N-[1-(2,4-difluoro-phenyl)-2,2,2-trifluoroethyl]-2-(quinoxaline-5-sulfonylamino)-benzamide; |
| 30 | (S)-4-Bromo-N-[1-(2,4-difluoro-phenyl)-2,2,2-trifluoroethyl]-2-(quinoxaline-5-sulfonylamino)-benzamide; |

| EX | CHEMICAL NAME |
|---|---|
| 33 | (R)-4-Bromo-N-methyl-N-(1-phenyl-ethyl)-2-(quinoxaline-5-sulfonylamino)-benzamide; |
| 34 | (R)-4-Iodo-N-methyl-N-(1-phenyl-ethyl)-2-(quinoxaline-5-sulfonylamino)-benzamide; |
| 35 | N-(4-Fluorobenzyl)-4-iodo-N-methyl-2-(quinoxaline-5-sulfonylamino)-benzamide; |
| 36 | (R)-N-[1-(2,4-Difluorophenyl)ethyl]-2-(quinoxaline-5-sulfonylamino)-4-trifluoromethylbenzamide; |
| 37 | (R)-N-[1-(2,4-Dichloro-phenyl)-ethyl]-4-fluoro-2-(quinoxaline-5-sulfonylamino)-benzamide; |
| 38 | (R)-4-Cyano-N-[1-(2,4-difluoro-phenyl)ethyl]-2-(quinoxaline-5-sulfonylamino)-benzamide; |
| 41 | N-Benzyl-4-bromo-N-methyl-2-(quinoxaline-5-sulfonylamino)-benzamide; |
| 42 | N-Benzyl-4-iodo-N-methyl-2-(quinoxaline-5-sulfonylamino)-benzamide; |
| 43 | (R)-4-Chloro-N-[1-(2,4-dichloro-phenyl)-ethyl]-2-(quinoxaline-5-sulfonylamino)-benzamide; |
| 44 | 4-Chloro-N-(4-fluoro-benzyl)-N-methyl-2-(quinoxaline-5-sulfonylamino)-benzamide; |
| 45 | 4-Bromo-N-(4-fluoro-benzyl)-N-methyl-2-(quinoxaline-5-sulfonylamino)-benzamide; |
| 46 | 4-Chloro-N-(4-chloro-benzyl)-N-methyl-2-(quinoxaline-5-sulfonylamino)-benzamide; |
| 47 | 4-Bromo-N-(4-chloro-benzyl)-N-methyl-2-(quinoxaline-5-sulfonylamino)-benzamide; |
| 48 | N-(4-Chloro-benzyl)-4-iodo-N-methyl-2-(quinoxaline-5-sulfonylamino)-benzamide; |
| 49 | 4-Chloro-N-[1-(4-chloro-phenyl)-ethyl]-2-(quinoxaline-5-sulfonylamino)-benzamide; |
| 50 | 4-Bromo-N-[1-(4-chloro-phenyl)-ethyl]-2-(quinoxaline-5-sulfonylamino)-benzamide; |
| 51 | N-[1-(4-Chloro-phenyl)-ethyl]-4-iodo-2-(quinoxaline-5-sulfonylamino)-benzamide; |
| 52 | 4-Chloro-N-[1-(4-fluoro-phenyl)-ethyl]-2-(quinoxaline-5-sulfonylamino)-benzamide; |
| 53 | 4-Bromo-N-[1-(4-fluoro-phenyl)-ethyl]-2-(quinoxaline-5-sulfonylamino)-benzamide; |
| 54 | N-[1-(4-Fluoro-phenyl)-ethyl]-4-iodo-2-(quinoxaline-5-sulfonylamino)-benzamide; |
| 55 | 4-Chloro-N-(2,4-difluoro-benzyl)-2-(quinoxaline-5-sulfonylamino)-benzamide; |
| 56 | N-(2,4-Difluoro-benzyl)-4-iodo-2-(quinoxaline-5-sulfonylamino)-benzamide; |
| 57 | N-(2,4-Difluoro-benzyl)-4-iodo-2-(quinoxaline-5-sulfonylamino)-benzamide; |
| 58 | 4-Chloro-N-(2,4-dichloro-benzyl)-2-(quinoxaline-5-sulfonylamino)-benzamide; |
| 59 | 4-Bromo-N-(2,4-dichloro-benzyl)-2-(quinoxaline-5-sulfonylamino)-benzamide; |
| 60 | N-(2,4-Dichloro-benzyl)-4-iodo-2-(quinoxaline-5-sulfonylamino)-benzamide; |
| 61 | 4-Chloro-N-(2-chloro-4-fluoro-benzyl)-2-(quinoxaline-5-sulfonylamino)-benzamide; |
| 62 | (R)-4-Chloro-N-methyl-N-(1-phenyl-ethyl)-2-(quinoxaline-5-sulfonylamino)-benzamide; |
| 63 | (R)-N-[1-(4-Fluoro-phenyl)-ethyl]-4-iodo-2-(quinoxaline-5-sulfonylamino)-benzamide; |
| 64 | (R)-N-[1-(2,4-Dichloro-phenyl)-ethyl]-4-iodo-2-(quinoxaline-5-sulfonylamino)-benzamide; |
| 65 | (S)-4-Bromo-N-[1-(2,4-dichloro-phenyl)-ethyl]-2-(quinoxaline-5-sulfonylamino)-benzamide; |
| 66 | (S)-N-[-(2,4-Dichloro-phenyl)-ethyl]-4-iodo-2-(quinoxaline-5-sulfonylamino)-benzamide; |
| 67 | (S)-N-[1-(2,4-Difluoro-phenyl)-2,2,2-trifluoro-ethyl]-4-iodo-2-(quinoxaline-5-sulfonylamino)-benzamide; |
| 68 | (R)-N-[1-(2,4-Dichloro-phenyl)-ethyl]-2-(quinoxaline-5-sulfonylamino)-4-trifluoromethyl-benzamide; |
| 69 | (R)-4-Cyano-N-[1-(2,4-dichloro-phenyl)-ethyl]-2-(quinoxaline-5-sulfonylamino)-benzamide; |
| 70 | (R)-N-[1-(2,4-Difluoro-phenyl)-ethyl]-4-fluoro-2-(quinoxaline-5-sulfonylamino)-benzamide; |
| 71 | (S)-4-Bromo-N-[2-fluoro-1-(4-fluoro-phenyl)-ethyl]-2-(quinoxaline-5-sulfonylamino)-benzamide; |
| 72 | (S)-4-Chloro-N-[2-fluoro-1-(4-fluoro-phenyl)-ethyl]-2-(quinoxaline-5-sulfonylamino)-benzamide; |
| 73 | (S)-N-[2-Fluoro-1-(4-fluoro-phenyl)-ethyl]-4-iodo-2-(quinoxaline-5-sulfonylamino)-benzamide; |
| 74 | 4-Bromo-N-[1-(2,4-difluoro-phenyl)-2-fluoro-ethyl]-2-(quinoxaline-5-sulfonylamino)-benzamide; |
| 75 | N-[1-(2,4-Difluoro-phenyl)-2-fluoro-ethyl]-4-iodo-2-(quinoxaline-5-sulfonylamino)-benzamide; |
| 76 | (S)-4-Bromo-N-[1-(2,4-difluoro-phenyl)-2-fluoro-ethyl]-2-(quinoxaline-5-sulfonylamino)-benzamide; |
| 77 | (S)-N-[1-(2,4-Difluoro-phenyl)-2-fluoro-ethyl]-4-iodo-2-(quinoxaline-5-sulfonylamino)-benzamide; |
| 78 | (S)-4-Chloro-N-[1-(2,4-difluoro-phenyl)-2-fluoro-ethyl]-2-(quinoxaline-5-sulfonylamino)-benzamide; and |
| 96 | Quinoxaline-5-sulfonic acid [6-bromo-2-(2,4-difluoro-benzyl)-1,3-dioxo-2,3-dihydro-1H-isoindol-4-yl]-amide. |

Additional preferred compounds of the present invention are selected from the group consisting of:

| EX | CHEMICAL NAME |
|---|---|
| 4 | Quinoxaline-5-sulfonic acid [5-iodo-2-(piperidine-1-carbonyl)-phenyl]-amide; |
| 6 | Quinoxaline-5-sulfonic acid [5-iodo-2-(morpholine-4-carbonyl)-phenyl]-amide; |
| 10 | Quinoxaline-5-sulfonic acid [5-bromo-2-(1,3,4,5-tetrahydrobenzo[c]azepine-2-carbonyl)phenyl]-amide; |
| 11 | (R)-Quinoxaline-5-sulfonic acid [5-bromo-2-(morpholine-4-carbonyl)-phenyl]-amide; |
| 12 | (R)-Quinoxaline-5-sulfonic acid [5-bromo-2-(3-methylmorpholine-4-carbonyl)-phenyl]-amide; |
| 13 | (R)-Quinoxaline-5-sulfonic acid [5-chloro-2-(3-methylmorpholine-4-carbonyl)-phenyl]-amide; |
| 14 | (R)-Quinoxaline-5-sulfonic acid [5-chloro-2-(morpholine-4-carbonyl)phenyl]-amide; |
| 18 | Quinoxaline-5-sulfonic acid [2-(azepane-1-carbonyl)-5-iodophenyl]-amide; |
| 19 | (R)-Quinoxaline-5-sulfonic acid [5-iodo-2-(3-methylmorpholine-4-carbonyl)-phenyl]-amide; |
| 20 | Quinoxaline-5-sulfonic acid [4,5-dichloro-2-(morpholine-4-carbonyl)-phenyl]-amide; |
| 21 | Quinoxaline-5-sulfonic acid [2-(azepane-1-carbonyl)-5-bromophenyl]-amide; |
| 22 | Quinoxaline-5-sulfonic acid [5-chloro-2-(2,3-dihydro-5H-benzo[f][1,4]oxazepine-4-carbonyl)-phenyl]-amide; |
| 23 | (S)-Quinoxaline-5-sulfonic acid [5-iodo-2-(3-methylmorpholine-4-carbonyl)-phenyl]-amide; |
| 24 | Quinoxaline-5-sulfonic acid [5-bromo-2-(7-fluoro-1,3,4,5-tetrahydro-benzo[c]azepine-2-carbonyl)-phenyl]-amide; |
| 25 | (R,S)-Quinoxaline-5-sulfonic acid [2-(3,5-dimethylmorpholine-4-carbonyl)-5-iodophenyl]-amide; |
| 26 | Quinoxaline-5-sulfonic acid [2-(4-hydroxy-piperidine-1-carbonyl)-5-iodo-phenyl]-amide; |
| 27 | meso-Quinoxaline-5-sulfonic acid [2-(3,5-dimethylmorpholine-4-carbonyl)-5-bromophenyl]-amide; |
| 28 | (S)-Quinoxaline-5-sulfonic acid [5-bromo-2-(3-methylmorpholine-4-carbonyl)-phenyl]-amide; |
| 31 | Quinoxaline-5-sulfonic acid [2-(4-hydroxy-piperidine-1-carbonyl)-5-bromo-phenyl]-amide; |
| 32 | Quinoxaline-5-sulfonic acid [5-bromo-2-(piperidine-1-carbonyl)-phenyl]-amide; |
| 39 | Quinoxaline-5-sulfonic acid [5-bromo-2-(8-fluoro-2,3-dihydro-5H-benzo[f][1,4]oxazepine-4-carbonyl)phenyl]-amide; |
| 40 | Quinoxaline-5-sulfonic acid [5-chloro-2-(6,8-difluoro-2,3-dihydro-5H-benzo[f][1,4]oxazepine-4-carbonyl)-phenyl]-amide; |
| 79 | Quinoxaline-5-sulfonic acid [5-chloro-2-(piperidine-1-carbonyl)-phenyl]-amide; |
| 80 | Quinoxaline-5-sulfonic acid [5-chloro-2-(1,3,4,5-tetrahydro-benzo[c]azepine-2-carbonyl)-phenyl]-amide; |
| 81 | Quinoxaline-5-sulfonic acid [5-iodo-2-(1,3,4,5-tetrahydro-benzo[c]azepine-2-carbonyl)-phenyl]-amide; |
| 82 | Quinoxaline-5-sulfonic acid [5-bromo-2-(2,3-dihydro-5H-benzo[f][1,4]oxazepine-4-carbonyl)-phenyl]-amide; |
| 83 | Quinoxaline-5-sulfonic acid [2-(2,3-dihydro-5H-benzo[f][1,4]oxazepine-4-carbonyl)-5-iodo-phenyl]-amide; |

| EX | CHEMICAL NAME |
|---|---|
| 84 | (S)-Quinoxaline-5-sulfonic acid [5-chloro-2-(3-methyl-morpholine-4-carbonyl)-phenyl]-amide; |
| 85 | meso-Quinoxaline-5-sulfonic acid [5-chloro-2-(3,5-dimethyl-morpholine-4-carbonyl)-phenyl]-amide; |
| 86 | Quinoxaline-5-sulfonic acid [5-chloro-2-(7-fluoro-1,3,4,5-tetrahydro-benzo[c]azepine-2-carbonyl)-phenyl]-amide; |
| 87 | Quinoxaline-5-sulfonic acid [2-(7-fluoro-1,3,4,5-tetrahydro-benzo[c]azepine-2-carbonyl)-5-iodo-phenyl]-amide; |
| 88 | Quinoxaline-5-sulfonic acid [2-(azepane-1-carbonyl)-5-chloro-phenyl]-amide; |
| 89 | Quinoxaline-5-sulfonic acid [5-chloro-2-(8-fluoro-2,3-dihydro-5H-benzo[f][1,4]oxazepine-4-carbonyl)-phenyl]-amide; |
| 90 | Quinoxaline-5-sulfonic acid [2-(8-fluoro-2,3-dihydro-5H-benzo[f][1,4]oxazepine-4-carbonyl)-5-iodo-phenyl]-amide; |
| 91 | Quinoxaline-5-sulfonic acid [2-(piperidine-1-carbonyl)-5-trifluoromethyl-phenyl]-amide; |
| 92 | Quinoxaline-5-sulfonic acid [2-(morpholine-4-carbonyl)-5-trifluoromethyl-phenyl]-amide; |
| 93 | Quinoxaline-5-sulfonic acid [5-bromo-2-(6,8-difluoro-2,3-dihydro-5H-benzo[f][1,4]oxazepine-4-carbonyl)-phenyl]-amide; |
| 94 | Quinoxaline-5-sulfonic acid [2-(6,8-difluoro-2,3-dihydro-5H-benzo[f][1,4]oxazepine-4-carbonyl)-5-iodo-phenyl]-amide; and |
| 95 | Quinoxaline-5-sulfonic acid [2-(6,8-difluoro-2,3-dihydro-5H-benzo[f][1,4]oxazepine-4-carbonyl)-5-trifluoromethyl-phenyl]-amide. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

The amidophenyl-sulfonylamino-quinoxalines of formula (I) may be produced by a number of reaction schemes. In Scheme A, sulfonylation is the final step of the process and in Scheme B, sulfonylation is the initial step of the process. Persons skilled in the art will recognize that certain compounds are more advantageously produced by one scheme as compared to the other.

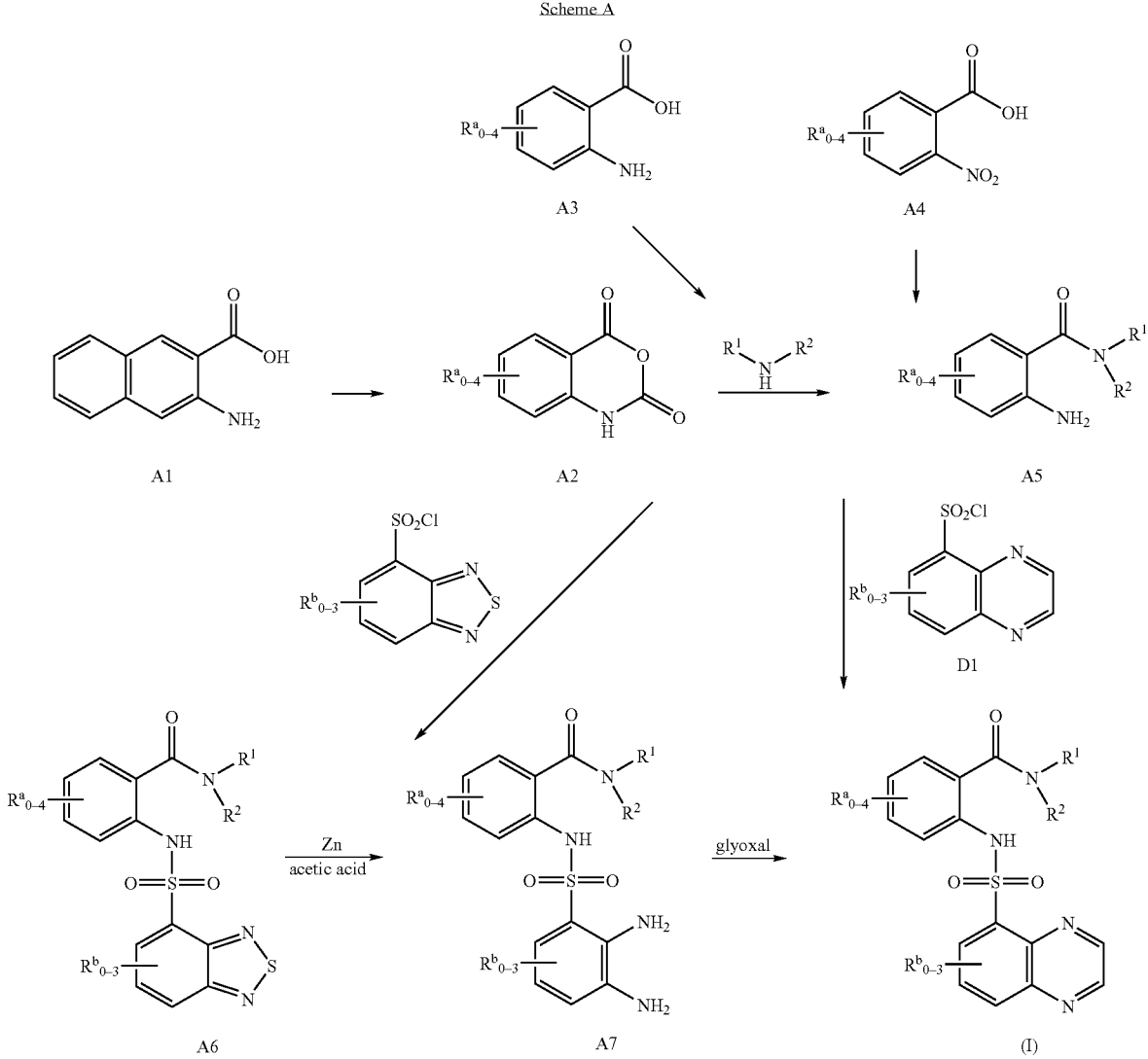

Referring to Scheme A, commercially available aminonaphthoic acid A1 is reacted with triphosgene and Hünig's base to produce the benzofused isatoic anhydride species of the genus A2. Various isatoic anhydrides A2 are available commercially. An amine is acylated with the isatoic anhydride A2 to produce a benzamide A5. Benzamide A5 may also be obtained from commercially available anthranilic acid A3 through peptide coupling. Benzamide A5 may additionally be obtained from commercially available nitrobenzoic acid A4 through peptide coupling followed by reduction of the nitro group. In one synthetic pathway, benzamide A5 is sulfonylated with quinoxaline sulfonyl chloride D1 to produce quinoxaline sulfonamide compounds (I). In a second synthetic pathway, benzamide A5 is first sulfonylated with the sulfonyl chloride to produce benzothiadiazole compounds A6. This first step is followed by reduction of the benzothiadiazole to extrude sulfur resulting in phenylene diamine A7, which is condensed with glyoxal to produce quinoxaline sulfonamide compounds (I). Where $R^a$ or $R^b$ is a primary or secondary amine or hydroxy, they can be protected with common protecting groups. In the case of the primary or secondary amine, there can be employed Boc or Cbz. In the case of hydroxy, there can be employed TBS, TES or benzyl. Of course, a precursor substituent may be employed in the reaction steps and later transformed into the desired substituent. For example, where A6 is produced with $R^a$ as nitro, the nitro may be reduced to the amine, and the amine may be, for example, alkylated, acylated, diazotized, etc.

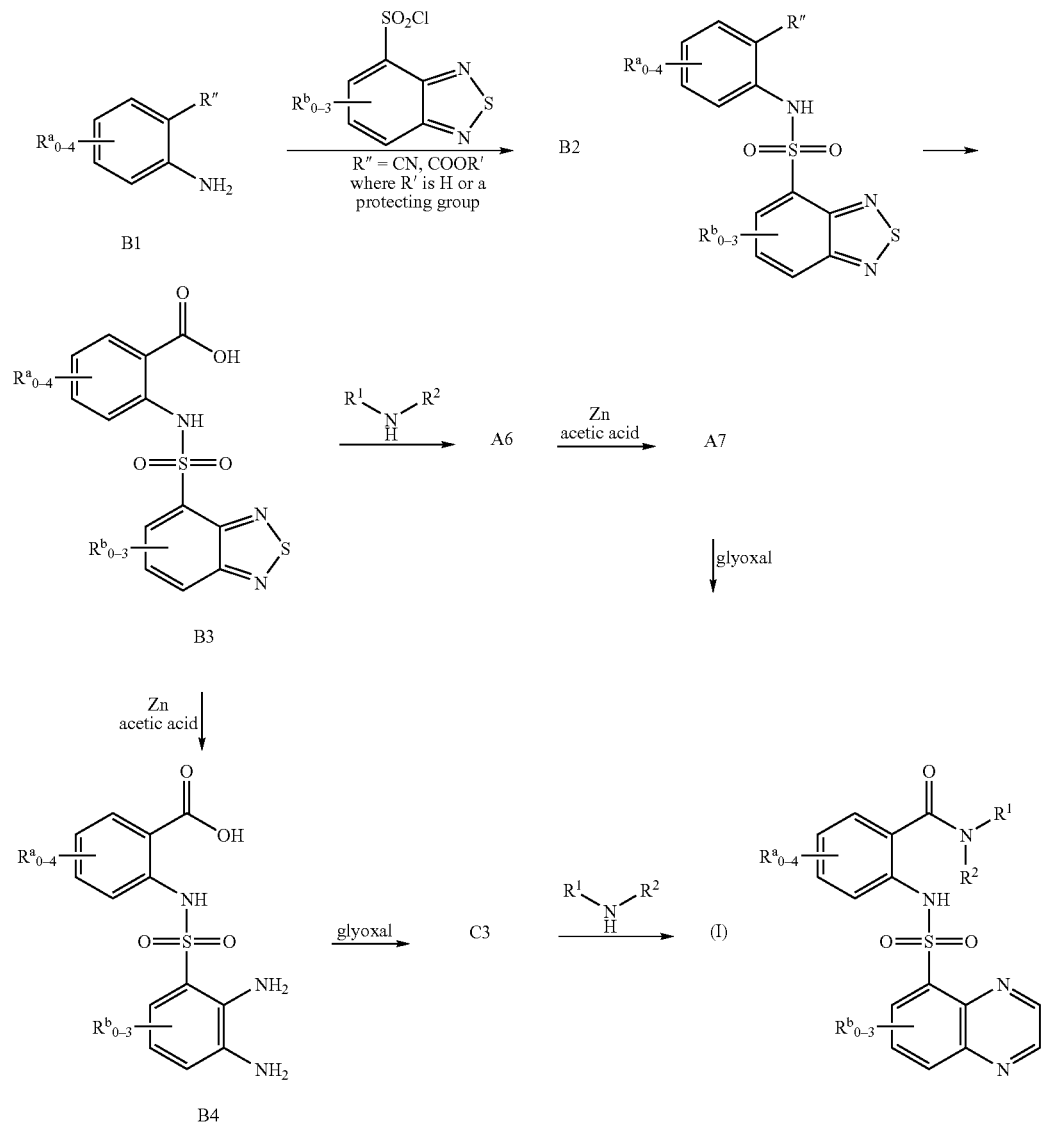

Scheme B

Referring to Scheme B, aniline B1 is sulfonylated to sulfonamide B2. In the case that R″ is ester or cyano, the ester or cyano is hydrolyzed to the carboxylic acid B3. In a first route, acid B3 undergoes peptide coupling under standard conditions with an amine to produce benzothiadiazole compounds A6. This coupling is followed by reduction of the benzothiadiazole to extrude sulfur resulting in phenylene diamine A7, which is condensed with a two carbon synthon to produce quinoxaline sulfonamide compounds (I). In a second route, acid B3 is reduced to extrude sulfur resulting in phenylene diamine B4, which is condensed with a two-carbon synthon to produce quinoxaline sulfonamide C3. Sulfonamide C3 undergoes peptide couple coupling under standard conditions to produce quinoxaline sulfonamide compounds (I). Where $R^a$ or $R^b$ is a primary or secondary amine or hydroxy, it can be protected with common protecting groups. In the case of the primary or secondary amine, there can be employed Boc or Cbz. In the case of hydroxy, there can be employed TBS, TES or benzyl. Of course, a precursor substituent may be employed in the reaction steps and later transformed into the desired substituent. For example, where B4 is produced with $R^a$ as nitro, the nitro may be reduced to the amine and the amine may be, for example, alkylated, acylated, diazotized, etc. R' may be selected from suitable protecting groups, including alkyl protecting groups, benzyl protecting group and silyl protecting groups.

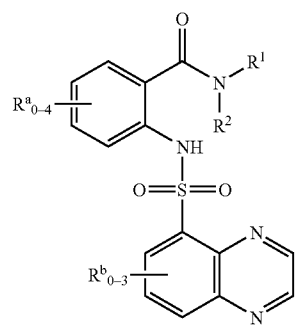

Referring to Scheme C, aniline C1 is sulfonylated to quinoxaline C2. In the case that R" is an ester or cyano, the ester or cyano is hydrolyzed to the acid C3. Acid C3 undergoes peptide coupling under standard conditions with an amine to produce quinoxaline sulfonamide compounds (I). Where $R^a$ or $R^b$ is a primary or secondary amine or hydroxy, it can be protected with common protecting groups. In the case of the primary or secondary amine, there can be employed Boc or Cbz. In the case of hydroxy, there can be employed TBS, TES or benzyl. Of course, a precursor substituent may be employed in the reaction steps and later transformed into the desired substituent. For example, where B4 is produced with $R^a$ as nitro, the nitro may be reduced to the amine and the amine may be, for example, alkylated, acylated, diazotized, etc. R' may be selected from suitable protecting groups, including alkyl protecting groups, benzyl protecting group and silyl protecting groups.

Scheme C

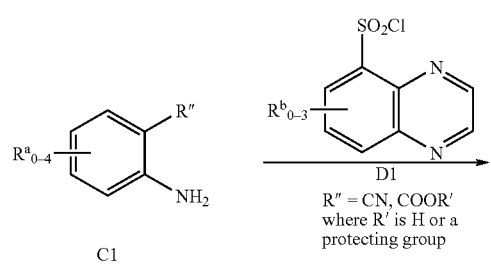

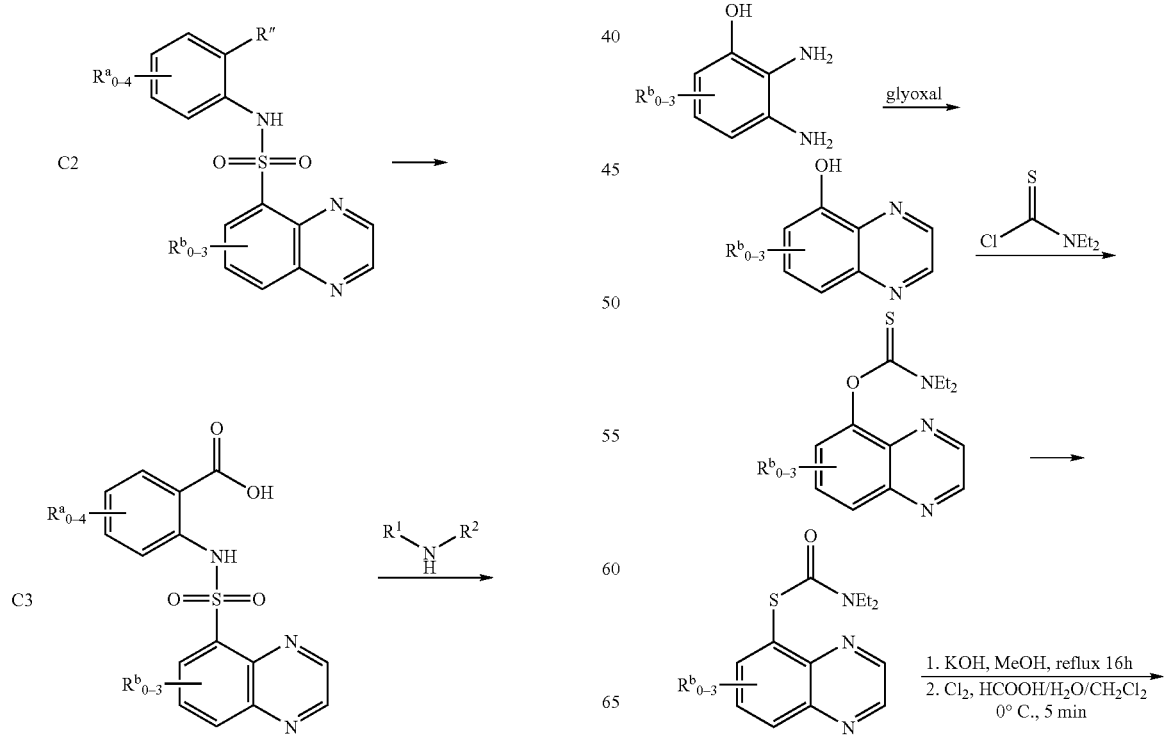

-continued

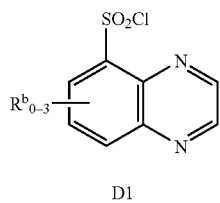

D1

Referring to Scheme D, phenylene diamine is condensed with glyoxal to produce hydroxy quinoxaline. This is followed by acylation with thionocarbamoyl chloride producing a thionocarbamate. The thionocarbamate is isomerized by heating to a thiocarbamate, where good yields are obtained with heating to 240 C for about 45 minutes. Finally, the thiocarbamate is saponified to the corresponding thiol and immediately thereafter oxidized to the sulfonylchloride.

The compounds of the present invention are CCK2 modulators and, as disclosed herein, many are demonstrated CCK2 antagonists. As such, the compounds are useful in the treatment of CCK2 mediated disease states. Particularly, the compounds may be used in the treatment or prevention of pancreatic adenocarcinoma, pain, eating disorders, gastro-esophageal reflux disease, gastroduodenal ulcers, reflux esophagitis, anxiety, colon cancer, peptic ulcers, pancreatic tumors, gastric tumors, Barrett's esophagus, antral G cell hyperplasia, pernicious anaemia and Zollinger-Ellison syndrome. Particularly, CCK2 antagonists are now in development for the treatment or prevention of pancreatic adenocarcinoma, pain, gastro-esophageal reflux disease, gastroduodenal ulcers, reflux esophagitis, anxiety, colon cancer, peptic ulcers, pancreatic tumors and gastric tumors.

It is anticipated that the compounds of the invention can be administered by oral or parenteral routes, including intravenous, intramuscular, intraperitoneal, subcutaneous, rectal and topical administration, and inhalation. For oral administration, the compounds of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate and lactose. Cornstarch and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the active ingredient is mixed with a solid diluent and soft gelatin capsules wherein the active ingredient is mixed with water or an oil such as peanut oil, liquid paraffin or olive oil. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

Gilson® instrument

Column: YMC-Pack ODS-A, 5 μm, 75×30 mm

Flow rate: 10 mL/min

Detection: λ=220 & 254 nm

Gradient (acetonitrile/water, 0.05% trifluoroacetic acid)

1) 0.0 min 20% acetonitrile/80% water 2) 20.0 min 99% acetonitrile/1% water

Protocol for HPLC (Reversed-Phase)

Hewlett Packard Series 1100

Column: Agilent ZORBAX® C8, 5 μm, 4.6×150 mm

Flow rate: 1 mL/min

Detection: λ=220 & 254 nm

Gradient (acetonitrile/water, 0.05% trifluoroacetic acid)

1) 0.0 min 1% acetonitrile/99% water 2) 8.0 min 99% acetonitrile/1% water

Mass spectra were obtained on an Agilent series 1100 MSD using electrospray ionization (ESI) in either positive or negative modes as indicated.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Example 1

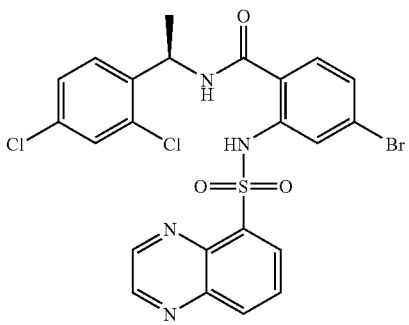

(R)-4-Bromo-N-[1-(2,4-dichlorophenyl)-ethyl]-2-(quinoxaline-5-sulfonylamino)-benzamide.

A. Diethylthiocarbamic acid O-quinoxalin-5-yl ester. A mixture of 5-hydroxyquinoxaline (2.13 g, 14.6 mmol), finely ground $K_2CO_3$ (4.0 g, 29 mmol), and DMF (50 mL) was stirred at 23° C. for 1 h. Solid diethylthiocarbamoyl chloride (2.43 g, 16.1 mmol) was then added in a single portion. The resulting mixture was stirred for 2 h, then was diluted with $H_2O$ (150 mL) and extracted with diethyl ether (2×100 mL). The combined ethereal extracts were washed with $H_2O$ (100 mL) and brine (100 mL), then dried and concentrated to a viscous orange oil, which was used without purification in the subsequent step (3.63 g, 95%). MS (ESI): Calculated for $C_{13}H_{15}N_3OS$, 261.1; found, m/z 262 [M+H]$^+$. $^1$H NMR (500 MHz, CDCl$_3$): 8.85-8.65 (m, 2H), 7.96 (dd, J=8.5, 1.1 Hz, 1H), 7.71 (t, J=7.9 Hz, 1H), 7.46 (dd, J=7.6, 1.18 Hz, 1H), 3.87 (q, J=7.1 Hz, 2H), 3.78 (q, J=7.1 Hz, 2H), 1.38 (t, J=7.1 Hz, 3H), 1.28 (t, J=7.1 Hz, 3H). $^{13}$C NMR (125 MHz, CDCl$_3$): 186.6, 149.4, 144.9, 144.5, 143.4, 137.0, 128.9, 127.0, 123.1, 48.2, 44.5, 13.1, 11.5.

B. Diethylthiocarbamic acid S-guinoxalin-5-yl ester. Neat diethylthiocarbamic acid O-quinoxalin-5-yl ester (0.52 g, 2.0 mmol) was heated to 240° C. for 1 h. The resulting brown oil was chromatographed (20 to 50% EtOAc/hexanes), providing a pale yellow oil (0.49 g, 94%). MS (ESI): Calculated for $C_{13}H_{15}N_3OS$, 261.1; found, m/z 262 [M+H]$^+$. $^1$H NMR (500 MHz, CDCl$_3$): 8.93 (d, J=1.8 Hz, 1H), 8.87 (d, J=1.8 Hz, 1H), 8.18 (dd, J=8.4, 1.2 Hz, 1H), 8.13 (dd, J=7.3, 1.2 Hz, 1H), 7.81 (dd, J=7.3, 1.0 Hz, 1H), 3.61 (br s, 2H), 3.43 (br s, 2H), 1.38 (br s, 3H), 1.16 (br s, 3H).

C. Quinoxaline-5-sulfonyl chloride. A solution of diethylthiocarbamic acid S-quinoxalin-5-yl ester (3.20 g, 12.3 mmol), KOH (6.89 g, 123 mmol) and methanol (100 mL) was heated at reflux for 16 h. The solution was allowed to cool to 23° C., and then AcOH (7 mL) was added. The mixture was diluted with $H_2O$ (100 mL) and extracted with EtOAc (2×100 mL). The combined extracts were washed with $H_2O$ (100 mL) and brine (100 mL), then dried and concentrated to a tan solid (1.90 g). A portion of this thiol (0.22 g, 1.4 mmol) was combined with DCM (50 mL), formic acid (25 mL), and $H_2O$ (25 mL), and the resulting biphasic mixture was cooled to 0° C. Chlorine gas was bubbled through this mixture with rapid stirring for 5 min. The mixture was transferred to a separatory funnel, and the organic phase was collected. The aqueous phase was extracted with DCM (50 mL), and the combined organic phases were washed with 1 M NaOH (50 mL) and brine (50 mL), then dried. The solution was concentrated to afford the titled compound as a light yellow crystalline solid (0.28 g, 86%). $^1$H NMR (500 MHz, CDCl$_3$): 9.17 (d, J=1.8 Hz, 1H), 9.07 (d, J=1.8 Hz, 1H), 8.60 (dd, J=7.5, 1.4 Hz, 1H), 8.53 (dd, J=8.4, 1.4 Hz, 1H), 7.96 (dd, J=8.6, 0.8 Hz, 1H). $^{13}$C NMR (125 MHz, CDCl$_3$): 146.9, 146.8, 143.7, 140.4, 139.0, 138.4, 132.4, 128.8.

D. 4-Bromo-2-nitrobenzoic acid. A mixture of 4-bromo-2-nitrotoluene (5.0 g, 23 mmol), KMnO$_4$ (1 g, 70 mmol), and $H_2O$ (250 mL) was heated at reflux overnight in a 1 L round-bottom flask fitted with a reflux condenser. The brown suspended MnO$_2$ was removed by filtration through a pad of diatomaceous earth. The filter cake was washed with $H_2O$. The basic filtrate was acidified to pH ~1 with concentrated HCl and extracted with EtOAc (3×300 mL). The combined organic layers were dried (MgSO$_4$) and concentrated in vacuo to provide the pure benzoic acid (1.22 g, 22%). MS (ESI) calculated for $C_7H_4BrNO_4$, 244.9; found, m/z 244 [M−H]$^−$. $^1$H NMR (400 MHz, CD$_3$OD): 8.07 (d, J=1.9 Hz, 1H), 7.85 (dd, J=8.2, 1.9 Hz, 1H), 7.65 (d, J=8.2 Hz, 1H).

E. Methyl 2-amino-4-bromobenzoate. To a stirred solution of 4-bromo-2-nitrobenzoic acid (3.8 g, 15 mmol) in DMF (30 mL) at 0° C. was added 1,8-diazabicyclo[5.4.0]undec-7-ene (DBU) (10.0 mL, 75.0 mmol) followed by iodomethane (4.7 mL, 75 mmol). The reaction mixture was stirred 15 min at 0° C., then was allowed to warm to room temperature and was stirred overnight. The mixture was poured into $H_2O$ and extracted with EtOAc (2×). The combined organic extracts were washed with $H_2O$ (2×), dried (MgSO$_4$), and concentrated in vacuo. The residue was purified by flash chromatography (hexanes/EtOAc) to afford methyl 4-bromo-2-nitrobenzoate as a pale yellow solid (3.52 g, 0.90%). To a solution of the nitrobenzoate (3.52 g, 13.5 mmol) in 1:1 EtOAc/DCM (30 mL) at room temperature was added SnCl$_2$.2H$_2$O (15 g, 67 mmol). The reaction mixture was allowed to stir overnight. The solvents were evaporated in vacuo, and the residue was partitioned between satd. aq. NaHCO$_3$ and DCM. The layers were separated, and the aqueous layer was further extracted with DCM (2×). The combined organic layers were dried (MgSO$_4$) and concentrated in vacuo to provide the pure aminobenzoate as a white solid (2.89 g, 93%). $^1$H NMR (400 MHz, CDCl$_3$): 7.70 (d, J=8.6 Hz, 1H), 6.84 (d, J=1.9 Hz, 1H), 6.75 (dd, J=8.6, 1.9 Hz, 1H), 5.78 (br s, 2H), 3.86 (s, 3H).

F. 4-Bromo-2-(quinoxaline-5-sulfonylamino)benzoic acid methyl ester. A solution of quinoxaline-5-sulfonyl chloride (0.50 g, 2.2 mmol), methyl 2-amino-4-bromobenzoate (0.50 g, 2.2 mmol), pyridine (0.87 mL, 11 mmol), and DCM (15 mL) was maintained at 23° C. for 16 h. The reaction mixture was diluted with EtOAc (50 mL) and washed with satd. aq. NaHCO$_3$ (50 mL), then dried and concentrated. The residue was purified by flash chromatography (5 to 40% EtOAc/hexanes) to afford the sulfonamide as a white solid (0.78 g, 84%). MS (ESI) calculated for $C_{16}H_{12}BrN_3O_4S$, 421.0; found, m/z 422 [M+H]$^+$. $^1$H NMR (500 MHz, CDCl$_3$): 11.39 (s, 1H), 8.96 (d, J=1.7 Hz, 1H), 8.94 (d, J=1.7 Hz, 1H), 8.61 (dd, J=7.4, 1.4 Hz, 1H), 8.33 (dd J=8.5, 1.4 Hz, 1H), 8.02 (d, J=1.9 Hz, 1H), 7.89 (dd, J=8.4, 1.0 Hz, 1H), 7.69 (d, J=8.5, 1H), 7.06 (dd, J=8.5, 1.9 Hz, 1H), 3.90 (s, 3H).

G. 4-Bromo-2-(quinoxaline-5-sulfonylamino)benzoic acid. A solution of LiOH.H$_2$O (0.36 g, 8.6 mmol) in $H_2O$ (5 mL) was added to a solution of 4-bromo-2-(quinoxaline-5-sulfonylamino)benzoic acid methyl ester (0.73 g, 1.7 mmol) and THF (10 mL), and the biphasic mixture was rapidly stirred for 16 h. The mixture was concentrated to a volume of 5 mL, and then was adjusted to pH 5 with 1 M HCl. The resulting precipitate was collected by filtration, providing the acid as a white solid (0.68 g, 96%). MS (ESI) calculated for $C_{15}H_{10}BrN_3O_4S$, 407.0; found, m/z 408 [M+H]+. $^1$H NMR (500 MHz, CDCl$_3$): 14.1 (br s, 1H), 9.11 (d, J=1.4 Hz, 1H), 8.99 (d, J=1.4 Hz, 1H), 8.63 (d, J=7.4 Hz, 1H), 8.42 (d, J=8.4 Hz, 1H), 8.06 (t, J=8.3 Hz, 1H), 7.77 (d, J=1.6 Hz, 1H), 7.71 (d, J=8.5 Hz, 1H), 7.20 (dd, J=8.5, 1,6 Hz, 1H).

H. S-(S)-2-Methyl-propane-2-sulfinic acid 2,4-dichloro-benzylideneamide. A suspension of 2,4-dichlorobenzaldehyde (0.75 g, 4.3 mmol), (S)-tert-butanesulfinamide (0.47 g, 3.9 mmol), and powdered anhydrous CuSO$_4$ (1.2 g, 7.8 mmol) in DCM (8 mL) was stirred overnight. The reaction mixture was filtered, and the filter cake was washed with DCM. The filtrate was concentrated in vacuo to give the crude N-sulfinyl imine as white solid. Purification by flash chromatography (EtOAc/hexanes) provided 0.97 g (90%) of the N-sulfinyl imine as a white solid. $^1$H NMR (400 MHz, CDCl$_3$): 8.98 (s, 1H), 8.01 (d, J=8.5 Hz, 1H), 7.48 (d, J=2.1 Hz, 1H), 7.35-7.32 (m, 1H), 1.27 (s, 9H).

I. S-(S)-2-Methyl-propane-2-sulfinic acid 1-(R)-[1-(2,4-dichloro-Phenyl)-ethyl]-amide. To a stirred solution of the above N-sulfinyl imine (0.97 g, 3.5 mmol) in DCM (20 mL) at −50° C. was added a solution of methyl magnesium bromide (3.0 M in diethyl ether, 2.3 mL, 6.9 mmol). The reaction mixture was stirred at −50° C. for 1 h then allowed to warm slowly to room temperature overnight. The reaction was quenched by the addition of satd. aq. NH$_4$Cl, and the mixture was poured into H$_2$O and extracted with DCM (3×). The combined organic layers were dried (Na$_2$SO$_4$) and concentrated in vacuo. Purification by flash chromatography (EtOAc/hexanes) provided the title compound as a colorless solid (1.02 g, 99%, 76% de). Major diastereomer: $^1$H NMR (400 MHz, CDCl$_3$): 7.43-7.35 (m, 2H), 7.26-7.23 (m, 1H), 5.01 (dq, J=6.7, 4.0 Hz, 1H), 3.39 (d, J=3.7 Hz, 1H), 1.53 (d, J=6.7 Hz, 3H), 1.21 (s, 9H).

J. (R)-1-(2,4-Dichlorophenyl)-ethylamine hydrochloride. To a stirred solution of the above sulfinamide (76% de, 1.02 g, 3.47 mmol) in 7:4 methanol/DCM (11 mL) at room temperature was added 2 mL of a satd. solution of HCl (g) in methanol. After several minutes, precipitated amine hydrochloride was visible. The reaction mixture was allowed to stir for 2 h at room temperature. The heterogeneous mixture was concentrated in vacuo until approximately 2 mL remained, and then the amine hydrochloride was fully precipitated by the addition of diethyl ether (10 mL). The HCl salt was collected by suction filtration, washed with diethyl ether, and dried in vacuo to give fine white crystals (722 mg, 92%, 76% ee). $^1$H NMR (400 MHz, CD$_3$OD): 7.62 (d, J=2.2 Hz, 1H), 7.57 (d, J=8.4 Hz, 1H), 7.50 (dd, J=8.4, 2.2 Hz, 1H), 1.62 (d, J=6.8 Hz, 3H).

K. (R)-4-Bromo-N-[1-(2,4-dichlorophenyl)-ethyl]-2-(quinoxaline-5-sulfonylamino)-benzamide. To a solution of 4-bromo-2-(quinoxaline-5-sulfonylamino)benzoic acid (0.021 g, 0.051 mmol) in a mixture of THF (0.08 mL) and DMF (0.40 mL) at room temperature was added pyridine (0.012 mL, 0.15 mmol) followed by O-(7-azabenzotriazol-1-yl)-N,N,N',N'-tetramethyluronium hexafluorophosphate (HATU) (0.038 g, 0.12 mmol). The reaction mixture was agitated for 1 h on a shaker. (R)-1-(2,4-Dichlorophenyl)-ethylamine hydrochloride (0.038 g, 0.10 mmol) and N,N-diisopropylethylamine (Hünig's base) (0.017 mL, 0.10 mmol) were added. The reaction mixture was agitated for 1 h. TFA (0.050 mL) was added to quench the reaction. The mixture was diluted with DMF (1 mL), and the product amide was obtained by purification of the resulting mixture by preparative reverse-phase chromatography. The title amide was obtained as a solid (24 mg, 83%). MS (ESI): mass calculated for $C_{23}H_{17}BrCl_2N_4O_3S$, 577.96; m/z found, 577/579/581 [M−H]−. HPLC (reverse phase): R$_T$=10.34 min. $^1$H NMR (500 MHz, CDCl$_3$): 11.32 (s, 1H), 8.85(d, J=1.8 Hz, 1H), 8.76 (d, J=1.8 Hz, 1H), 8.55 (dd, J=7.4, 1.4 Hz, 1H), 8.31 (dd, J=7.4, 1.4 Hz, 1H), 7.94 (d, J=1.8 Hz, 1H), 7.87 (dd, J=8.4, 7.4 Hz, 1H), 7.44 (d, J=1.7 Hz, 1H), 7.35-7.15 (m, 3H), 7.09 (dd, J=8.4, 1.8 Hz, 1H), 6.36 (br d, J=6.5 Hz, 1H), 5.49-5.30 (m, 1H), 1.52 (d, J=7.0 Hz, 3H).

Example 2

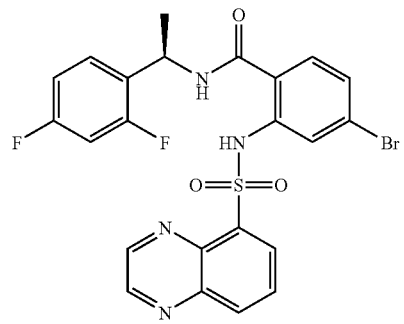

(R)-4-Bromo-N-[1-(2,4-difluoro-phenyl)-ethyl]-2-(quinoxaline-5-sulfonylamino)-benzamide.

Method 1.

A. S—(S)-2-Methylpropane-2-sulfinic acid 2,4-difluorobenzylideneamide. A suspension of 2,4-difluorobenzaldehyde (0.61 g, 4.3 mmol), (S)-tert-butanesulfinamide (0.47 g, 3.9 mmol), and powdered anhydrous CuSO$_4$ (1.24 g, 7.8 mmol) was stirred in DCM (8 mL) overnight. The reaction mixture was filtered, and the filter cake was washed with DCM. The filtrate was concentrated in vacuo to give the crude N-sulfinyl imine as a viscous yellow oil. Purification by flash chromatography (EtOAc/hexanes) provided 0.81 g (84%) of the N-sulfinyl imine as a pale yellow viscous oil. $^1$H NMR (400 MHz, CDCl$_3$): 8.83 (s, 1H), 8.05-7.99 (m, 1H), 7.01-6.96 (m, 1H), 6.94-6.87 (m, 1H), 1.27 (s, 9H).

B. S—(S)—2-Methylpropane-2-sulfinic acid 1-(R)-[1-(2,4-difluorophenyl)-ethyl]-amide. To a stirred solution of S—(S)-2-methylpropane-2-sulfinic acid 2,4-difluorobenzylideneamide (0.77 g, 3.1 mmol) in DCM (20 mL) at −50° C., was added a solution of methyl magnesium bromide (3.0 M in diethyl ether, 2.1 mL, 6.3 mmol). The reaction mixture was stirred at −50° C. for 1 h then allowed to warm slowly to room temperature overnight. The reaction was quenched by the addition of satd. aq. NH$_4$Cl, and the mixture was poured into H$_2$O, and extracted with DCM (3×). The combined organic layers were dried (Na$_2$SO$_4$) and concentrated in vacuo. Purification by flash chromatography (EtOAc/hexanes) provided the title compound as a colorless, viscous oil (0.80 g, 99%, 90% de). Major diastereomer: $^1$H NMR (400 MHz, CDCl$_3$): 7.37-7.28 (m, 1H), 6.88-6.83 (m, 1H), 6.82-6.76 (m, 1H), 4.82 (dq, J=6.8, 4.5 Hz, 1H), 3.32 (d, J=4.1 Hz, 1H), 1.56 (d, J=6.8 Hz, 3H), 1.19 (s, 9H).

C. (R)-1-(2,4-Difluorophenyl)ethylamine hydrochloride. To a stirred solution of S—(S)-2-methylpropane-2-sulfinic acid 1-(R)-[1-(2,4-difluorophenyl)-ethyl]-amide (0.80 g, 3.1 mmol, 90% de) in methanol (7 mL) at room temperature, was added 2 mL of a satd. solution of HCl (g) in methanol. After several minutes, precipitated amine hydrochloride was visible. The reaction mixture was allowed to stir for 2 h at room temperature. The heterogeneous mixture was concentrated in vacuo until approximately 2 mL remained, and then the amine hydrochloride was fully precipitated by the addition of diethyl ether (10 mL). The HCl salt was collected by suction filtration, washed with diethyl ether, and dried in vacuo to provide fine white crystals (570 mg, 95%, 99% ee). Enantiomeric purity was determined by HPLC analysis on the benzamide derivative of the amine. Chiralcel AS column, 90:10 hexanes/isopropyl alcohol, 0.7 mL/min. R enantiomer, $R_T$=18.1 min. S enantiomer, $R_T$=21.0 min. $[\alpha]_D^{20}$=−3.7° (c 4.37, $H_2O$). $^1$H NMR (400 MHz, $CD_3OD$): 7.60-7.53 (m, 1H), 7.14-7.06 (m, 2H), 4.72 (q, J=7.0 Hz, 1H), 1.65 (d, J=6.8 Hz, 3H).

D. (R)-4-Bromo-N-[1-(2,4-difluorophenyl)ethyl]-2-(quinoxaline-5-sulfonylamino)-benzamide. 4-Bromo-2-(quinoxaline-5-sulfonylamino)benzoic acid (EXAMPLE 1, Step G; 21 mg, 0.052 mmol) was coupled with (R)-1-(2,4-difluoro-phenyl)ethylamine hydrochloride (27 mg, 0.14 mmol) according to the general procedure described in EXAMPLE 1, Step K to provide the desired amide (24 mg, 89%). mp=200-200.5° C.; MS (ESI): mass calculated for $C_{23}H_{17}BrF_2N_4O_3S$, 546.0; m/z found, 547/549 [M+H]$^+$. HPLC (reverse phase): $R_T$=9.76 min. Anal. calcd. for $C_{23}H_{17}BrF_2N_4O_3S$: C, 50.47; H, 3.13; N 10.24, S 5.86; found: C 50.10, H 3.18, N 10.06, S 5.88. $^1$H NMR (500 MHz, $CDCl_3$): 11.33 (s, 1H), 8.83 (d, J=1.8 Hz, 1H), 8.78 (d, J=1.8 Hz, 1H), 8.55 (dd, J=7.4, 1.4 Hz, 1H), 8.30 (dd, J=7.4, 1.4 Hz, 1H), 7.92 (d, J=1.8 Hz, 1H), 7.86 (dd, J=8.4, 7.4 Hz, 1H), 7.30 (dd, J=8.5, 2.2 Hz, 1H), 7.16 (d, J=8.4, 1H), 7.08 (dd, J=8.4, 1.8 Hz, 1H), 6.92-6.80 (m, 2H), 6.33 (br d, J=6.5 Hz, 1H), 5.31 (quint, J=7.5 Hz, 1H), 1.53 (d, J=7.0 Hz, 3H).

Alternatively, the title compound can be prepared via the following procedure:

Method 2.

A. (R)-4-Bromo-N-[1-(2,4-difluorophenyl)ethyl]-2-nitrobenzamide. A suspension of 4-bromo-2-nitrobenzoic acid (EXAMPLE 1, Step G; 8.0 g, 32 mmol) in thionyl chloride (25 mL) was heated at reflux for 30 min. The reaction became homogeneous. The mixture was cooled to room temperature and concentrated in vacuo to provide the acid chloride as a yellow liquid. The liquid was re-concentrated from DCM (3×) to ensure complete removal of thionyl chloride. $^1$H NMR (400 MHz, $CDCl_3$): 8.20 (d, J=1.9 Hz, 1H), 7.92 (dd, J=8.3, 1.9 Hz, 1H), 7.65 (d, J=8.3 Hz, 1H). To a solution of the acid chloride (32.5 mmol) in DCM (60 mL) at 0° C. was added (R)-1-(2,4-difluorophenyl)-ethylamine hydrochloride (6.61 g, 34.1 mmol) and Hünig's base (14 mL, 81 mmol). The mixture was allowed to warm to room temperature and was stirred for 1 h. The reaction mixture was washed twice with 1 N HCl, and each aqueous wash was back-extracted with DCM. The combined organic layers were dried ($Na_2SO_4$) and concentrated in vacuo to give the desired amide as a pale yellow solid (12.3 g, 98%). HPLC (reverse phase): $R_T$=9.190 min. $^1$H NMR (500 MHz, $CDCl_3$): 8.20 (d, J=1.8 Hz, 1H), 7.79 (dd, J=8.1, 1.8 Hz, 1H), 7.35 (ddd, J=8.6, 8.6, 6.3 Hz, 1H), 6.91-6.85 (m, 2H), 6.20 (br d, J=6.7 Hz, 1H), 5.38 (quint, J=7.5 Hz, 1H), 1.61 (d, J=7.0 Hz, 3H).

B. (R)-2-Amino-4-bromo-N-[1-(2,4-difluorphenyl)ethyl]-benzamide. To a stirred solution of (R)$_4$-bromo-N-[1-(2,4-difluorophenyl)-ethyl]-2-nitro-benzamide (12.3 g, 32.0 mmol) in 1:1 DCM/EtOAc (400 mL) at room temperature was added $SnCl_2.2H_2O$ (29.0 g, 128 mmol). A mild exotherm was observed as the tin chloride slowly dissolved. The mixture was stirred for 14 h at room temperature. The reaction mixture was made basic by the addition of satd. $NaHCO_3$ (800 mL), causing precipitation of tin salts. Diatomaceous earth (30 g) was added and the slurry was mixed thoroughly. The mixture was filtered through a pad of diatomaceous earth, washing with excess EtOAc. The biphasic filtrate was separated, and the aqueous layer was extracted once with EtOAc. The combined organic layers were dried ($Na_2SO_4$) and concentrated to give the desired aminobenzamide as a pale yellow solid (11.1 g, 98%). TLC (silica, 66% EtOAc/hexanes): $R_f$=0.39. HPLC (reverse phase): $R_T$=9.461 min. $^1$H NMR (500 MHz, $CDCl_3$): 7.30 (ddd, J=8.6, 8.6, 6.4 Hz, 1H), 7.17 (d, J=8.4 Hz, 1H), 6.90-6.78 (m, 3H), 6.75 (dd, J=8.4, 1.8 Hz, 1H), 6.35 (br d, J=7.0 Hz, 1H), 5.60 (br s, 2H), 5.34 (quint, J=7.2 Hz, 1H), 1.57 (d, J=7.00 Hz, 3H).

C. (R)-2-(Benzo[1,2,5]thiadiazole-4-sulfonylamino)-4-bromo-N-[1-(2,4-difluoro-phenyl)ethyl]-benzamide. To a solution of (R)-2-amino-4-bromo-N-[1-(2,4-difluoro-phenyl)-ethyl]-benzamide (11.1 g, 31.2 mmol) and benzo[1,2,5]thiadiazole-4-sulfonyl chloride (11 g, 44 mmol) in DCM (100 mL) at 0° C. was added pyridine (12.6 mL, 156 mmol) slowly via syringe. The resulting orange mixture was allowed to stir for 16 h at room temperature then was washed with 1 N HCl (2×100 mL). Each aqueous wash was back-extracted with DCM. The combined organic layers were dried ($Na_2SO_4$) and concentrated to give the crude sulfonamide. The crude tan solid was purified by trituration with diethyl ether (300 mL). The product was collected by suction filtration, washed with additional diethyl ether, and dried in vacuo to provide the pure sulfonamide as a tan solid (15.3 g, 88%). MS (ESI): mass calculated for $C_{21}H_{15}BrF_2N_4O_3S_2$, 552.0; m/z found, 553 [M+H]$^+$. HPLC (reverse phase): $R_T$=10.17 min. $^1$H NMR (500 MHz, $CDCl_3$): (rotameric broadening) 11.52 (s, 1H), 8.35 (dd, J=7.0, 1.0 Hz, 1H), 8.20 (dd, J=8.8, 1.0 Hz, 1H), 70 (d, J=1.8 Hz, 1H), 7.70 (dd, J=8.8, 7.0 Hz, 1H), 7.31 (dt, J=8.4, 6.2 Hz, 1H), 7.16 (d, J=8.4 Hz, 1H), 7.10 (dd, J=8.4, 1.8 Hz, 1H), 6.92-6.80 (m, 2H), 6.37 (d, J=7.6 Hz, 1H), 5.33 (quint, J=7.5 Hz, 1H), 1.56 (d, J=7.0 Hz, 3H).

D. (R)-4-Bromo-N-[1-(2,4-difluorophenyl)-ethyl]-2-(quinoxaline-5-sulfonylamino)-benzamide. To a solution of (R)-2-(benzo[1,2,5]thiadiazole-4-sulfonylamino)-4-bromo-N-[1-(2,4-difluorophenyl)ethyl]benzamide (15.3 g, 27.6 mmol) in ACOH (200 mL) at 50° C. was added zinc dust (18.0 g, 275 mmol) in small portions. After addition was complete, the reaction was stirred at 50° C. for 2 h. The reaction mixture was filtered through a pad of diatomaceous earth with excess methanol. The filtrate was concentrated in vacuo to provide the reduced phenylene diamine as a yellow-orange heterogeneous mixture containing zinc salts and AcOH. HPLC (reverse phase): $R_T$ 9.15 min (single peak). The unpurified mixture was combined with glyoxal bisulfite adduct (22 g, 83 mmol), NaOAc (2.3 g, 28 mmol), $H_2O$ (80 mL), ACOH (12 mL), and methanol (240 mL) and heated at reflux for 4 h. The dark orange suspension was filtered through a pad of diatomaceous earth and washed with excess DCM (~1.5 L). The filtrate was concentrated in vacuo and partitioned between $H_2O$ and DCM. The layers were separated, and the aqueous layer was extracted with DCM (4×). The combined organic layers were dried (Na$_2$SO$_4$) and concentrated to give a dark orange oil. The oil was passed through a plug of silica gel and eluted with a mixture of EtOAc/hexanes (gradient from 30 to 70%), and then was triturated with methanol to provide the title compound as a dark tan solid (8.80 g, 58%).

Example 3

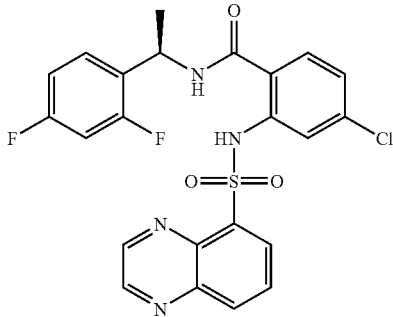

(R)-4-Chloro-N-[1-(2,4-difluorophenyl)-ethyl]-2-(quinoxaline-5-sulfonylamino)-benzamide.

A. 4-Chloro-2-(Quinoxaline-5-sulfonylamino)benzoic acid methyl ester. A solution of methyl 2-amino-4-chlorobenzoate (0.33 g, 1.8 mmol), quinoxaline-5-sulfonyl chloride (0.40 g, 1.8 mmol), pyridine (0.71 mL, 8.8 mmol), and DCM (10 mL) was maintained at 23° C. for 16 h. EtOAc (75 mL) was added and the solution was washed with satd. aq. NaHCO$_3$ (50 mL), then dried and concentrated to a solid. Chromatographic purification of this residue (3 to 40% EtOAc/hexanes) delivered the titled compound as a white solid (0.60 mg, 90%). MS (ESI): mass calculated for C$_{16}$H$_{12}$ClN$_3$O$_4$S, 377.0; m/z found, 378 [M+H]$^+$. $^1$H NMR (400 MHz, CDCl$_3$): 11.44 (s, 1H), 8.97 (d, J=1.8 Hz, 1H), 8.95 (d, J=1.8 Hz, 1H), 8.61 (dd, J=7.4, 1.4 Hz, 1H), 8.33 (dd, J=8.5, 1.4 Hz, 1H), 7.89 (dd, J=8.4, 1.0 Hz, 1H), 7.84 (d, J=2.0 Hz, 1H), 7.77 (d, J=8.6 Hz, 1H), 6.89 (dd, J=8.6, 2.0 Hz, 1H), 3.90 (s, 3H).

B. 4-Chloro-2-(Quinoxaline-5-sulfonylamino)benzoic acid. A solution of LiOH·H$_2$O (0.32 g, 7.7 mmol) in H$_2$O (5 mL) was added to a solution of 4-chloro-2-(quinoxaline-5-sulfonylamino)benzoic acid methyl ester (0.58 g, 1.5 mmol) and THF (10 mL). The biphasic mixture was stirred rapidly at 23° C. for 16 h, then adjusted to pH 5 with 1 M HCl. The resulting precipitate was collected by filtration to afford the acid as a white solid (0.51 g, 92%). MS (ESI): calculated for C$_{15}$H$_{10}$ClN$_3$O$_4$S, 363.0; m/z found, 364 [M+H]$^+$. $^1$H NMR (500 MHz, DMSO-d$_6$): 14.20 (br s, 1H), 11.73 (s, 1H), 9.12 (d, J=1.6 Hz, 1H), 9.00 (d, J=1.5 Hz, 1H), 8.65 (d, J=7.3 Hz, 1H), 8.42 (d, J=8.3 Hz, 1H), 8.06 (t, J=7.8 Hz, 1H), 7.80 (d, J=8.5 Hz, 1H), 7.63 (d, J=2.0 Hz, 1H), 7.07 (dd, J=8.4, 1.9 Hz, 1H).

C. (R)-4-Chloro-N-[1-(2,4-difluorophenyl)ethyl]-2-(quinoxaline-5-sulfonylamino)-benzamide. The title compound was prepared and purified by the HATU-mediated coupling of 4-chloro-2-(quinoxaline-5-sulfonylamino)benzoic acid and (R)-1-(2,4-difluorophenyl)ethylamine hydrochloride (EXAMPLE 2, Method 1, Step C) as described by the general procedure in EXAMPLE 1, Step K. MS (ESI): mass calculated for C$_{23}$H$_{17}$ClF$_2$N$_4$O$_3$S, 502.1; m/z found, 501 [M−H]$^-$. HPLC (reverse phase): R$_T$=9.75 min. $^1$H NMR (500 MHz, CDCl$_3$): 11.34 (s, H), 8.84 (d, J=1.8 Hz, 1H), 8.80 (d, J=1.8 Hz, 1H), 8.57 (dd, J=7.4, 1.4 Hz, 1H), 8.31 (dd, J=7.4, 1.4 Hz, 1H), 7.86 (dd, J=8.4, 7.4 Hz, 1H), 7.77 (d, J=2.0 Hz, 1H), 7.35-7.25 (m, 1H), 7.22-7.19 (m, 1H), 7.08 (dd, J=8.4, 1.8 Hz, 1H), 6.93-6.87 (m, 2H), 6.34 (br d, J=6.5 Hz, 1H), 5.35-5.25 (m, 1H), 1.54 (d, J=7.0 Hz, 3H).

Example 4

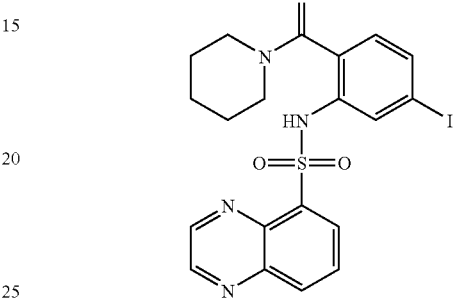

Quinoxaline-5-sulfonic acid [5-iodo-2-(piperidine-1-carbonyl)-phenyl]-amide.

A. 4-Iodo-2-nitrobenzoic acid. 4-Iodo-2-nitrotoluene (9.0 g, 34 mmol), KMnO$_4$ (22.0 g, 139 mmol), and H$_2$O (340 mL) were heated at reflux for 5 h. The resulting brown suspension was filtered through a pad of diatomaceous earth, and the filter cake was washed with H$_2$O. The basic filtrate was acidified with concentrated HCl causing precipitation of the desired acid. The solid was collected by suction filtration and dried, affording 1.86 g of the acid. The mother liquor was extracted with DCM (3×200 mL), and the combined extracts were dried (Na$_2$SO$_4$) and concentrated in vacuo to afford an additional 0.16 g of the benzoic acid (total 2.02 g, 20%). $^1$H NMR (400 MHz, CD$_3$OD): 8.13 (d, J=1.6 Hz, 1H), 8.01 (dd, J=8.1, 1.6 Hz, 1H), 7.50 (d, J=8.1 Hz, 1H).

B. Methyl 2-amino-4-iodobenzoate. To a stirred solution of 4-iodo-2-nitrobenzoic acid (2.3 g, 7.9 mmol) in DMF (30 mL) at 0° C. was added DBU (2.4 mL, 16 mmol) followed by iodomethane (1.5 mL, 24 mmol). The reaction mixture was stirred 15 min at 0° C., then was allowed to warm to room temperature and was stirred overnight. The mixture was poured into H$_2$O and extracted with EtOAc (2×). The combined organic extracts were washed with H$_2$O (2×), dried (MgSO$_4$), and concentrated in vacuo. The residue was purified by flash chromatography (hexanes/EtOAc) to afford methyl 4-iodo-2-nitrobenzoate as a pale yellow solid (2.30 g, 95%). To a solution of the nitrobenzoate (2.3 g, 7.4 mmol) in 1:1 EtOAc/DCM (10 mL) at room temperature was added SnCl$_2$·2H$_2$O (8.3 g, 37 mmol). The reaction mixture was allowed to stir overnight. The solvents were evaporated in vacuo, and the residue was partitioned between satd. aq. NaHCO$_3$ and DCM. The layers were separated, and the aqueous layer was further extracted with DCM (2×). The combined organic layers were dried (MgSO$_4$) and concentrated in vacuo to provide the pure aminobenzoate as a yellow solid (1.87 g, 91%). $^1$H NMR (500 MHz, CDCl$_3$): 7.52 (d, J=8.5 Hz, 1H), 7.07 (d, J=1.6 Hz, 1H), 6.96 (dd, J=8.5, 1.6 Hz, 1H), 5.72 (br s, 2H), 3.86 (s, 3H).

C. 4-Iodo-2-(Quinoxaline-5-sulfonylamino)benzoic acid methyl ester. A solution of methyl 2-amino-4-iodobenzoate (1.2 g, 4.4 mmol), quinoxaline-5-sulfonyl chloride (1.2 g, 5.3 mmol), pyridine (1.7 mL, 22 mmol) and DCM (25 mL) was maintained at 23° C. for 24 h. The reaction mixture was diluted with DCM (200 mL) and washed with satd. aq. NaHCO$_3$, then dried and concentrated to a tan solid. This residue was chromatographed (0 to 100% EtOAc/CH$_2$Cl$_2$) to afford the sulfonamide as a light yellow solid (1.6 g, 77%). MS (ESI): calculated for C$_{16}$H$_{12}$IN$_3$O$_4$S, 469.0; m/z found, 470 [M+H]$^+$. $^1$H NMR (500 MHz, DMSO-d$_6$): 11.10 (s, 1H), 9.07 (d, J=1.8 Hz, 1H), 9.01 (d, J=1.8 Hz, 1H), 8.60 (dd, J=7.4, 1.3 Hz, 1H), 8.40 (dd, J=8.5, 1.3 Hz, 1H), 8.04 (dd, J=7.5, 1.0 Hz, 1H), 7.99 (d, J=1.6 Hz, 1H), 7.51 (d, J=8.3 Hz, 1H), 7.37 (dd, J=8.3, 1.6 Hz, 1H), 3.88 (s, 3H).

D. 4-Iodo-2-(Quinoxaline-5-sulfonylamino)benzoic acid. A solution of LiOH·H$_2$O (0.16 g, 3.9 mmol) in H$_2$O (5 mL) was added to a solution of 4-iodo-2-(quinoxaline-5-sulfonylamino)benzoic acid methyl ester (0.37 mg, 0.78 mmol) and THF (10 mL), and the mixture was rapidly stirred for 16 h. The mixture was concentrated to a volume of 5 mL, then was adjusted to pH 5 with 1 M HCl. The resulting precipitate was collected by filtration to provide the acid as a white solid (0.35 g, 99%). MS (ESI): calculated for C$_{15}$H$_{10}$IN$_3$O$_4$S, 455.0; m/z found, 456 [M+H]$^+$. $^1$H NMR (500 MHz, DMSO-d$_6$): 14.0 (br s, 1H), 11.6 (s, 1H), 9.10 (d, J=1.5 Hz, 1H), 9.97 (d, J=1.5 Hz, 1H), 8.60 (d, J=7.4 Hz, 1H), 8.42 (d, J=8.4 Hz, 1H), 8.06 (t, J=7.5 Hz, 1H), 7.95 (d, J=1.2 Hz, 1H), 7.51 (d, J=8.3 Hz, 1H), 7.37 (dd, J=8.3, 1.2 Hz, 1H).

E. Quinoxaline-5-sulfonic acid [5-iodo-2-(piperidine-1-carbonyl)-phenyl]-amide

The title compound was prepared and purified by the HATU-mediated coupling of 4-iodo-2-(quinoxaline-5-sulfonylamino)benzoic acid and piperidine as described by the general procedure in EXAMPLE 1, Step K. MS (ESI): mass calculated for C$_{20}$H$_{19}$IN$_4$O$_3$S, 522.0; m/z found, 521 [M−H]$^−$. HPLC (reverse phase): R$_T$=9.53 min. $^1$H NMR (500 MHz, CDCl$_3$, rotameric broadening): 9.07 (d, J=1.8 Hz, 1H), 9.00 (d, J=1.8 Hz, 1H), 8.98 (br s, 1H), 8.48 (dd, J=7.0, 1.48 Hz, 1H), 8.35 (dd, J=8.4, 1.4 Hz, 1H), 8.02 (d, J=1.5 Hz, 1H), 7.87 (dd, J=8.4, 7.4 Hz, 1H), 7.37 (dd, J=8.0, 1.6 Hz, 1H), 6.74 (d, J=8.0 Hz, 1H), 3.45-3.05 (br m, 2H), 2.90-2.80 (br m, 2H), 1.50-1.30 (br m, 6H).

Example 5

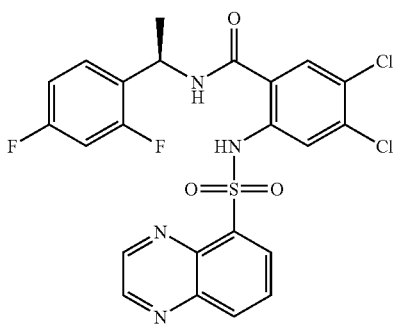

(R)-4,5-Dichloro-N-[1-(2,4-difluorophenyl)ethyl]-2-(quinoxaline-5-sulfonylamino)-benzamide.

A. 4,5-Dichlorophthalic acid monomethyl ester. To a stirred suspension of 4,5-dichlorophthalic anhydride (15.0 g, 69.1 mmol) in methanol (1 L) was added sodium methoxide (5.40 g, 100 mmol). The mixture was heated at reflux for 12 h becoming homogeneous. The reaction mixture was cooled to room temperature and concentrated in vacuo to a volume of ~100 mL, and then was poured into 0.5 N HCl (1 L) causing precipitation of the product. The resulting white powder was collected by suction filtration, washed with H$_2$O, and dried in vacuo to give 17.1 g (99.5%) of the monomethyl ester. $^1$H NMR (400 MHz, CDCl$_3$): 8.02 (s, 1H), 7.84 (s, 1H), 3.94 (s, 3H).

B. Methyl 2-amino-4,5-dichlorobenzoate. A suspension of 4,5-dichlorophthalic acid monomethyl ester (17 g, 69 mmol) in thionyl chloride (100 mL) was heated at reflux for 1 h. The resulting homogeneous mixture was cooled and concentrated in vacuo to give a yellow oil. The oil was azeotroped in vacuo with toluene (5×5 mL) to remove any remaining thionyl chloride, leaving the acid chloride as a yellow liquid. $^1$H NMR (400 MHz, CDCl$_3$): 7.96 (s, 1H), 7.82 (s, 1H), 3.95 (s, 3H). The crude acid chloride was stirred in dry acetone (400 mL) at 0° C. as a solution of NaN$_3$ (18.0 g, 277 mmol) in H$_2$O (120 mL) was added dropwise, maintaining the temperature below 10° C. After addition was complete, the orange reaction mixture was stirred 1 h at 0° C. The mixture was concentrated in vacuo with no external heating. The residue was partitioned between H$_2$O and DCM. The layers were separated and the aqueous phase was extracted with DCM. The combined organic layers were dried (Na$_2$SO$_4$) and concentrated to give the crude acyl azide as a tan solid. $^1$H NMR indicated the acyl azide methyl ester was contaminated with 3 other minor unidentified components. $^1$H NMR (400 MHz, CDCl$_3$): 7.87 (s, 1H), 7.78 (s, 1H), 3.94 (s, 3H). The crude tan solid was suspended in a mixture of acetic acid (240 mL) and H$_2$O (120 mL) and heated to reflux for 1 h. Rapid gas evolution occurred. The resulting suspension was concentrated in vacuo, and the solid was collected by suction filtration and washed with water. The desired methyl 2-amino-4,5-dichlorobenzoate was partially purified by stirring the crude solid in toluene and removing the insoluble material by filtration. The filtrate was concentrated to a white solid which was enriched in methyl 2-amino-4,5-dichlorobenzoate (9.10 g, ~54%, 91% pure) The aminobenzoate was used without further purification. $^1$H NMR (400 MHz, CDCl$_3$): 7.92 (s, 1H), 6.78 (s, 1H), 5.77 (br s, 2H), 3.87 (s, 3H).

C. 4,5-Dichloro-2-(quinoxaline-5-sulfonylamino)benzoic acid methyl ester. Methyl 2-amino-4,5-dichlorobenzoate (60 mg, 0.27 mmol), quinoxaline-5-sulfonyl chloride (EXAMPLE 1, Step C; 0.10 g, 0.44 mmol), and pyridine (0.6 mL, 7 mmol) were combined in toluene (0.5 mL) and heated at 60° C. for 1 h. The mixture was cooled, poured into 1 N HCl, and extracted with with DCM (3×). The combined organic layers were dried (Na$_2$SO$_4$) and concentrated. The residue was purified by flash chromatography (EtOAc/hexanes) to provide 17 mg (15%) of the desired sulfonamide as a colorless solid. $^1$H NMR (400 MHz, CDCl$_3$): 11.29 (br s, 1H), 8.96 (br s, 2H), 8.60 (dd, J=7.2, 1.2 Hz, 1H), 8.35 (dd, J=8.4, 1.2 Hz, 1H), 8.00 (s, 1H), 7.92 (s, 1H), 7.90 (dd, J=8.8, 7.6 Hz, 1H), 3.91 (s, 3H).

D. 4,5-Dichloro-2-(quinoxaline-5-sulfonylamino)benzoic acid. A mixture of 4,5-dichloro-2-(quinoxaline-5-sulfonylamino)benzoic acid methyl ester (17 mg, 0.041 mmol), LiOH (2.0 M in H$_2$O, 0.25 mL, 0.50 mmol), and THF (5 mL) was stirred for 5 h at room temperature. The resulting yellow biphasic mixture was poured into 1 N HCl and extracted with DCM (4×). The combined organic layers were dried (Na₂SO₄) and concentrated to give the pure acid as a tan solid (16 mg, 100%).

E. (R)-4,5-Dichloro-N-[1-(2,4-difluorophenyl)-ethyl]-2-(Quinoxaline-5-sulfonylamino)-benzamide. 4,5-Dichloro-2-(quinoxaline-5-sulfonylamino)benzoic acid (8 mg, 0.02 mmol) was coupled with (R)-1-(2,4-difluorophenyl)ethylamine hydrochloride (EXAMPLE 2, Method 1, Step C; 8 mg, 0.04 mmol) according to the procedure described in EXAMPLE 1, Step K to provide the desired benzamide as a colorless solid (9 mg, 82%). MS (ESI): mass calculated for $C_{23}H_{16}Cl_2F_2N_4O_3S$, 536.0; m/z found, 535/537 [M−H]⁻. HPLC (reverse phase): $R_T$=10.45 min. ¹H NMR (500 MHz, CDCl₃): 11.15 (s, 1H), 8.85 (d, J=1.8 Hz, 1H), 8.79 (d, J=1.8 Hz, 1H), 8.54 (dd, J=7.4, 1.4 Hz, 1H), 8.32 (dd, J=7.4, 1.4 Hz, 1H), 7.89 (s, 1H), 7.87 (dd, J=8.2, 7.4 Hz, 1H), 7.35 (s, 1H), 7.30 (ddd, J=8.5, 8.5, 6.3 Hz, 1H), 6.93-6.88 (m, 1H), 6.88-6.83 (m, 1H), 6.30 (br d, J=6.5 Hz, 1H), 5.35-5.25 (m, 1H), 1.54 (d, J=7.0 Hz, 3H).

Example 6

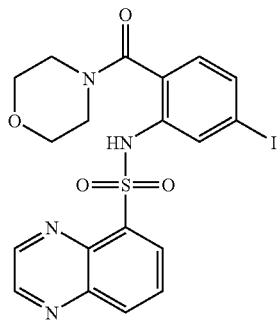

Quinoxaline-5-sulfonic acid [5-iodo-2-(morpholine-4-carbonyl)-phenyl]-amide.

Method 1.

The title compound was prepared from the HATU-mediated coupling of 4-iodo-2-(quinoxaline-5-sulfonylamino) benzoic acid (EXAMPLE 4, Step D) and morpholine and purified as described in EXAMPLE 1, Step K. MS (ESI): mass calculated for $C_{19}H_{17}IN_4O_4S$, 524.0; m/z found, 523 [M−H]⁻. HPLC (reverse phase): $R_T$=8.32 min. ¹H NMR (500 MHz, CDCl₃, rotameric broadening): 9.06 (d, J=1.8 Hz, 1H), 9.02 (d, J=1.8 Hz, 1H), 9.01 (br s, 1H), 8.51 (dd, J=7.0, 1.5 Hz, 1H), 8.37 (dd, J=8.4, 1.4 Hz, 1H), 7.96 (d, J=1.5 Hz, 1H), 7.90 (dd, J=8.4, 7.4 Hz, 1H), 7.38 (dd, J=8.0, 1.6 Hz, 1H), 6.76 (d, J=8.0 Hz, 1H), 3.70-3.40 (br m, 6H), 3.30-3.05 (br m, 2H).

Alternatively, quinoxaline-5-sulfonic acid [5-iodo-2-(morpholine-4-carbonyl)-phenyl]amide could be prepared by the following procedure:

Method 2.

A. 2-(Benzo[1,2,5]thiadiazole-4-sulfonylamino)-4-iodobenzoic acid methyl ester. To a solution of methyl 2-amino-4-iodobenzoate (EXAMPLE 4, Step B, 1.6 g, 5.8 mmol) in DCM (45 mL) at room temperature was added 4-chlorosulfonyl-2,1,3-benzothiadiazole (1.76 g, 7.51 mmol), and pyridine (0.93 mL, 11 mmol). The mixture was stirred at room temperature overnight, poured into 1 N HCl (200 mL), and extracted with DCM (2×100 mL). The combined organic layers were dried (Na₂SO₄) and concentrated in vacuo. The crude residue was purified by flash chromatography (hexanes/EtOAc) to afford the title sulfonamide as a tan solid (1.87 g, 68%). MS (ESI): calculated for $C_{14}H_{10}IN_3O_4S_2$, 474.9; m/z found, 474 [M−H]⁻. ¹H NMR (400 MHz, CDCl₃): 11.26 (br s, 1H), 8.40 (dd, J=7.0, 1.0 Hz, 1H), 8.24 (dd, J=8.8, 1.0 Hz, 1H), 8.12 (d, J=1.5 Hz, 1H), 7.74 (dd, J=8.8, 7.0 Hz, 1H), 7.53 (d, J=8.5 Hz, 1H), 7.32 (dd, J=8.5, 1.5 Hz, 1H), 3.91 (s, 3H).

B. 2-(Benzo[1,2,5]thiadiazole-4-sulfonylamino)-4-iodobenzoic acid. To a stirred suspension of 2-(benzo[1,2,5]thiadiazole-4-sulfonylamino)-4-iodobenzoic acid methyl ester (1.87 g, 3.93 mmol) in THF (20 mL) at room temperature was added LiOH (2 M in H₂O, 18 mL). The resulting orange mixture was stirred overnight at room temperature then poured into 0.5 M HCl (150 mL) causing precipitation of the desired benzoic acid. After stirring the mixture for several minutes to complete precipitation, the product was collected by suction filtration and air-dried to afford the acid as a tan solid (1.24 g, 69%). ¹H NMR (500 MHz, CDCl₃): 11.03 (br s, 1H), 8.34 (dd, J=7.2, 1.1 Hz, 1H), 8.19 (dd, J=8.8, 1.1 Hz, 1H), 8.09 (d, J=1.6 Hz, 1H), 7.69 (dd, J=8.8, 7.2 Hz, 1H), 7.56 (d, J=8.5 Hz, 1H), 7.30 (dd, J=8.5, 1.6 Hz, 1H), (COOH not observed).

C. Benzo[1,2,5]thiadiazole-4-sulfonic acid [5-iodo-2-(morpholine-4-carbonyl)-phenyl]-amide. The title compound was prepared from the HATU-mediated coupling of 2-(benzo[1,2,5]thiadiazole-4-sulfonylamino)-4-iodobenzoic acid and morpholine and purified as described in EXAMPLE 1, Step K. MS (ESI): mass calculated for $C_{17}H_{15}IN_4O_4S_2$, 530.0; m/z found, 531 [M+H]⁺, 553 [M+Na]⁺. HPLC (reverse phase): $R_T$=8.50 min. ¹H NMR (400 MHz, CDCl₃): (rotameric broadening) 8.91 (s, 1H), 8.31 (dd, J=7.0, 0.9 Hz, 1H), 8.27 (dd, J=8.8, 0.9 Hz, 1H), 7.97 (d, J=1.5 Hz, 1H), 7.74 (dd, J=8.8, 7.0 Hz, 1H), 7.41 (dd, J=8.1, 1.6 Hz, 1H), 6.78 (d, J=8.1 Hz, 1H), 3.75-3.05 (br m, 8H).

D. Quinoxaline-5-sulfonic acid [5-iodo-2-(morpholine-4-carbonyl)-phenyl]-amide. Zinc powder (1.1 g, 19 mmol) was added to a mixture of benzo[1,2,5]thiadiazole-4-sulfonic acid [5-iodo-2-(morpholine-4-carbonyl)-phenyl]amide (1.0 g, 1.9 mmol) and AcOH (20 mL), and the resulting mixture was heated at 50° C. for 1 h with vigorous stirring. The mixture was filtered through a pad of diatomaceous earth, rinsing well with methanol, and the clear solution was concentrated to a yellow solid. This material was dissolved in methanol (20 mL) and added to a mixture of glyoxal sodium bisulfite adduct (1.5 g, 5.7 mmol), AcOH (0.85 mL), NaOAc (0.16 g, 2.0 mmol), and H₂O (6 mL). The reaction was allowed to proceed under reflux for 3 h, then was diluted with EtOAc (200 mL) and filtered through a pad of diatomaceous earth, rinsing well with EtOAc. The filtrate was washed with H₂O (100 mL) and brine (100 mL), then was dried and concentrated to a yellow solid. Purification by flash chromatography gave the titled compound as a light yellow solid (0.69 g, 70%).

Example 7

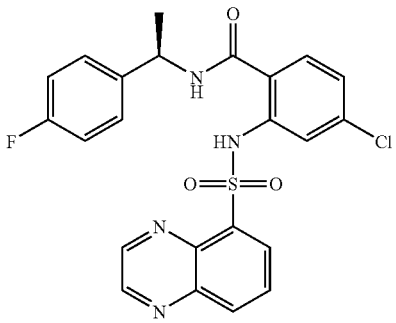

(R)-4-Chloro-N-[1-(4-fluorophenyl)-ethyl]-2-(quinoxaline-5-sulfonylamino)-benzamide.

A. S—(S)-2-Methyl-propane-2-sulfinic acid 4-fluorobenzylideneamide. A suspension of 4-fluorobenzaldehyde (0.53 g, 4.3 mmol), (S)-tert-butanesulfinamide (0.47 g, 3.9 mmol), and powdered anhydrous $CuSO_4$ (1.2 g, 7.8 mmol) was stirred in DCM (8 mL) overnight. The reaction mixture was filtered, and the filter cake was washed with DCM. The filtrate was concentrated in vacuo to give the N-sulfinyl imine as a viscous, colorless oil (0.81 g, 84%). $^1$H NMR (500 MHz, $CDCl_3$): 8.55 (s, 1H), 7.88-7.85 (m, 2H), 7.18-7.15 (m, 2H), 1.26 (s, 9H).

B. S—(S)-2-Methylpropane-2-sulfinic acid 1-(R)-[1-(4-fluorophenyl)ethyl]amide.

To a stirred solution of S—(S)-2-methyl-propane-2-sulfinic acid 4-fluoro-benzylideneamide (0.81 g, 3.1 mmol) in DCM (20 mL) at −50° C. was added a solution of methyl magnesium bromide (3.0 M in diethyl ether, 2.4 mL, 7.2 mmol). The reaction mixture was stirred at −50° C. for 1 h then allowed to warm slowly to room temperature overnight. The reaction was quenched by the addition of a satd. aq. $NH_4Cl$ solution, and the mixture was poured into $H_2O$ and extracted with DCM (3×). The combined organic layers were dried ($Na_2SO_4$) and concentrated in vacuo. Purification by flash chromatography (EtOAc/hexanes) provided the title compound as a colorless viscous oil (0.86 g, 98%, 94% de). Major diastereomer: $^1$H NMR (400 MHz, $CDCl_3$): 7.33-7.27 (m, 2H), 7.06-6.98 (m, 2H), 4.56 (dq, J=6.6, 3.2 Hz, 1H), 3.30 (br d, J=2.3 Hz, 1H), 1.52 (d, J=6.7 Hz, 3H), 1.20 (s, 9H).

C. (R)-1-(4-Fluorophenyl)ethylamine hydrochloride. To a stirred solution of S—(S)-2-methylpropane-2-sulfinic acid 1-(R)-[1-(4-fluorophenyl)ethyl]amide (94% de, 0.86 g, 3.5 mmol) in methanol (7 mL) at room temperature was added 2 mL of a satd. solution of HCl (g) in methanol. After several minutes, precipitated amine hydrochloride was visible. The reaction mixture was allowed to stir for 2 h at room temperature. The heterogeneous mixture was concentrated in vacuo until approximately 2 mL remained, and then the amine hydrochloride was fully precipitated by the addition of diethyl ether (10 mL). The HCl salt was collected by suction filtration, washed with diethyl ether, and dried in vacuo to give fine white crystals (484 mg, 78%, ~94% ee based on de of starting material). $^1$H NMR (400 MHz, $CDCl_3$): 8.67 (br s, 3H), 7.50-7.42 (m, 2H), 7.09-7.00 (m, 2H), 4.36 (br s, 1H), 1.64 (d, J=6.8 Hz, 3H).

D. (R)-4-Chloro-N-[1-(4-fluorophenyl)ethyl]-2-(quinoxaline-5-sulfonylamino)-benzamide. The title compound was prepared from the HATU-mediated coupling of 4-chloro-2-(quinoxaline-5-sulfonylamino)benzoic acid (EXAMPLE 3, Step B) and (R)-1-(4-fluorophenyl)ethylamine hydrochloride and purified as described in EXAMPLE 1, Step K. MS (ESI): mass calculated for $C_{23}H_{18}ClFN_4O_3S$, 484.1; m/z found, 483 [M−H]$^-$. HPLC (reverse phase): $R_T$=9.95 min. $^1$H NMR (500 MHz, $CDCl_3$): 11.40 (s, 1H), 8.84 (d, J=1.8 Hz, 1H), 8.77 (d, J=1.8 Hz, 1H), 8.57 (dd, J=7.4, 1.4 Hz, 1H), 8.31 (dd, J=7.4, 1.4 Hz, 1H), 7.87 (dd, J=8.4, 7.4 Hz, 1H), 7.77 (d, J=2.0 Hz, 1H), 7.30-7.27 (m, 2H), 7.22 (d, J=8.4 Hz, 1H), 7.08-7.04 (m, 2H), 6.91 (dd, J=8.4, 2.0 Hz, 1H), 6.11 (br d, J=6.5 Hz, 1H), 5.24-5.20 (m, 1H), 1.53 (d, J=7.0 Hz, 3H).

Example 8

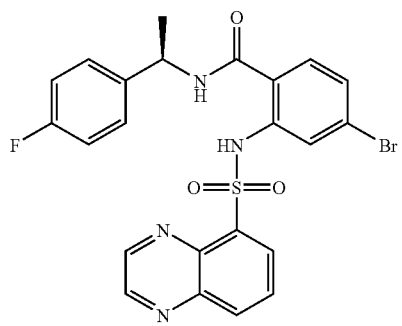

(R)-4-Bromo-N-[1-(4-fluorophenyl)-ethyl]-2-(quinoxaline-5-sulfonylamino)-benzamide.

The title compound was prepared from the HATU-mediated coupling of 4-bromo-2-(quinoxaline-5-sulfonylamino)benzoic acid (EXAMPLE 1, Step G) and (R)-1-(4-fluorophenyl)ethylamine hydrochloride (EXAMPLE 7, Step C) and purified as described in EXAMPLE 1, Step K. MS (ESI): mass calculated for $C_{23}H_{18}BrFN_4O_3S$, 528.0; m/z found, 527/529 [M−H]$^-$. HPLC (reverse phase): $R_T$=10.03 min. $^1$H NMR (500 MHz, $CDCl_3$): 11.34 (s, 1H), 8.85 (d, J=1.8 Hz, 1H), 8.78 (d, J=1.8 Hz, 1H), 8.57 (dd, J=7.4, 1.4 Hz, 1H), 8.32 (dd, J=7.4, 1.4 Hz, 1H), 7.92 (d, J=1.8 Hz, 1H), 7.87 (dd, J=8.4, 7.4 Hz, 1H), 7.30-7.25 (m, 2H), 7.15 (d, J=8.4 Hz, 1H), 7.10-7.00 (m, 2H), 6.91 (dd, J=8.4, 2.0 Hz, 1H), 6.13 (br d, J=6.5 Hz, 1H), 5.25-5.15 (m, 1H), 1.53 (d, J=7.0 Hz, 3H).

Example 9

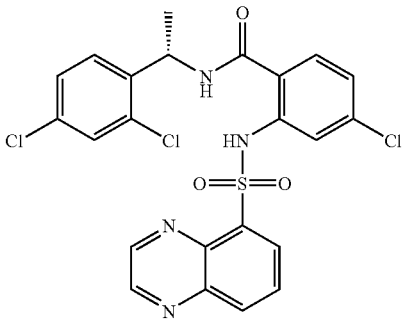

(S)-4-Chloro-N-[1-(2,4-dichlorophenyl)ethyl]-2-(quinoxaline-5-sulfonylamino)-benzamide.

A. (S)-1-(2,4-Dichloroorophenyl)ethylamine hydrochloride. The amine was prepared according to the procedures described in EXAMPLE 1, Steps H through J, starting with (R)-tert-butanesulfinamide.

B. (S)-4-Chloro-N-[1-(2,4-dichlorophenyl)ethyl]-2-(quinoxaline-5-sulfonylamino)-benzamide. The title compound was prepared from the HATU mediated coupling of 4-chloro-2-(quinoxaline-5-sulfonylamino)benzoic acid (EXAMPLE 3, Step B) and (S)-1-(2,4-difluorophenyl)ethylamine hydrochloride and purified as described in EXAMPLE 1, Step K. MS (ESI): mass calculated for $C_{23}H_{17}Cl_3N_4O_3S$, 534.0; m/z found, 533/535 [M−H]$^-$. HPLC (reverse phase): $R_T$=10.60 min. $^1$H NMR (500 MHz, CDCl$_3$): 11.36 (s, 1H), 8.85 (d, J=1.8 Hz, 1H), 8.75 (d, J=1.8 Hz, 1H), 8.55 (dd, J=7.4, 1.4 Hz, 1H), 8.31 (dd, J=7.4, 1.4 Hz, 1H), 7.86 (dd, J=8.4, 7.4 Hz, 1H), 7.79 (d, J=2.0 Hz, 1H), 7.47-7.42 (m, 1H), 7.28-7.26 (m, 1H), 7.22-7.20 (m, 2H), 6.92 (dd, J=8.4, 2.0 Hz, 1H), 6.34 (br d, J=6.5 Hz, 1H), 5.45-5.35 (m, 1H), 1.52 (d, J=7.0 Hz, 3H).

Example 10

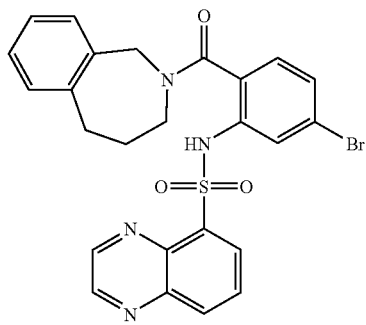

Quinoxaline-5-sulfonic acid [5-bromo-2-(1,3,4,5-tetrahydrobenzo[c]azepine-2-carbonyl)phenyl]-amide.

A. 2,3,4,5-Tetrahydrobenzo[c]azepin-1-one. To an ice-cold solution of 3,4-dihydro-2H-naphthalen-1-one (4.44 g, 30.4 mol) in concentrated HCl (60 mL) was added NaN$_3$ (2.02 g, 30.4 mol) in portions. The resulting mixture was allowed to stir at 0° C. for 30 min, then was warmed to room temperature and stirred overnight. The reaction mixture was poured onto ice, brought to pH ~10 with 1 M NaOH, and extracted with DCM (3×). The combined organic layers were dried over MgSO$_4$, filtered, concentrated, and purified by flash chromatography (hexanes/EtOAc) to provide the title compound (1.23 g, 25%). HPLC (reverse phase): $R_T$=6.92 min. $^1$H NMR (500 MHz, CDCl$_3$): 7.71 (dd, J=7.6 Hz, 1.3 Hz, 1H), 7.42-7.39 (m, 1H), 7.36-7.32 (m, 1H), 7.20-7.19 (m, 1H), 3.15-3.11 (m, 2H), 2.87 (t, J=7.1 Hz, 2H), 2.05-2.00 (m, 2H), (NH not observed).

B. 2,3,4,5-Tetrahydro-1H-benzo[c]azepine. 2,3,4,5-Tetrahydro-benzo[c]azepin-1-one (1.23 g, 7.63 mmol) was dissolved in THF (10 mL) and cooled to 0° C. Lithium aluminum hydride (0.89 g, 23 mmol) was added slowly in small portions. The resulting mixture was heated at reflux for 24 h, cooled to room temperature and quenched with successive dropwise addition of H$_2$O (0.89 mL), 15% aq. NaOH solution (0.89 mL), and H$_2$O (2.67 mL). The salts were removed by filtration and the filtrate was concentrated to provide the title compound (0.68 g, 61%). $^1$H NMR (400 MHz, CDCl$_3$): 7.16-7.10 (m, 4H), 3.94 (s, 2H), 3.21 (t, J=5.3 Hz, 2H), 2.96-2.94 (m, 2H), 1.73-1.71 (m, 2H).

C. Quinoxaline-5-sulfonic acid [5-bromo-2-(1,3,4,5-tetrahydrobenzo[c]azepine-2-carbonyl)phenyl]-amide. The title compound was prepared from the HATU-mediated coupling of 4-bromo-2-(quinoxaline-5-sulfonylamino)benzoic acid (EXAMPLE 1, Step G) and 2,3,4,5-tetrahydro-1H-benzo[c]azepine and purified as described in EXAMPLE 1, Step K. MS (ESI): mass calculated for $C_{25}H_{21}BrN_4O_3S$, 536.0; m/z found, 537/539 [M+H]$^+$. HPLC (reverse phase): $R_T$=9.80 min. $^1$H NMR (500 MHz, CDCl$_3$, mixture of rotamers): 9.07 (br s, 0.5H), 9.00 (br s, 0.5H), 8.93 (br s, 1H), 8.84-8.76 (m, 1H), 8.52-8.46 (m, 1H), 8.36-8.32 (m, 1H), 7.90-7.84 (m, 2H), 7.48-7.36 (m, 0.5H), 7.25-7.20 (m, 1H), 7.14-7.08 (m, 1.5H), 7.06-7.00 (m, 0.5H), 6.78-6.76 (m, 0.5H), 6.62-6.58 (m, 0.5H), 6.44-6.42 (m, 0.5H), 4.44-4.28 (m, 1H), 3.90-3.88 (m, 1H), 3.7-3.5 (br m, 1H), 3.08-3.01 (m, 1H), 2.90-2.80 (m, 2H), 1.90-1.80 (m, 1H), 1.50-1.40 (m, 2H).

Example 11

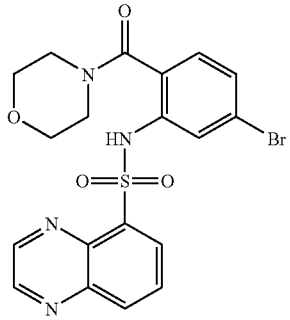

(R)-Quinoxaline-5-sulfonic acid [5-bromo-2-(morpholine-4-carbonyl)-phenyl]-amide.

The title compound was prepared from the HATU-mediated coupling of 4-bromo-2-(quinoxaline-5-sulfonylamino) benzoic acid (EXAMPLE 1, Step G) and morpholine and purified as described in EXAMPLE 1, Step K. MS (ESI): mass calculated for $C_{19}H_{17}BrN_4O_4S$, 476.0; m/z found, 475/477 [M−H]$^-$. HPLC (reverse phase): $R_T$=8.23 min. $^1$H NMR (500 MHz, CDCl$_3$, rotameric broadening): 9.08 (br s, 1H), 9.06 (d, J=1.8 Hz, 1H), 9.01 (d, J=1.8 Hz, 1H), 8.52 (dd, J=7.0, 1.5 Hz, 1H), 8.37 (dd, J=8.4, 1.4 Hz, 1H), 7.90 (dd, J=8.4, 7.4 Hz, 1H), 7.79 (d, J=1.5 Hz, 1H), 7.17 (dd, J=8.0, 1.6 Hz, 1H), 6.92 (d, J=8.0 Hz, 1H), 3.68-3.40 (br m, 6H), 3.35-3.05 (br m, 2H).

Example 12

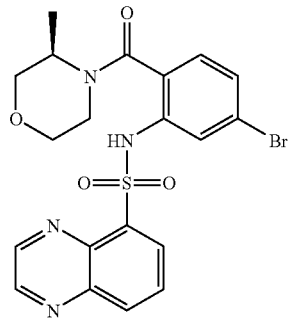

(R)-Quinoxaline-5-sulfonic acid [5-bromo-2-(3-methylmorpholine-4-carbonyl)-phenyl]-amide.

A. (R)-2-(2-Hydroxyethylamino)propan-1-ol. Condensed ethylene oxide (0.8 g, 20 mmol) was added to a solution of (R)-2-aminopropan-1-ol (5 g, 70 mmol) in $H_2O$ at 0° C. The mixture was stirred overnight with slow warming to room temperature and then was concentrated in vacuo to give a viscous, colorless oil. The crude product was purified by bulb-to-bulb distillation under high vacuum to provide the desired diol as a viscous liquid. $^1$H NMR (400 MHz, $CDCl_3$): 3.74-3.64 (m, 2H), 3.61 (dd, J=10.8, 3.9 Hz, 1H), 3.33 (dd, J=10.8, 7.3 Hz, 1H), 2.88 (ddd, J=12.3, 6.1, 4.1 Hz, 1H), 2.80 (ddq, J=7.2, 6.5, 3.9 Hz, 1H), 2.70 (ddd, J=12.3, 6.0, 4.1 Hz, 1H), 1.06 (d, J=6.5 Hz, 3H).

B. (R)-3-Methylmorpholine. The crude (R)-2-(2-hydroxyethylamino)propan-1-ol from step A was transferred to a sealed tube, and 10 mL concentrated $H_2SO_4$ was carefully added. The tube was sealed and heated at 140° C. for 14 h. The dark brown mixture was poured over crushed ice and made basic by slow addition of 5 N NaOH. The mixture was extracted with diethyl ether (5×). The combined organic layers were dried ($MgSO_4$) and concentrated to provide the morpholine as a yellow liquid (1.19 g, 65%). $^1$H NMR (500 MHz, $CDCl_3$): 3.82-3.72 (m, 2H), 3.52-3.44 (m, 1H), 3.10 (t, J=10.0 Hz, 1H), 3.03-2.95 (m, 1H), 2.95-2.83 (m, 2H), 0.96 (d, J=6.4 Hz, 3H).

C. (R)-Quinoxaline-5-sulfonic acid [5-bromo-2-(3-methylmorpholine-4-carbonyl)-phenyl]-amide. (R)-Quinoxaline-5-sulfonic acid [5-bromo-2-(3-methylmorpholine-4-carbonyl)-phenyl]-amide was prepared from the HATU-mediated coupling of 4-bromo-2-(quinoxaline-5-sulfonylamino)benzoic acid (EXAMPLE 1, Step G) and (R)-3-methylmorpholine and purified as described in EXAMPLE 1, Step K. MS (ESI): mass calculated for $C_{20}H_{19}BrN_4O_4S$, 490.0; m/z found, 489/491 [M−H]$^-$. HPLC (reverse phase): $R_T$=8.63 min. $^1$H NMR (500 MHz, $CDCl_3$, rotameric broadening): 9.05 (d, J=1.8 Hz, 1H), 9.01 (br s, 1H), 9.00 (d, J=1.8 Hz, 1H), 8.56 (dd, J=7.0, 1.5 Hz, 1H), 8.37 (dd, J=8.4, 1.4 Hz, 1H), 7.91 (dd, J=8.4, 7.4 Hz, 1H), 7.72 (d, J=1.5 Hz, 1H), 7.16 (dd, J=8.0, 1.6 Hz, 1H), 6.93 (d, J=8.1 Hz, 1H), 4.50-4.00 (br m, 1H), 3.91-3.78 (m, 1H), 3.73-3.58 (m, 1H), 3.50 (dd, J=11.5, 2.7 Hz, 1H), 3.40-3.17 (m, 3H), 1.25 (br m, 3H).

Example 13

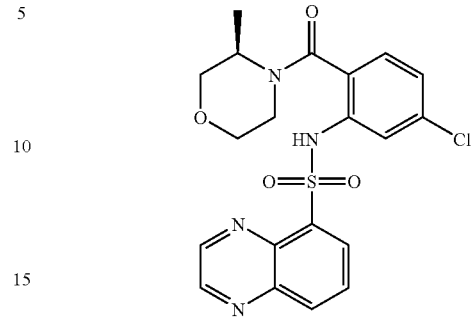

(R)-Quinoxaline-5-sulfonic acid [5-chloro-2-(3-methylmorpholine-4-carbonyl)-phenyl]-amide.

The title compound was prepared from the HATU-mediated coupling of 4-chloro-2-(quinoxaline-5-sulfonylamino)benzoic acid (EXAMPLE 3, Step B) and (R)-3-methylmorpholine (EXAMPLE 12, Step B) and purified as described in EXAMPLE 1, Step K. MS (ESI): mass calculated for $C_{20}H_{19}ClN_4O_4S$, 446.1; m/z found, 445 [M−H]$^-$. HPLC (reverse phase): $R_T$=8.54 min. $^1$H NMR (500 MHz, $CDCl_3$, rotameric broadening): 9.05 (d, J=1.8 Hz, 1H), 9.04 (br s, 1H), 9.00 (d, J=1.8 Hz, 1H), 8.56 (dd, J=7.0, 1.5 Hz, 1H), 8.37 (dd, J=8.4, 1.4 Hz, 1H), 7.91 (dd, J=8.4, 7.4 Hz, 1H), 7.56 (br s, 1H), 7.01-6.98 (m, 2H), 4.4-4.2 (br m, 1H), 3.90-3.82 (m, 1H), 3.68-3.62 (m, 1H), 3.51 (dd, J=11.5, 2.7 Hz, 1H), 3.40-3.20 (m, 3H), 1.31-1.23 (br m, 3H).

Example 14

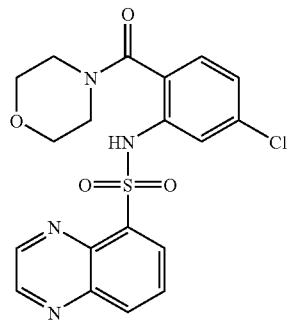

(R)-Quinoxaline-5-sulfonic acid [5-chloro-2-(morpholine-4-carbonyl)phenyl]-amide.

The title compound was prepared from the HATU-mediated coupling of 4-chloro-2-(quinoxaline-5-sulfonylamino)benzoic acid (EXAMPLE 3, Step B) and morpholine and purified as described in EXAMPLE 1, Step K. MS (ESI): mass calculated for $C_{19}H_{17}ClN_4O_4S$, 432.1; m/z found, 431 [M−H]$^-$. HPLC (reverse phase): $R_T$=8.14 min. $^1$H NMR (500 MHz, $CDCl_3$, rotameric broadening): 9.11 (br s, 1H), 9.06 (d, J=1.8 Hz, 1H), 9.01 (d, J=1.8 Hz, 1H), 8.52 (dd, J=7.0, 1.5 Hz, 1H), 8.37 (dd, J=8.4, 1.4 Hz, 1H), 7.90 (dd, J=8.4, 7.4 Hz, 1H), 7.63 (d, J=1.5 Hz, 1H), 7.05-6.98 (m, 2H), 3.65-3.40 (br m, 6H), 3.50-3.00 (br m, 2H).

Example 15

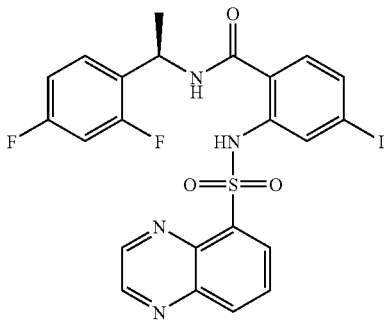

(R)-N-[1-(2,4-Difluorophenyl)-ethyl]-4-iodo-2-(quinoxaline-5-sulfonylamino)-benzamide.

The title compound was prepared from the HATU-mediated coupling of 4-iodo-2-(quinoxaline-5-sulfonylamino) benzoic acid (EXAMPLE 4, Step D) and (R)-1-(2,4-difluorophenyl)ethylamine hydrochloride (EXAMPLE 2, Method 1, Step C) and purified as described in EXAMPLE 1, Step K. MS (ESI): mass calculated for $C_{23}H_{17}F_2IN_4O_3S$, 594.0; m/z found, 593 [M−H]⁻. HPLC (reverse phase): $R_T$=10.16 min. ¹H NMR (500 MHz, CDCl₃): 11.22 (s, 1H), 8.84 (d, J=1.8 Hz, 1H), 8.79 (d, J=1.8 Hz 1H), 8.55 (dd, J=7.4, 1.4 Hz, 1H), 8.30 (dd, J=7.4, 1.4 Hz, 1H), 8.11 (d, J=1.8 Hz, 1H), 7.87 (dd, J=8.4, 7.4 Hz, 1H), 7.32-7.27 (m, 2H), 6.99 (d, J=8.2, 1H), 6.89-6.85 (m, 1H), 6.85-6.80 (m, 1H), 6.33 (br d, J=7.7 Hz, 1H), 5.35-5.27 (m, 1H), 1.53 (d, J=7.0 Hz, 3H).

Example 16

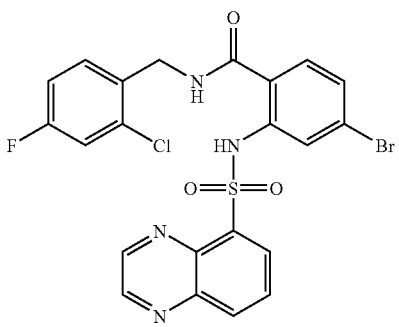

4-Bromo-N-(2-chloro-4-fluoro-benzyl)-2-(quinoxaline-5-sulfonylamino)-benzamide.

The title compound was prepared from the HATU-mediated coupling of 4-bromo-2-(quinoxaline-5-sulfonylamino)benzoic acid (EXAMPLE 1, Step G) and 2-chloro-4-fluorobenzylamine and purified as described in EXAMPLE 1, Step K. MS (ESI): mass calculated for $C_{22}H_{15}BrClFN_4O_3S$, 548.0; m/z found, 549/550 [M+H]⁺, 571/573 [M+Na]⁺. HPLC (reverse phase): $R_T$=9.86 min. ¹H NMR (500 MHz, CDCl₃): 11.29 (s, 1H), 8.88 (dd, J=15.3, 6.0 Hz, 2H), 8.57 (dd, J=7.4, 1.4 Hz, 1H), 8.32 (dd, J=8.4, 1.8 Hz, 1H), 8.31 (d, J=1.8 Hz, 1H), 7.93 (d, J=1.8 Hz, 1H), 7.88 (dd, J=8.4, 7.4 Hz, 1H), 7.43 (dd, J=8.5, 6.0 Hz, 1H), 7.16 (dd, J=8.3, 2.6 Hz, 1H), 7.14 (d, J=8.4 Hz, 1H), 7.07 (dd, J=8.5, 2.1 Hz, 1H), 7.01 (ddd, J=8.2, 8.2, 2.5 Hz, 1H), 6.38-6.33 (m, 1H), 4.57 (d, J=6.0 Hz, 1H).

Example 17

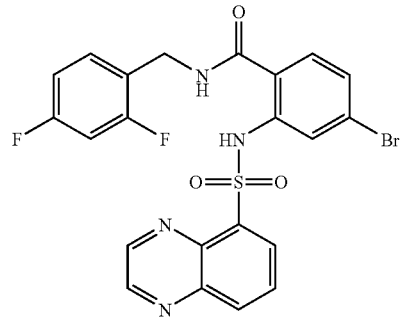

4-Bromo-N-(2,4-difluoro-benzyl)-2-(quinoxaline-5-sulfonylamino)-benzamide.

The title compound was prepared from the HATU-mediated coupling of 4-bromo-2-(quinoxaline-5-sulfonylamino)benzoic acid (EXAMPLE 1, Step G) and 2,4-difluorobenzylamine and purified as described in EXAMPLE 1, Step K. MS (ESI): mass calculated for $C_{22}H_{15}BrF_2N_4O_3S$, 532.0; m/z found, 533/535 [M+H]⁺, 555/557 [M+Na]⁺. HPLC (reverse phase): $R_T$=9.64 min. ¹H NMR (500 MHz, CDCl₃, rotameric broadening): 11.31 (s, 1H), 8.92-8.86 (m, 2H), 8.62-8.53 (m, 1H), 8.35-8.29 (m, 1H), 7.96-7.90 (m, 1H), 7.90-7.83 (m, 1H), 7.41-7.32 (m, 1H), 7.15-7.10 (m, 1H), 7.09-7.03 (m, 1H), 6.94-6.82 (m, 2H), 6.31-6.24 (m, 1H), 4.53 (br s, 2H).

Example 18

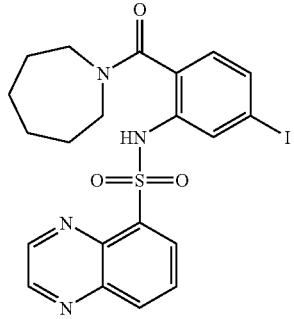

Quinoxaline-5-sulfonic acid [2-(azepane-1-carbonyl)-5-iodophenyl]-amide.

The title compound was prepared from the HATU-mediated coupling of 4-iodo-2-(quinoxaline-5-sulfonylamino)benzoic acid (EXAMPLE 4, Step D) and azepane and purified as described in EXAMPLE 1, Step K. MS (ESI): mass calculated for $C_{21}H_{21}IN_4O_3S$, 536.0; m/z found, 535 [M−H]⁻. HPLC (reverse phase): $R_T$=9.42 min. ¹H NMR (500 MHz, CDCl₃, rotameric broadening): 9.08 (d, J=1.8 Hz, 1H), 9.00

(d, J=1.8 Hz, 1H), 8.81 (br s, 1H), 8.49 (d, J=7.3, 1H), 8.35 (d, J=8.4, Hz, 1H), 7.98 (s, 1H), 7.88 (t, J=8.1 Hz, 1H), 7.37 (d, J=8.1 Hz, 1H), 6.75 (d, J=8.0 Hz, 1H), 3.30-3.27 (br m, 2H), 2.91-2.89 (m, 2H), 1.66-1.63 (m, 2H), 1.63-1.54 (m, 2H), 1.50-1.43 (br m, 4H).

Example 19

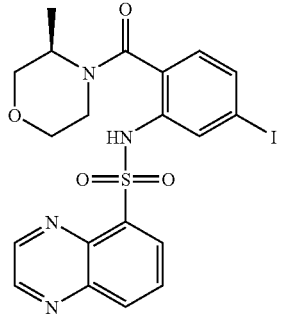

(R)-Quinoxaline-5-sulfonic acid [5-iodo-2-(3-methylmorpholine-4-carbonyl)-phenyl]-amide.

The title compound was prepared from the HATU-mediated coupling of 4-iodo-2-(quinoxaline-5-sulfonylamino)benzoic acid (EXAMPLE 4, Step D) and (R)-3-methylmorpholine and purified as described in EXAMPLE 1, Step K. MS (ESI): mass calculated for $C_{20}H_{19}IN_4O_4S$, 538.0; m/z found, 537 [M−H]−. HPLC (reverse phase): $R_T$=8.71 min. $^1$H NMR (400 MHz, CDCl$_3$, rotameric broadening): 9.05 (d, J=1.8 Hz, 1H), 9.00 (d, J=1.8 Hz, 1H), 8.94 (br s, 1H), 8.54 (dd, J=7.0, 1.5 Hz, 1H), 8.37 (dd, J=8.4, 1.4 Hz, 1H), 7.92 (dd, J=8.4, 7.4 Hz, 1H), 7.90-7.89 (m, 1H), 7.37 (dd, J=8.0, 1.6 Hz, 1H), 6.78 (d, J=8.0 Hz, 1H), 4.5-4.0 (br m, 1H), 3.90-3.82 (m, 1H), 3.66-3.64 (m, 1H), 3.47 (dd, J=11.5, 2.7 Hz, 1H), 3.35-3.25 (m, 3H), 1.31-1.21 (br m, 3H).

Example 20

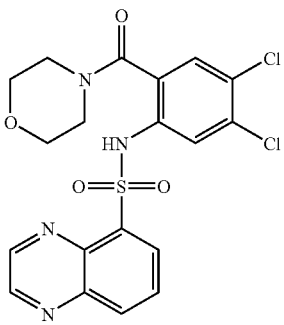

Quinoxaline-5-sulfonic acid [4,5-dichloro-2-(morpholine-4-carbonyl)-phenyl]-amide.

The title compound was prepared from the HATU-mediated coupling of 4,5-dichloro-2-(quinoxaline-5-sulfonylamino)-benzoic acid (EXAMPLE 5, Step D) and morpholine and purified as described in EXAMPLE 1, Step K. MS (ESI): mass calculated for $C_{19}H_{16}Cl_2N_4O_4S$, 466.0; m/z found, 465/467 [M−H]−. HPLC (reverse phase): $R_T$=8.84 min. $^1$H NMR (500 MHz, CDCl$_3$, rotameric broadening): 9.06 (d, J=1.8 Hz, 1H), 9.03 (d, J=1.8 Hz, 1H), 8.51 (dd, J=7.0, 1.5 Hz, 1H), 8.38 (dd, J=8.4, 1.4 Hz, 1H), 8.08 (d, J=1.5 Hz, 1H), 7.91 (dd, J=8.4, 7.4 Hz, 1H), 7.70 (s, 1H), 7.14 (s, 1H), 4.35-4.10 (br m, 4H), 3.65-3.48 (br m, 4H).

Example 21

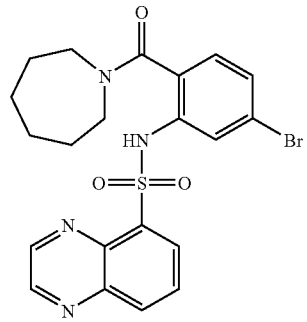

Quinoxaline-5-sulfonic acid [2-(azepane-1-carbonyl)-5-bromophenyl]-amide.

The title compound was prepared from the HATU-mediated coupling of 4-bromo-2-(quinoxaline-5-sulfonylamino)benzoic acid (EXAMPLE 1, Step G) and azepane and purified as described in EXAMPLE 1, Step K. MS (ESI): mass calculated for $C_{21}H_{21}BrN_4O_3S$, 488.0; m/z found, 487/489 [M−H]−. HPLC (reverse phase): $R_T$=9.34 min. $^1$H NMR (500 MHz, CDCl$_3$, rotameric broadening): 9.08 (d, J=1.8 Hz, 1H), 9.00 (d, J=1.8 Hz, 1H), 8.87 (br s, 1H), 8.50 (d, J=7.3 Hz, 1H), 8.34 (d, J=8.4 Hz, 1H), 7.87 (dd, J=8.4, 7.4 Hz, 1H), 7.80 (d, J=1.8 Hz, 1H), 7.16 (dd, J=8.1, 1.8 Hz, 1H), 6.91 (d, J=8.1 Hz, 1H), 3.33-3.28 (br m, 2H), 2.93-2.91 (m, 2H), 1.68-1.65 (m, 2H), 1.58-1.52 (m, 2H), 1.50-1.42 (br m, 4H).

Example 22

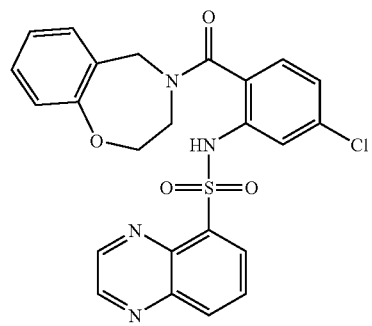

Quinoxaline-5-sulfonic acid [5-chloro-2-(2,3-dihydro-5H-benzo[f][1,4]oxazepine-4-carbonyl)-phenyl]-amide.

A. 3,4-Dihydro-2H-benzo[f][1,4]oxazepin-5-one. To a 0° C. solution of chroman-4-one (2.0 g, 0.014 mol) in concentrated $H_2SO_4$ (10 mL) was added NaN$_3$ (1.1 g, 0.018 mol) in portions. The resulting mixture was stirred at 0° C. for 30 min, then was warmed to room temperature and stirred overnight. The reaction mixture was poured onto ice, basified to pH ~10 with 1 M NaOH, and extracted with EtOAc (3×). The combined organic layers were dried over MgSO$_4$, filtered, and concentrated, to provide the title compound (1.40 g, 64%). HPLC (reverse phase): $R_T$=6.40 min. $^1$H NMR (500 MHz, CDCl$_3$): 7.98 (dd, J=8.0, 1.8 Hz, 1H), 7.45-7.42 (m, 1H), 7.16-7.12 (m, 1H), 7.02 (d, J=8.2 Hz, 1H), 6.68 (br s, 1H), 4.40 (t, J=4.7 Hz, 2H), 3.51 (q, J=5.3 Hz, 2H).

B. 2,3,4,5-Tetrahydro-benzo[f][1,4]oxazepine. To a 0° C. solution of 3,4-dihydro-2H-benzo[f][1,4]oxazepin-5-one (1.22 g, 7.48 mmol) in THF (20 mL) was added lithium aluminum hydride (0.85 g, 22 mmol) in small portions. The resulting mixture was heated at reflux for 24 h, cooled to room temperature, and quenched with successive dropwise addition of H$_2$O (0.85 mL), 15% aq. NaOH solution (0.85 mL), and H$_2$O (2.55 mL). The salts were removed by filtration, and the filtrate was concentrated to yield the title compound (0.80 g, 72%). TLC (silica, EtOAc): $R_f$=0.14. $^1$H NMR (500 MHz, CDCl$_3$): 7.19-7.12 (m, 2H), 7.03-6.97 (m, 2H), 4.04 (t, J=4.5 Hz, 2H), 3.96 (s, 2H), 3.23 (t, J=4.5 Hz, 2H), (one H not observed).

C. Quinoxaline-5-sulfonic acid [5-chloro-2-(2,3-dihydro-5H-benzo[f][1,4]oxazepine-4-carbonyl)-phenyl]-amide. The title compound was prepared from the HATU-mediated coupling of 4-chloro-2-(quinoxaline-5-sulfonylamino)benzoic acid (EXAMPLE 3, Step B) and 2,3,4,5-tetrahydro-benzo[f][1,4]oxazepine and purified as described in EXAMPLE 1, Step K. MS (ESI): mass calculated for $C_{24}H_{19}ClN_4O_4S$, 494.1; m/z found, 495/497 [M+H]$^+$. HPLC (reverse phase): $R_T$=9.36 min. $^1$H NMR (400 MHz, CDCl$_3$, rotameric broadening): 9.09-8.97 (m, 2H), 8.85 (br s, 0.5H), 8.68 (br s, 0.5H), 8.52-8.47 (m, 1H), 8.36-8.34 (m, 1H), 7.90-7.86 (m, 1H), 7.71 (br s, 1H), 7.4-7.2 (m, 2H), 7.04-7.00 (m, 1H), 6.98 (dd, J=8.2, 1.8 Hz, 1H), 6.98-6.91 (m, 1H), 6.82-6.78 (m, 0.5H), 6.65-6.60 (m, 0.5H), 4.55-4.47 (m, 1H), 4.09 (br s, 1H), 3.91 (br s, 1.5H), 3.71 (br s, 1.5H), 3.38 (br s, 1H).

Example 23

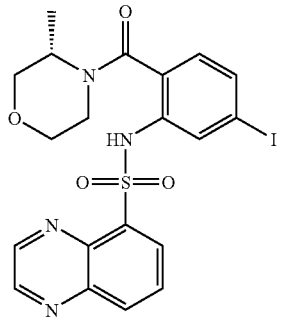

(S)-Quinoxaline-5-sulfonic acid [5-iodo-2-(3-methylmorpholine-4-carbonyl)-phenyl]-amide.

A. (S)-3-Methylmorpholine. (S)-3-Methylmorpholine was prepared as described for the (R) enantiomer (EXAMPLE 12, Steps A and B) but starting with (S)-2-aminopropan-1-ol.

B. (S)-Quinoxaline-5-sulfonic acid [5-iodo-2-(3-methylmorpholine-4-carbonyl)-phenyl]-amide. The title compound was prepared from the HATU-mediated coupling of 4-iodo-2-(quinoxaline-5-sulfonylamino)benzoic acid (EXAMPLE 4, Step D) and (S)-3-methylmorpholine and purified as described in EXAMPLE 1, Step K. MS (ESI): mass calculated for $C_{20}H_{19}IN_4O_4S$, 538.0; m/z found, 537 [M−H]$^-$. HPLC (reverse phase): $R_T$=8.52 min. $^1$H NMR (400 MHz, CDCl$_3$, rotameric broadening): 9.05 (d, J=1.8 Hz, 1H), 9.00 (d, J=1.8 Hz, 1H), 8.95 (br s, 1H), 8.55 (dd, J=7.0, 1.5 Hz, 1H), 8.37 (dd, J=8.4, 1.4 Hz, 1H), 7.92 (dd, J=8.4, 7.4 Hz, 1H), 7.90 (br s, 1H), 7.37 (dd, J=8.0, 1.6 Hz, 1H), 6.78 (d, J=8.0 Hz, 1H), 4.30 (br m, 1H), 3.90-3.82 (m, 1H), 3.67-3.61 (m, 1H), 3.48 (dd, J=11.5, 2.7 Hz, 1H), 3.35-3.20 (m, 2H), 1.30-1.20 (br m, 3H), 1.0-0.9 (m, 1H).

Example 24

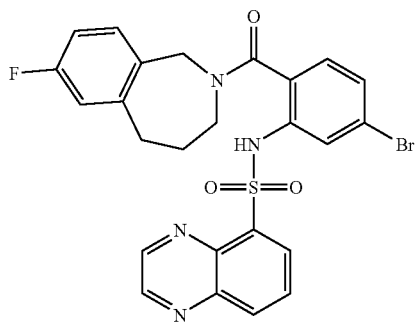

Quinoxaline-5-sulfonic acid [5-bromo-2-(7-fluoro-1,3,4,5-tetrahydro-benzo[c]azepine-2-carbonyl)-phenyl]-amide.

A. 7-Fluoro-2,3,4,5-tetrahydro-benzo[c]azepin-1-one. A suspension of 6-fluorotetralone (0.60 g, 3.6 mmol) in concentrated HCl at 0° C. was treated with NaN$_3$ (260 mg, 4.0 mmol). The reaction was stirred 30 min at 0° C. then was allowed to warm to room temperature and was stirred for 14 h. The reaction mixture was poured over crushed ice, and the resulting mixture was made basic by the addition of 5 M NaOH, and was extracted with DCM (3×). The combined organic extracts were dried (Na$_2$SO$_4$) and concentrated. The residue was purified by flash chromatography (EtOAc/hexanes) to provide 0.38 g (59%) of the title amide as a tan solid. $^1$H NMR (400 MHz, CDCl$_3$): 7.72 (dd, J=8.5, 5.9 Hz, 1H), 7.02 (ddd, J=8.4, 8.4, 2.6 Hz, 1H), 6.91 (dd, J=9.2, 2.6 Hz, 1H), 6.25 (br s, 1H), 3.14 (q, J=6.5 Hz, 2H), 2.86 (t, J=7.1 Hz, 2H), 2.09-1.98 (m, 2H).

B. 7-Fluoro-2,3,4,5-tetrahydro-1H-benzo[c]azepine. To a suspension of lithium aluminum hydride (280 mg, 7.4 mmol) in THF (10 mL) at room temperature was added a solution of 7-fluoro-2,3,4,5-tetrahydrobenzo[c]azepin-1-one (0.38 g, 2.1 mmol) in THF (10 mL) dropwise via syringe. The syringe was rinsed with an additional 5 mL of THF that was added to the reaction mixture. The reaction mixture was heated at reflux for 5 h, cooled to room temperature, and quenched by the addition of H$_2$O (0.3 mL) followed by 15% aq. NaOH (0.3 mL). After 5 min, H$_2$O (0.9 mL) was added, and the mixture was stirred rapidly for 30 min resulting in precipitation of aluminum salts. The mixture was filtered and washed with THF. Concentration in vacuo provided the desired azepine (340 mg, 98%) as a yellow oil. $^1$H NMR (400 MHz, CDCl$_3$): 7.06 (dd, J=8.2, 5.8 Hz, 1H), 6.86 (dd, J=9.5, 2.6 Hz, 1H), 6.77 (ddd, J=8.4, 8.4, 2.7 Hz, 1H), 3.9 (s, 2H), 3.20 (t, J=5.2 Hz, 2H), 2.95-2.88 (m, 2H), 1.78-1.66 (m, 2H), 1.33 (br s, 1H).

C. Quinoxaline-5-sulfonic acid [5-bromo-2-(7-fluoro-1,3,4,5-tetrahydro-benzo[c]azepine-2-carbonyl)-phenyl]-amide. The title compound was prepared from the HATU-mediated coupling of 4-bromo-2-(quinoxaline-5-sulfonylamino)benzoic acid (EXAMPLE 1, Step G) and 7-fluoro-2,3,4,5-tetrahydro-1H-benzo[c]azepine and purified as described in EXAMPLE 1, Step K. MS (ESI): mass calculated $C_{25}H_{20}BrFN_4O_3S$, 554.0; m/z found, 553/555 [M−H]⁻. HPLC (reverse phase): $R_T$=9.73 min. ¹H NMR (400 MHz, CDCl₃, rotameric broadening): 9.06-9.01 (m, 1H), 8.98-8.94 (m, 1H), 8.85-8.78 (m, 1H), 8.54-8.47 (m, 1H), 8.35 (dd, J=8.5, 1.3 Hz, 1H), 7.90-7.84 (m, 1H), 7.84 (d, J=1.8 Hz, 1H), 7.38-7.31 (m, 1H), 7.10 (dd, J=8.1, 1.7 Hz, 1H), 6.92-6.80 (m, 1.5H), 6.78-6.68 (m, 1H), 6.64-6.60 (m, 0.25H), 6.39-6.33 (m, 0.25H), 4.42-4.31 (m, 2H), 3.93-3.90 (m, 1H), 3.70-3.55 (m, 1H), 3.15-3.07 (m, 1H), 2.90-2.82 (m, 2H), 1.87-1.78 (m, 0.5H), 1.58-1.49 (m, 0.5H).

Example 25

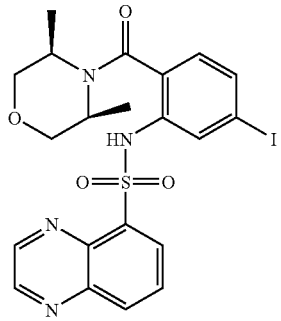

(R,S)-Quinoxaline-5-sulfonic acid [2-(3,5-dimethylmorpholine-4-carbonyl)-5-iodophenyl]-amide.

A. (S,S)-3,5-Dimethylmorpholine-4-carboxylic acid tert-butyl ester and (S,R)-meso-3,5-Dimethylmorpholine-4-carboxylic acid tert-butyl ester. A mixture of (S)-2-aminopropan-1-ol (8.5 g, 110 mmol), hydroxyacetone (10.9 g, 147 mmol), and PtO₂ (0.10 g, 0.44 mmol) was combined with methanol (200 mL) in a 1 L Parr bottle. The reaction vessel was placed on a Parr shaker for 14 h under an atmosphere of 30 psi of hydrogen. The catalyst was removed by filtration through a pad of diatomaceous earth, rinsing with excess methanol. The filtrate was concentrated in vacuo to provide a mixture of diastereomeric aminodiols as a viscous yellow liquid [7:5 (S,S):(S,R) based on crude ¹H NMR]. The crude diol mixture (5.0 g, 37.5 mmol) was stirred in a 150 mL thick-walled sealable reaction vessel as 40 mL concentrated H₂SO₄ was added slowly (significant exotherm observed). The vessel was sealed and heated at 140° C. for 7 h. The dark brown mixture was poured into 100 mL crushed ice, and the flask was rinsed into the reaction mixture with 50 mL of H₂O. The resulting mixture was cooled in an ice bath and made basic by the slow addition of 10 N NaOH. The aqueous mixture was extracted with diethyl ether (3×300 mL). Salts began to precipitate from the aqueous layer. The aqueous layer was filtered through a sintered glass funnel, and the precipitated salts were washed with H₂O (100 mL). The aqueous filtrate was further extracted with diethyl ether (6×200 mL). The combined organic layers were dried (MgSO₄) and concentrated in vacuo to give a mixture of cis- and trans-dimethylmorpholines as an orange liquid (1.8 g, 41%). To a mixture of the unpurified dimethylmorpholine isomers (1.8 g, 16 mmol), NaOH (1.2 g, 30 mmol), and H₂O (7 mL) was added di-tert-butyl-dicarbonate (3.2 g, 15 mmol) in one portion at room temperature. The mixture was stirred overnight, then was poured into H₂O (30 mL) and extracted with diethyl ether (3×30 mL). The combined organic layers were dried (MgSO₄) and concentrated in vacuo to give the mixture of Boc-protected morpholines as an orange liquid. The diastereomers were separated by flash chromatography (EtOAc/petroleum ether) to provide (S,S)-3,5-dimethylmorpholine-4-carboxylic acid tert-butyl ester (2.0 g, 59%). TLC (10% EtOAc/petroleum ether): $R_f$=0.41. ¹H NMR (500 MHz, CDCl₃): 3.85-3.78 (m, 4H), 3.49-3.43 (m, 2H), 1.47 (s, 9H), 1.29 (d, J=6.4 Hz, 6H). In addition, (S,R)-meso-3,5-dimethylmorpholine-4-carboxylic acid tert-butyl ester (0.90 g, 27%) was obtained. TLC (10% EtOAc/petroleum ether): $R_f$=0.33. ¹H NMR (500 MHz, CDCl₃): 3.93 (dq, J=7.0, 3.9 Hz, 2H), 3.70 (d, J=11.5 Hz, 2H), 3.55 (dd, J=11.5, 3.9 Hz, 2H), 1.47 (s, 9H), 1.30 (d, J=7.0 Hz, 6H).

B. (S,S)-3,5-Dimethylmorpholine. Hydrogen chloride gas was bubbled into a stirred solution of. (S,S)-3,5-dimethylmorpholine-4-carboxylic acid tert-butyl ester (2.0 g, 9.2 mmol) in methanol (20 mL) at 0° C. over a 10 min period. The reaction was allowed to stir for 20 min at 0° C. then for 5 h at room temperature. The methanol was removed in vacuo, and the residue was partitioned between diethyl ether and 2 N NaOH. The layers were separated, and the aqueous layer was extracted with diethyl ether (4×). The combined organic layers were dried (MgSO₄) and concentrated in vacuo to give the title morpholine as a yellow oil (0.64 g, 61%). ¹H NMR (500 MHz, CDCl₃): 3.70 (dd, J=11.0, 3.1 Hz, 2H), 3.31 (dd, J=11.0, 5.7 Hz, 2H), 3.20-3.12 (m, 2H), 1.47 (br s, 1H), 1.12 (d, J=6.7 Hz, 6H).

C. (S,R)-meso-3,5-Dimethylmorpholine. Hydrogen chloride gas was bubbled into a stirred solution of (S,R)-meso-3,5-dimethylmorpholine-4-carboxylic acid tert-butyl ester (0.90 g, 4.2 mmol) in methanol (20 mL) at 0° C. over a 10 min period. The reaction was allowed to stir for 20 min at 0° C. then for 5 h at room temperature. The methanol was removed in vacuo, and the residue was partitioned between diethyl ether and 2 N NaOH. The layers were separated, and the aqueous layer was extracted with diethyl ether (4×). The combined organic layers were dried (MgSO₄) and concentrated in vacuo to give the title morpholine as a yellow oil. ¹H NMR (500 MHz, CDCl₃): 3.78-3.68 (m, 2H), 3.02-2.92 (m, 4H), 1.50 (br s, 1H), 0.97 (d, J=7.5 Hz, 6H).

D. (R,S)-Quinoxaline-5-sulfonic acid [2-(3,5-dimethylmorpholine-4-carbonyl)-5-iodophenyl]-amide. A suspension of 4-iodo-2-(quinoxaline-5-sulfonylamino)benzoic acid (EXAMPLE 4, Step D; 0.050 g, 0.14 mmol) was heated at reflux in thionyl chloride (5 mL) for 30 min. The reaction became homogeneous. The thionyl chloride was removed in vacuo, and the residue was re-concentrated from toluene (3×) to remove residual thionyl chloride. The acid chloride was obtained as an off-white solid. The acid chloride was stirred in toluene (5 mL) at 90° C. with (S,R)-meso-3,5-dimethylmorpholine (50 mg, 0.43 mmol) for 1 h. The reaction mixture was poured into 1 N HCl and extracted with DCM (3×). The combined organic layers were dried (Na₂SO₄) and concentrated. The residue was purified by flash chromatography (EtOAc/hexanes) to provide 32 mg (50%) of the desired amide as a solid. MS (ESI): mass calculated for $C_{21}H_{21}IN_4O_4S$, 552.0; m/z found, 551 [M−H]⁻. HPLC (reverse phase): $R_T$=8.77 min. ¹H NMR (400 MHz, CDCl₃, rotameric broadening): 9.04 (d, J=1.8 Hz, 1H), 9.00 (d, J=1.8 Hz, 1H), 8.58 (br s, 1H), 8.56 (dd, J=7.0, 1.5 Hz, 1H), 8.38 (dd, J=8.4, 1.4 Hz, 1H), 7.93 (dd, J=8.4, 7.4 Hz, 1H), 7.81 (d, J=1.4 Hz, 1H), 7.38 (dd, J=8.0, 1.6 Hz, 1H), 6.84 (d, J=8.0 Hz, 1H), 4.15-4.02 (br m, 2H), 3.74 (d, J=11.6 Hz, 2H), 3.56 (dd, J=11.5, 3.6 Hz, 2H), 1.34 (d, J=7.0 Hz, 6H).

Example 26

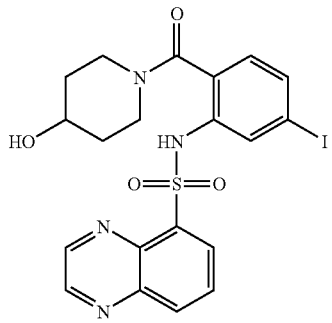

Quinoxaline-5-sulfonic acid [2-(4-hydroxy-piperidine-1-carbonyl)-5-iodo-phenyl]-amide.

The title compound was prepared from the HATU-mediated coupling of 4-iodo-2-(quinoxaline-5-sulfonylamino)benzoic acid (EXAMPLE 4, Step D) and 4-hydroxypiperidine and purified as described in EXAMPLE 1, Step K. MS (ESI): mass calculated for $C_{20}H_{19}IN_4O_4S$, 538.0; m/z found, 539 [M+H]. HPLC (reverse phase): $R_T$=7.77 min. $^1$H NMR (400 MHz, CDCl$_3$, rotameric broadening): 9.07 (d, J=1.8 Hz, 1H), 9.02 (d, J=1.8 Hz, 1H), 8.90 (br s, 1H), 8.50 (dd, J=7.0, 1.5 Hz, 1H), 8.37 (dd, J=8.4, 1.4 Hz, 1H), 7.95 (d, J=1.5 Hz, 1H), 7.89 (dd, J=8.4, 7.4 Hz, 1H), 7.39 (dd, J=8.0, 1.6 Hz, 1H), 6.77 (d, J=8.0 Hz, 1H), 3.94-3.90 (m, 1H), 3.80-3.75 (m, 1H), 3.2-2.8 (m, 3H), 2.05-2.01 (m, 2H), 1.7-1.3 (m, 3H).

Example 27

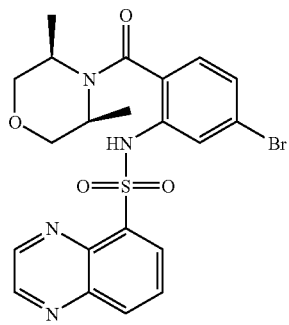

meso-Quinoxaline-5-sulfonic acid [2-(3,5-dimethyl-morpholine-4-carbonyl)-5-bromophenyl]-amide.

The title compound was prepared and purified as described in EXAMPLE 25, Step D from (S,R)-meso-3,5-dimethylmorpholine and 4-bromo-2-(quinoxaline-5-sulfonylamino)-benzoic acid (EXAMPLE 1, Step G). MS (ESI): mass calculated for $C_{21}H_{21}BrN_4O_4S$, 504.0; m/z found, 503/505 [M-H]$^-$. HPLC (reverse phase): $R_T$=8.67 min. $^1$H NMR (400 MHz, CDCl$_3$, rotameric broadening): 9.04 (d, J=1.8 Hz, 1H), 9.00 (d, J=1.8 Hz, 1H), 8.64 (br s, 1H), 8.56 (dd, J=7.0, 1.5 Hz, 1H), 8.38 (dd, J=8.4, 1.4 Hz, 1H), 7.92 (dd, J=8.4, 7.4 Hz, 1H), 7.63 (d, J=1.7 Hz, 1H), 7.18 (dd, J=8.1, 1.8 Hz, 1H), 6.99 (d, J=8.1 Hz, 1H), 4.18-4.02 (br m, 2H), 3.76-3.73 (m, 2H), 3.58 (dd, J=11.7, 3.6 Hz, 2H), 1.35 (d, J=7.0 Hz, 6H).

Example 28

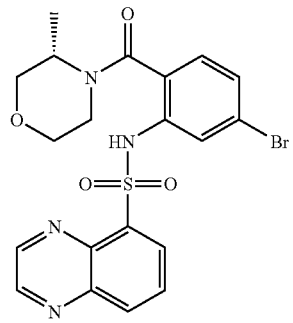

(S)-Quinoxaline-5-sulfonic acid [5-bromo-2-(3-methylmorpholine-4-carbonyl)-phenyl]-amide.

The title compound was prepared from the HATU-mediated coupling of 4 bromo-2-(quinoxaline-5-sulfonylamino)benzoic acid (EXAMPLE 1, Step G) and (S)-3-methylmorpholine (EXAMPLE 23, Step A) and purified as described in EXAMPLE 1, Step K. MS (ESI): mass calculated for $C_{20}H_{19}BrN_4O_4S$, 490.0; m/z found, 489/491 [M-H]$^-$. HPLC (reverse phase): $R_T$=8.36 min. $^1$H NMR (400 MHz, CDCl$_3$, rotameric broadening): 9.05 (d, J=1.8 Hz, 1H), 9.01 (br s, 1H), 9.00 (d, J=1.8 Hz, 1H), 8.56 (dd, J=7.0, 1.5 Hz, 1H), 8.37 (dd, J=8.4, 1.4 Hz, 1H), 7.91 (dd, J=8.4, 7.4 Hz, 1H), 7.72 (d, J=1.4 Hz, 1H), 7.16 (dd, J=8.0, 1.6 Hz, 1H), 6.94 (d, J=8.0 Hz, 1H), 4.30 (br m, 1H), 3.91-3.82 (m, 1H), 3.68-3.63 (m, 1H), 3.50 (dd, J=11.5, 2.7 Hz, 1H), 3.38-3.22 (m, 2H), 1.35-1.15 (br m, 3H), 1.0-0.9 (m, 1H).

Example 29

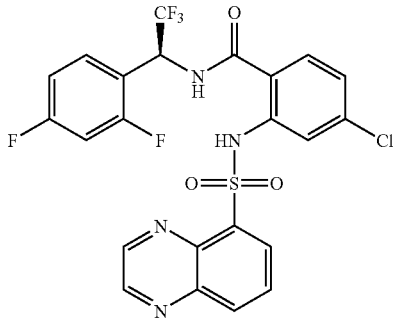

(S)-4-Chloro-N-[1-(2,4-difluoro-phenyl)-2,2,2-trifluoroethyl]-2-(quinoxaline-5-sulfonylamino)-benzamide.

A. S—(R)-2-Methylpropane-2-sulfinic acid 2,4-difluorobenzylideneamide. A suspension of 2,4-difluorobenzaldehyde (0.61 g, 4.3 mmol), (S)-tert-butanesulfinamide (0.47 g, 3.9 mmol), and powdered anhydrous CUSO$_4$ (1.2 g, 7.8 mmol) was stirred in DCM (8 mL) overnight. The reaction mixture was filtered, and the filter cake was washed with DCM. The filtrate was concentrated in vacuo to give the crude. N-sulfinyl imine as a viscous yellow oil. Purification by flash chromatography (EtOAc/hexanes) provided 0.81 g (84%) of the N-sulfinyl imine as a pale yellow viscous oil. $^1$H NMR (400 MHz, CDCl$_3$): 8.83 (s, 1H), 8.05-7.99 (m, 1H), 7.01-6.96 (m, 1H), 6.94-6.87 (m, 1H), 1.27 (s, 9H).

B. S—(R)-2-Methylpropane-2-sulfinic acid [1-(S)-(2,4-difluorophenyl)-2,2,2-trifluoroethyl]-amide. To a solution of S—(R)-2-methylpropane-2-sulfinic acid 2,4-difluorobenzylideneamide (0.32 g, 1.3 mmol) and tetrabutylammonium difluorotriphenylsilicate (TBAT, 770 mg, 1.4 mmol) in THF (20 mL) at −55° C. was added a solution of trifluoromethyl trimethylsilane (222 mg, 1.56 mmol) in THF (5 mL). The reaction was allowed to stir for 1 h at −55° C., and then was allowed to warm slowly to room temperature overnight. The reaction was quenched with 20 mL satd. aq. NH$_4$Cl and extracted with 3×20 mL EtOAc. The combined organic layers were dried (MgSO$_4$) and concentrated in vacuo. The crude residue was purified by flash chromatography (EtOAc/hexanes) to provide recovered starting N-sulfinyl imine (166 mg, 52%) and the desired trifluoromethylated adduct as a colorless liquid (126 mg, 31%, 90% de). Major diastereomer: $^1$H NMR (500 MHz, CDCl$_3$): 7.41-7.35 (m, 1H), 6.98-6.93 (m, 1H), 6.93-6.87 (m, 1H), 5.12-5.05 (m, 1H), 3.86 (br d, J=7.9 Hz, 1H), 1.26 (s, 9H).

C. (S)-1-(2,4-Difluorophenyl)-2,2,2-trifluoroethylamine hydrochloride. To a stirred solution of the above sulfinamide (90% de, 0.13 g, 0.40 mmol) in methanol (10 mL) at room temperature was added 2 mL of a satd. solution of HCl (g) in methanol. The reaction mixture was allowed to stir for 2 h at room temperature. The mixture was concentrated in vacuo until the amine hydrochloride salt began to precipitate, and then diethyl ether (20 mL) was added to fully precipitate the salt. The hydrochloride salt was collected by suction filtration, washed with diethyl ether, and dried in vacuo to provide fine white crystals (62 mg, 63%, 90% ee based on the de of the starting material). $^1$H NMR (500 MHz, CD$_3$OD): 7.70-7.63 (m, 1H), 7.28-7.19 (m, 2H), 5.59 (q, J=7.3 Hz, 1H).

D. (S)-4-Chloro-N-[1-(2,4-difluorophenyl)-2,2,2-trifluoroethyl]-2-(quinoxaline-5-sulfonylamino)-benzamide. The title compound was prepared from the HATU-mediated coupling of 4-chloro-2-(quinoxaline-5-sulfonylamino)benzoic acid (EXAMPLE 3, Step B) and (S)-1-(2,4-difluorophenyl)-2,2,2-trifluoroethylamine hydrochloride and purified as described in EXAMPLE 1, Step K. MS (ESI): mass calculated for C$_{23}$H$_{14}$ClF$_5$N$_4$O$_3$S, 556.0; m/z found, 555/557 [M−H]$^-$. HPLC (reverse phase): R$_T$=9.98 min. $^1$H NMR (400 MHz, CDCl$_3$): 11.07 (s, 1H), 8.84-8.83 (m, 2H), 8.56 (dd, J=7.4, 1.4 Hz, 1H), 8.31 (dd, J=7.4, 1.4 Hz, 1H), 7.87 (dd, J=8.4, 7.4 Hz, 1H), 7.81 (d, J=2.0 Hz, 1H), 7.43-7.37 (m, 1H), 7.30 (d, J=8.5 Hz, 1H), 7.03-6.93 (m, 3H), 6.81-6.79 (m, 1H), 6.08-6.00 (m 1H).

Example 30

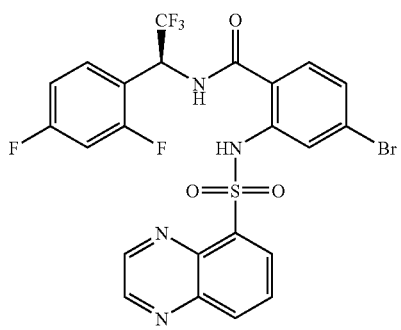

(S)-4-Bromo-N-[1-(2,4-difluoro-phenyl)-2,2,2-trifluoroethyl]-2-(quinoxaline-5-sulfonylamino)-benzamide.

The title compound was prepared from the HATU-mediated coupling of 4-bromo-2-(quinoxaline-5-sulfonylamino)benzoic acid (EXAMPLE 1, Step G) and. (S)-1-(2,4-difluorophenyl)-2,2,2-trifluoroethylamine hydrochloride (EXAMPLE 29, Step C) and purified as described in EXAMPLE 1, Step K. MS (ESI): mass calculated for C$_{23}$H$_{14}$BrF$_5$N$_4$O$_3$S, 600.0; m/z found, 599/601 [M−H]$^-$. HPLC (reverse phase): R$_T$=10.06 min. $^1$H NMR (400 MHz, CDCl$_3$): 11.02 (s, 1H), 8.84-8.83 (m, 2H), 8.56 (dd, J=7.4, 1.4 Hz, 1H), 8.31 (dd, J=7.4, 1.4 Hz, 1H), 7.96 (d, J=2.0 Hz, 1H), 7.87 (dd, J=8.4, 7.4 Hz, 1H), 7.43-7.37 (m, 1H), 7.22 (d, J=8.5 Hz, 1H), 7.13 (dd, J=8.5, 1.8 Hz, 1H), 7.03-6.93 (m, 2H), 6.82-6.80 (m, 1H), 6.06-5.99 (m, 1H).

Example 31

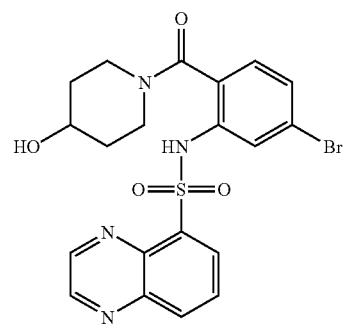

Quinoxaline-5-sulfonic acid [2-(4-hydroxy-piperidine-1-carbonyl)-5-bromo-phenyl]-amide.

The title compound was prepared from the HATU-mediated coupling of 4-bromo-2-(quinoxaline-5-sulfonylamino)benzoic acid (EXAMPLE 1, Step G) and 4-hydroxypiperidine and purified as described in EXAMPLE 1, Step K. MS (ESI): mass calculated for C$_{20}$H$_{19}$BrN$_4$O$_4$S, 490.0; m/z found, 491/493 [M+H]$^+$, 513/515 [M+Na]$^+$. HPLC (reverse phase): R$_T$=7.68 min. $^1$H NMR (400 MHz, CDCl$_3$, rotameric broadening): 9.08 (d, J=1.8 Hz, 1H), 9.02 (d, J=1.8 Hz, 1H), 8.95 (br s, 1H), 8.52-8.50 (m, 1H), 8.38-8.36 (m, 1H), 7.92-7.88 (m, 1H), 7.75 (d, J=1.6 Hz, 0.7H), 7.68 (d, J=1.6 Hz, 0.3H), 7.20-7.17 (m, 1H), 6.96-6.92 (m, 1H), 3.96-3.91 (m, 1H), 3.85-3.75 (m, 1H), 3.2-2.8 (m, 3H), 2.05-1.95 (m, 2H), 1.7-1.3 (m, 3H).

Example 32

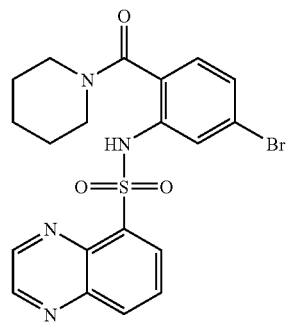

Quinoxaline-5-sulfonic acid [5-bromo-2-(piperidine-1-carbonyl)-phenyl]-amide.

The title compound was prepared and purified by the HATU-mediated coupling of 4-bromo-2-(quinoxaline-5-sulfonylamino)benzoic acid (EXAMPLE 1, Step G) and piperidine as described by the general procedure in EXAMPLE 1, Step K. MS (ESI): mass calculated for $C_{20}H_{19}BrN_4O_3S$, 474.0; m/z found, 475/477 [M+H]$^+$, 497/499 [M+Na]$^+$. HPLC (reverse phase): $R_T$=9.19 min. $^1$H NMR (500 MHz, CDCl$_3$, rotameric broadening): 9.07 (d, J=1.8 Hz, 1H), 9.05 (br s, 1H), 9.00 (d, J=1.8 Hz, 1H), 8.49 (dd, J=7.0, 1.5 Hz, 1H), 8.34 (dd, J=8.4, 1.4 Hz, 1H), 7.87 (dd, J=8.4, 7.4 Hz, 1H), 7.84 (d, J=1.5 Hz, 1H), 7.15 (dd, J=8.0, 1.6 Hz, 1H), 6.89 (d, J=8.0 Hz, 1H), 3.40-3.20 (br m, 2H), 2.92-2.80 (br m, 2H), 1.55-1.25 (br m, 6H).

Example 33

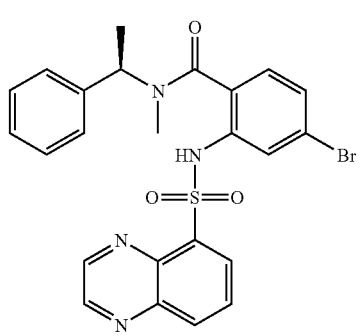

(R)-4-Bromo-N-methyl-N-(1-phenyl-ethyl)-2-(quinoxaline-5-sulfonylamino)-benzamide.

The title compound was prepared and purified by the HATU-mediated coupling of 4-bromo-2-(quinoxaline-5-sulfonylamino)benzoic acid (EXAMPLE 1, Step G) and (R)-N-methyl(1-phenylethyl)amine as described by the general procedure in EXAMPLE 1, Step K. MS (ESI): mass calculated for $C_{24}H_{21}BrN_4O_3S$, 524.0; m/z found, 523/525 [M–H]$^-$. HPLC (reverse phase): $R_T$=9.75 min. $^1$H NMR (500 MHz, CDCl$_3$, mixture of rotamers): 9.07-8.94 (m, 3H), 8.59 (br d, J=7.3 Hz, 1H), 8.37 (br d, J=8.4 Hz, 1H), 7.93 (m 1H), 7.77-7.68 (m, 1H), 7.42-7.35 (m, 3H), 7.33-7.30 (m, 1H), 7.13-7.10 (m, 1H), 7.00-6.98 (m, 1H), 6.15-6.05 (m, 0.5H), 5.05-4.90 (m, 0.5H), 3.0-2.5 (m, 3H), 1.6-1.5 (m, 3H), (one H not observed).

Example 34

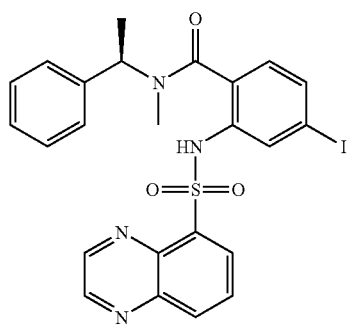

(R)-4-Iodo-N-methyl-N-(1-phenyl-ethyl)-2-(quinoxaline-5-sulfonylamino)-benzamide.

The title compound was prepared and purified by the HATU-mediated coupling of 4-iodo-2-(quinoxaline-5-sulfonylamino)benzoic acid (EXAMPLE 4, Step D) and (R)-N-methyl(1-phenylethyl)amine as described by the general procedure in EXAMPLE 1, Step K. MS (ESI): mass calculated for $C_{24}H_{21}IN_4O_3S$, 572.0; m/z found, 571 [M–H]$^-$. HPLC (reverse phase): $R_T$=9.81 min. $^1$H NMR (500 MHz, CDCl$_3$, mixture of rotamers): 9.08-8.98 (m, 2H), 9.00-8.92 (m, 1H), 8.62-8.58 (m, 1H), 8.40-8.32 (m, 1H), 7.98-7.90 (m, 2H), 7.42-7.35 (m, 3H), 7.35-7.27 (m, 2H), 6.87-6.80 (m, 1H), 6.15-6.05 (m, 0.5H), 5.02-4.92 (m, 0.5H), 3.0-2.5 (m, 3H), 1.6-1.5 (m, 3H), (one H not observed).

Example 35

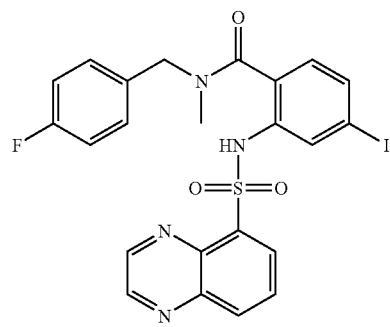

N-(4-Fluorobenzyl)-4-iodo-N-methyl-2-(quinoxaline-5-sulfonylamino)-benzamide.

The title compound was prepared and purified by the HATU-mediated coupling of 4-iodo-2-(quinoxaline-5-sulfonylamino)benzoic acid (EXAMPLE 4, Step D) and N-methyl-4-fluorobenzylamine as described by the general procedure in EXAMPLE 1, Step K. MS (ESI): mass calculated for $C_{23}H_{18}FIN_4O_3S$, 576.0; m/z found, 575 [M–H]$^-$. HPLC (reverse phase): $R_T$=9.65 min. $^1$H NMR (500 MHz, CDCl$_3$, 2:1 mixture of rotamers): 9.0-8.9 (m, 3H), 8.58-8.51 (m, 1H), 8.39-8.37 (m, 1H), 7.96 (s, 1H), 7.95-7.88 (m, 1H), 7.3-7.2 (m, 3H), 7.06-7.02 (m, 3H), 4.40-4.35 (m, 1.3H), 4.22-4.14 (m, 0.7H), 2.85-2.79 (m, 1H), 2.52-2.46 (m, 2H).

Example 36

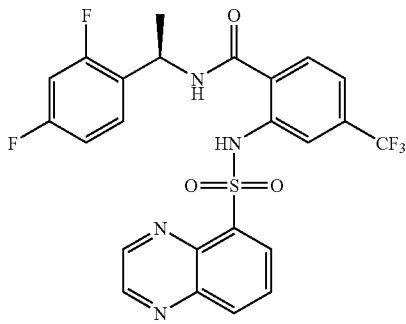

(R)-N-[1-(2,4-Difluorophenyl)ethyl]-2-(quinoxaline-5-sulfonylamino)-4-trifluoromethyl-benzamide.

A. 2-Nitro-4-trifluoromethylbenzoic acid methyl ester. To a stirred solution of 2-nitro-4-trifluoromethylbenzoic acid (4.3 g, 0.018 mol) in DMF (10 mL) was added DBU (5.4 mL, 0.036 mol) under a nitrogen atmosphere. The reaction mixture was stirred for 15 min after which iodomethane (2.2 mL, 0.036 mol) was added at 0° C. The mixture was warmed to room temperature and stirred overnight. The mixture was diluted with EtOAc (60 mL) and washed with H$_2$O (3×). The organic layer was dried over MgSO$_4$, filtered, concentrated, and purified by flash chromatography (hexanes/EtOAc) to provide the title compound (4.30 g, 96%). TLC (silica, 50% EtOAc/hexanes): R$_f$=0.55. $^1$H NMR (500 MHz, CDCl$_3$): 8.22 (s, 1H), 7.96 (d, J=7.5 Hz, 1H), 7.88 (d, J=8.0 Hz, 1H), 3.97 (s, 3H).

B. 2-Amino-4-trifluoromethyl-benzoic acid methyl ester. A solution of 2-nitro-4-trifluoromethylbenzoic acid methyl ester (4.3 g, 0.017 mol) was dissolved in a mixture of DCM (20 mL) and EtOAc (20 mL) followed by addition of SnCl$_2$·2H$_2$O (19 g, 0.086 mol). The mixture was stirred overnight at room temperature, then was neutralized by shaking with a satd. aq. NaHCO$_3$ solution. The resulting salts were removed by filtration through a pad of diatomaceous earth. The filtrate was extracted with DCM (3×). The combined organic layers were dried over MgSO$_4$, filtered, and concentrated in vacuo to provide the title compound (3.38 g, 91%). TLC (silica, 50% EtOAc/hexanes): R$_f$=0.60. HPLC (reverse phase): R$_T$=9.31 min. $^1$H NMR (500 MHz, CDCl$_3$): 7.95 (d, J=8.3 Hz, 1H), 6.90 (s, 1H), 6.84 (d, J=9.3 Hz, 1H), 5.91 (br s, 2H), 3.90 (s, 3H).

C. 2-(Benzo[1,2,5]thiadiazole-4-sulfonylamino)-4-trifluoromethylbenzoic acid methyl ester. 4-Chlorosulfonyl-2,1,3-benzothiadiazole (1.77 g, 7.52 mmol) was added to a solution of 2-amino-4-trifluoromethylbenzoic acid methyl ester (1.50 g, 6.84 mmol) and pyridine (1.10 mL, 13.7 mmol) in DCM (10 mL). After standing overnight at room temperature, the reaction mixture was quenched with 1 N HCl and diluted with H$_2$O. The aqueous layer was extracted with DCM (3×). The combined organic layers were dried over MgSO$_4$, filtered, concentrated, and purified by flash chromatography (hexanes/EtOAc) to provide the title compound (1.78 g, 62%). TLC (silica, 50% EtOAc/hexanes): R$_f$=0.47. MS (ESI): mass calculated for C$_{15}$H$_{10}$F$_3$N$_3$O$_4$S$_2$, 417.01; m/z found, 415.9/416.9/417.9 [M−H]$^−$. HPLC (reverse phase): R$_T$=9.95 min. $^1$H NMR (500 MHz, CDCl$_3$): 11.33 (s, 1H), 8.41 (dd, J=7.1, 1.0 Hz, 1H), 8.23 (dd, J=8.9, 1.0 Hz, 1H), 8.04 (s, 1H), 7.98 (d, J=8.2 Hz, 1H), 7.72 (dd, J=8.8, 7.1 Hz, 1H), 7.20 (dd, J=8.3, 1.1 Hz, 1H), 3.96 (s, 3H).

D. 2-(Quinoxaline-5-sulfonylamino)-4-trifluoromethyl-benzoic acid methyl ester. Zinc powder (2.00 g, 30.7 mmol) was added to a mixture of 2-(benzo[1,2,5]thiadiazole-4-sulfonylamino)-4-trifluoromethylbenzoic acid methyl ester (1.28 g, 3.07 mmol) and AcOH (20 mL), and the resulting mixture was heated at 50° C. for 2 h with vigorous stirring. The mixture was filtered through a pad of diatomaceous earth, rinsed with methanol, and concentrated to a yellow solid. This material was dissolved in methanol (15 mL) and added to a mixture of glyoxal sodium bisulfite adduct (2.46 g, 9.24 mmol), AcOH (0.9 mL), NaOAc (0.25 g, 3.98 mmol), and H$_2$O (4.5 mL). The reaction mixture was heated at reflux for 3 h, then was allowed to come to room temperature, diluted with DCM, filtered through a pad of diatomaceous earth, and rinsed with DCM. The filtrate was washed with H$_2$O, dried over MgSO$_4$, concentrated, and purified by flash chromatography (hexanes/EtOAc) to provide title compound (0.70 g, 56%). TLC (silica, 50% EtOAc/hexanes): R$_f$=0.24. $^1$H NMR (500 MHz, CDCl$_3$): 11.38 (s, 1H), 8.95 (dd, J=7.7, 1.8 Hz, 2H), 8.62. (dd, J=7.4, 1.4 Hz, 1H), 8.33 (dd, J=8.5, 1.3 Hz, 1H), 8.14 (s, 1H), 7.95 (d, J=8.3 Hz, 1H), 7.88 (dd, J=8.4, 7.5 Hz, 1H), 7.17 (dd, J=8.3, 1.2 Hz, 1H), 3.94 (s, 3H).

E. 2-(Quinoxaline-5-sulfonylamino)-4-trifluoromethyl-benzoic acid. To a stirred solution of 2-(quinoxaline-5-sulfonylamino)-4-trifluoromethyl-benzoic acid methyl ester (0.86 g, 2.1 mmol) in THF (10 mL) and H$_2$O (5 mL) was added LiOH·H$_2$O (0.44 g, 10.4 mmol). The reaction mixture was stirred at room temperature overnight. The solution was acidified to pH ~2 with concentrated HCl and diluted with H$_2$O. The aqueous layer was extracted with DCM (3×). The combined organic layers were dried over MgSO$_4$, filtered, and concentrated in vacuo to provide the title compound (0.81 g, 98%). MS (ESI): mass calculated for C$_{16}$H$_{10}$F$_3$N$_3$O$_4$S, 397.03; m/z found, 396/397/398 [M−H]$^−$. HPLC (reverse phase): R$_T$=8.76 min. $^1$H NMR (400 MHz, CDCl$_3$): 11.35 (s, 1H), 8.96 (dd, J=4.7, 1.8 Hz, 1H), 8.64 (dd, J=7.4, 1.4 Hz, 1H), 8.35 (dd, J=8.5, 1.3 Hz, 1H), 8.16 (s, 1H), 8.05 (d, J=8.3 Hz, 1H), 7.90 (dd, J=8.4, 7.4 Hz, 1H), 7.21 (dd, J=7.8, 1.0 Hz, 1H).

F. (R)-N-[1-(2,4-Difluorophenyl)ethyl]-2-(quinoxaline-5-sulfonylamino)-4-trifluoromethylbenzamide. To a solution of 2-(quinoxaline-5-sulfonylamino)-4-trifluoromethyl-benzoic acid (0.028 g, 0.071 mmol) in DMF (0.40 mL) at room temperature was added pyridine (0.017 mL, 0.21 mmol) followed by HATU (0.053 g, 0.14 mmol). The reaction mixture was agitated for 1 h on a shaker. (R)-1-(2,4-Difluorophenyl)ethylamine hydrochloride (EXAMPLE 2, Method 1, Step C; 0.027 g, 0.14 mmol) was added followed by Hünig's base (0.024 mL, 0.14 mmol). The reaction mixture was agitated for 2 h. TFA (0.10 mL) was added to quench the reaction. The mixture was diluted with DMF (1 mL) and the product amide was obtained by purification of the entire reaction mixture by preparative reverse-phase chromatography. The title amide was obtained as a solid (8 mg, 21%). MS (ESI): mass calculated for C$_{24}$H$_{17}$F$_5$N$_4$O$_3$S, 536.09; m/z found, 537/538/539 [M+H]$^+$. HPLC (reverse phase): R$_T$=9.81 min. $^1$H NMR (400 MHz, CDCl$_3$): 11.18 (s, 1H), 8.85 (d, J=1.8 Hz, 1H), 8.81 (d, J=1.8 Hz, 1H), 8.56 (dd, J=7.4, 1.4 Hz, 1H), 8.30 (dd, J=8.5, 1.4 Hz, 1H), 8.04 (s, 1H), 7.86 (dd, J=8.4, 7.4 Hz, 1H), 7.42 (d, 7.42, 1H), 7.32-7.27 (m, 1H), 7.19 (dd, J=8.1, 1.1 Hz, 1H), 6.91-6.82 (m, 2H), 6.43 (d, J=7.5 Hz, 1H), 5.36-5.29 (m, 1H), 1.55 (d, J=7.0 Hz, 3H).

Example 37

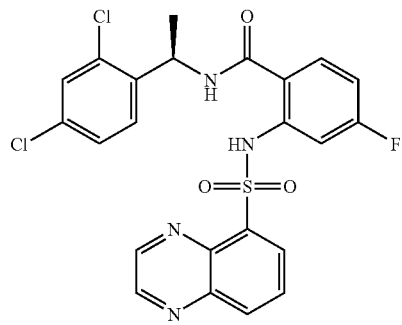

(R)-N-[1-(2,4-Dichlorophenyl)-ethyl]-4-fluoro-2-(quinoxaline-5-sulfonylamino)-benzamide.

A. 2-(Benzo[1,2,5]thiadiazole-4-sulfonylamino)-4-fluorobenzoic acid methyl ester. 4-Chlorosulfonyl-2,1,3-benzothiadiazole (1.40 g, 5.94 mmol) was added to a solution of 2-amino-4-fluorobenzoic acid methyl ester (0.67 g, 4.0 mmol) and pyridine (0.64 mL, 7.9 mmol) in DCM. (5 mL). After standing overnight at room temperature the reaction mixture was quenched with 1 N HCl and diluted with H$_2$O. The aqueous layer was extracted with DCM (3×). The combined organic layers were dried over MgSO$_4$, filtered, concentrated, and purified by silica gel chromatography (hexanes/EtOAc) to provide the title compound (1.26 g, 87%). TLC (silica, 50% EtOAc/hexanes): R$_f$=0.47. MS (ESI): mass calculated for C$_{14}$H$_{10}$FN$_3$O$_4$S$_2$, 367.01; m/z found, 366/367/368 [M–H]$^-$. HPLC (reverse phase): R$_T$=9.52 min. $^1$H NMR (500 MHz, CDCl$_3$): 11.50 (s, 1H), 8.40 (dd, J=7.1, 1.0 Hz, 1H), 8.23 (d, J=8.3 Hz, 1H), 7.89 (dd, J=8.9, 6.4 Hz, 1H), 7.73 (dd, J=8.8, 7.1 Hz, 1H), 7.47 (dd, J=11.1, 2.5 Hz, 1H), 6.67-6.63 (m, 1H), 3.92 (s, 3H).

B. 4-Fluoro-2-(quinoxaline-5-sulfonylamino)benzoic acid methyl ester. Zinc powder (2.24 g, 34.3 mmol) was added to a mixture of 2-(benzo[1,2,5]thiadiazole-4-sulfonylamino)-4-fluorobenzoic acid methyl ester (1.26 g, 3.43 mmol) and AcOH (20 mL). The resulting mixture was heated to 50° C. for 2 h with vigorous stirring. The mixture was filtered through a pad of diatomaceous earth, rinsing with methanol, and was concentrated to a yellow solid. This material was dissolved in methanol (15 mL) and added to a mixture of glyoxal sodium bisulfite adduct (2.72 g, 10.2 mmol), AcOH (0.9 mL), NaOAc (0.28 g, 3.42 mmol), and H$_2$O (4.5 mL). The reaction was allowed to proceed at reflux for 3 h. The resulting mixture was diluted with DCM and filtered through a pad of diatomaceous earth, rinsing with DCM. The filtrate was washed with H$_2$O, dried over MgSO$_4$, concentrated, and purified by flash chromatography (hexanes/EtOAc) to provide the title compound (0.18 g, 15%). TLC (silica, 50% EtOAc/hexanes): R$_f$=0.20. MS (ESI): mass calculated for C$_{16}$H$_{12}$FN$_3$O$_4$S, 361.05; m/z found, 360/361/362 [M–H]$^-$. HPLC (reverse phase): R$_T$=9.12 min. $^1$H NMR (500 MHz, CDCl$_3$): 11.53 (s, 1H), 8.96 (dd, J=16.6, 1.6 Hz, 2H), 8.61 (dd, J=7.4, 1.4 Hz, 1H), 8.33 (dd, J=8.5, 1.4 Hz, 1H), 7.89-7.85 (m, 2H), 7.57 (dd, J=11.4, 2.5 Hz, 1H), 6.63-6.59 (m, 1H), 3.90 (s, 3H).

C. 4-Fluoro-2-(quinoxaline-5-sulfonylamino)benzoic acid. To a stirred solution of 4-fluoro-2-(quinoxaline-5-sulfonylamino)benzoic acid methyl ester (0.18 g, 0.50 mmol) in THF (4 mL) and H$_2$O (2 mL) was added LiOH.H$_2$O (0.10 g, 2.50 mmol). The reaction mixture was stirred at room temperature overnight. The solution was acidified to pH ~2 with concentrated HCl and diluted with H$_2$O. The aqueous layer was extracted with DCM (3×). The combined organic layers were dried over MgSO$_4$, filtered, and concentrated in vacuo to provide the title compound (0.15 g, 88%). MS (ESI): mass calculated for C$_{15}$H$_{10}$FN$_3$O$_4$S, 347.04; m/z found, 346/347/348 [M–H]$^-$. HPLC (reverse phase): R$_T$=8.23 min. $^1$H NMR (400 MHz, CD$_3$OD): 8.95 (dd, J=4.9, 1.8 Hz, 2H), 8.61 (dd, J=7.4, 1.3 Hz, 1H), 8.33 (dd, J=8.5, 1.4 Hz, 1H), 7.96 (dd, J=8.5, 7.4 Hz, 1H), 7.89 (dd, J=8.9, 6.5 Hz, 1H), 7.45 (dd, J=11.4, 2.5 Hz), 6.70-6.64 (m, 1H).

D. (R)-N-[1-(2,4-Dichlorophenyl)ethyl]-4-fluoro-2-(Quinoxaline-5-sulfonylamino)-benzamide. To a solution of 4-fluoro-2-(quinoxaline-5-sulfonylamino)benzoic acid (0.024 g, 0.070 mmol) in DMF (0.40 mL) at room temperature was added pyridine (0.017 ml, 0.21 mmol) followed by HATU (0.053 g, 0.14 mmol). The reaction mixture was agitated for 1 h on a shaker. (R)-1-(2,4-Dichlorophenyl)ethylamine hydrochoride (EXAMPLE 1, Step J; 0.032 g, 0.14 mmol) was added followed by Hünig's base (0.024 mL,
0.14 mmol). The reaction mixture was agitated for 2 h. TFA (0.10 mL) was added to quench the reaction. The mixture was diluted with DMF (1 mL) and the product amide was obtained by purification of the resulting mixture by preparative reverse-phase chromatography. The title amide was obtained as a solid (26 mg, 72%). MS (ESI): mass calculated for C$_{23}$H$_{17}$Cl$_2$FN$_4$O$_3$S, 518.0; m/z found, 519/521 [M+H]$^+$; 541/543 [M+Na]$^+$. HPLC (reverse phase): R$_T$=9.95 min. $^1$H NMR (400 MHz, CDCl$_3$): 11.58 (s, 1H), 8.84 (d, J=1.8 Hz, 1H), 8.73 (d, J=1.8 Hz, 1H), 8.54 (dd, J=7.4, 1.4 Hz, 1H), 8.30 (dd, J=8.5, 1.4 Hz, 1H), 7.85 (dd, J=8.5, 7.4 Hz, 1H), 7.52 (dd, J=11.2, 2.5 Hz, 1H), 7.44 (t, J=1.2 Hz, 1H), 7.34 (dd, J=22.7, 2.7 Hz, 1H), 7.23 (d, J=1.2 Hz, 2H), 6.64 (dd, J=2.6, 1.2 Hz, 1H), 6.47-6.44 (m, 1H), 5.44-5.39 (m, 1H), 1.53 (d, J=7.0 Hz, 3H).

Example 38

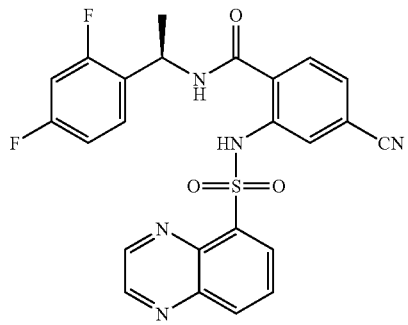

(R)-4-Cyano-N-[1-(2,4-difluoro-phenyl)ethyl]-2-(quinoxaline-5-sulfonylamino)-benzamide.

A. 4-Methyl-3-nitrobenzonitrile. Nitric acid (20 mL) was added dropwise to a 0° C. mixture of 4-tolunitrile (11 g, 0.098 mol) in H$_2$SO$_4$ (20 mL) over 1 h. The reaction mixture was stirred at 0° C. for a further hour, then was poured onto crushed ice. The resulting precipitate was collected by filtration, providing the title compound as a white solid (15.2 g, 95%). $^1$H NMR (500 MHz, CDCl$_3$): 8.27 (d, J=1.6 Hz, 1H), 7.78 (dd, J=8.0, 1.7 Hz, 1H), 7.51 (d, J=8.0 Hz, 1H), 2.69 (s, 3H).

B. 4-Cyano-2-nitrobenzoic acid. To a 0° C. solution of 4-methyl-3-nitrobenzonitrile (5.0 g, 0.031 mol) in H$_2$SO$_4$ (83 mL) was added dropwise over 2 h a mixture of Na$_2$Cr$_2$O$_7$ (14 g, 0.047 mol) and H$_2$SO$_4$ (15 mL). The reaction mixture was allowed to warm to room temperature with stirring over 48 h. The resulting green mixture was poured onto crushed ice, and the precipitate was collected by filtration. The filtered solids were dissolved in 5% aq. Na$_2$CO$_3$ (60 mL) and the residual solids were removed by filtration. The filtrate was treated with dilute HCl and the resulting precipitate was collected by filtration and dried in air to provide the title compound as a white solid (2.7 g, 46%). $^1$H NMR (500 MHz, CD$_3$OD): 8.39 (d, J=1.3 Hz, 1H), 8.12 (dd, J=8.0, 1.3 Hz, 1H), 8.00 (d, J=8.0, 1H).

C. 4-Cyano-2-nitro-benzoic acid methyl ester. To a stirred solution of 4-cyano-2-nitrobenzoic acid (2.7 g, 0.014 mol) in DMF (10 mL) was added DBU (3.9 mL, 0.028 mol). The reaction mixture was stirred for 15 min after which iodomethane (1.8 mL, 0.028 mol) was added at 0° C. The mixture was warmed to room temperature and stirred overnight. The mixture was diluted with EtOAc and washed with H$_2$O (3×). The organic layer was dried over MgSO$_4$, filtered, concentrated, and purified by flash chromatography (hexanes/EtOAc) to provide the title compound (2.63 g, 91%). HPLC (reverse phase): R$_T$=8.26 min. $^1$H NMR (400 MHz, CDCl$_3$): 8.24 (d, J=1.4 Hz, 1H), 7.97 (dd, J=8.0, 1.5 Hz, 1H), 7.87 (d, J=7.8 Hz, 1H), 3.97 (s, 3H).

D. 2-Amino-4-cyano-benzoic acid methyl ester. A solution of 4-cyano-2-nitro-benzoic acid methyl ester (2.41 g, 0.012 mol) was dissolved in a mixture of DCM (15 mL) and EtOAc (15 mL) followed by the addition of SnCl$_2$.2H$_2$O (11 g, 0.047 mol). The mixture was stirred overnight at room temperature, then was neutralized by shaking with an aq. NaHCO$_3$ solution. The resulting salts were removed by filtration through a pad of diatomaceous earth. The filtrate was extracted with DCM (3×). The combined organic layers were dried over MgSO$_4$, filtered, and concentrated in vacuo to provide the title compound (1.95 g, 95%). TLC (silica, 50% EtOAc/hexanes): R$_f$=0.55. MS (ESI): mass calculated for C$_9$H$_8$N$_2$O$_2$, 176.06; m/z found, 175.1 [M–H]$^-$. HPLC (reverse phase): R$_T$=8.19 min. $^1$H NMR (400 MHz, CDCl$_3$): 7.93 (d, J=8.2 Hz, 1H), 6.94 (d, J=1.4 Hz, 1H), 6.87 (dd, J=8.2, 1.6 Hz, 1H), 5.93 (s, 2H), 3.90 (s, 3H).

E. 2-(Benzo[1,2,5]thiadiazole-4-sulfonylamino)-4-cyanobenzoic acid methyl ester. 4-Chlorosulfonyl-2,1,3-benzothiadiazole (1.99 g, 8.51 mmol) was added to a solution of 2-amino-4-cyanobenzoic acid methyl ester (1.00 g, 5.68 mmol) and pyridine (0.92 mL, 11 mmol) in DCM (10 mL). After standing overnight at room temperature the reaction mixture was acidified with 1 N HCl and diluted with H$_2$O. The aqueous layer was extracted with DCM (3×). The combined organic layers were dried over MgSO$_4$, filtered, concentrated, and purified by flash chromatography (hexanes/EtOAc) to provide the title compound (1.25 g, 59%). TLC (silica, 50% EtOAc/hexanes): R$_f$=0.40. MS (ESI): mass calculated for C$_{15}$H$_{10}$N$_4$O$_4$S$_2$, 374.0; m/z found, 373 [M–H]$^-$. HPLC (reverse phase): R$_T$=9.11 min. $^1$H NMR (500 MHz, CDCl$_3$): 11.35 (s, 1H), 8.43 (dd, J=7.1, 1.0 Hz, 1H), 8.26 (dd, J=8.8, 1.0 Hz, 1H), 8.06 (d, J=1.5 Hz, 1H), 7.98 (d, J=8.2 Hz, 1H), 7.76 (dd, J=8.8, 7.1 Hz, 1H), 7.23 (dd, J=8.2, 1.5 Hz, 1H), 3.97 (s, 3H).

F. 4-Cyano-2-(quinoxaline-5-sulfonylamino)benzoic acid methyl ester. Zinc powder (2.18 g, 33.4 mmol) was added to a mixture of 2-(benzo[1,2,5]thiadiazole-4-sulfonylamino)-4-cyano-benzoic acid methyl ester (1.25 g, 3.34 mmol) and ACOH (20 mL), and the resulting mixture was heated at 50° C. for 2 h with vigorous stirring. The mixture was filtered through a pad of diatomaceous earth, rinsed with methanol, and concentrated to a yellow solid. This material was dissolved in methanol (15 mL) and added to a mixture of glyoxal sodium bisulfite adduct (2.70 g, 10.0 mmol), AcOH (0.9 mL), NaOAc (0.27 g, 3.3 mmol), and H$_2$O (4.5 mL). The reaction was allowed to proceed at reflux for 3 h. The resulting mixture was diluted with DCM and filtered through a pad of diatomaceous earth, rinsing with DCM. The filtrate was washed with H$_2$O, dried over MgSO$_4$, concentrated, and purified by flash chromatography (hexanes/EtOAc) to provide the title compound (0.28 g, 23%). TLC (silica, 50% EtOAc/hexanes): R$_f$=0.13. MS (ESI): mass calculated for C$_{17}$H$_{12}$N$_4$O$_4$S, 368.1; m/z found, 367 [M–H]$^-$. HPLC (reverse phase): R$_T$=8.72 min. $^1$H NMR (400 MHz, CDCl$_3$): 11.42 (s, 1H), 8.96 (dd, J=4.4, 1.8 Hz, 2H), 8.63 (dd, J=7.4, 1.4 Hz, 1H), 8.36 (dd, J=8.5, 1.4 Hz, 1H), 8.16 (d, J=1.4 Hz, 1H), 7.97-7.90 (m, 2H), 7.20 (dd, J=8.2, 1.5 Hz, 1H), 3.94 (s, 3H).

G. 4-Cyano-2-(quinoxaline-5-sulfonylamino)benzoic acid. To a stirred solution of 4-cyano-2-(quinoxaline-5-sulfonylamino)benzoic acid methyl ester (0.28 g, 0.76 mmol) in THF (5 mL) and H$_2$O (2.5 mL) was added LiOH.H$_2$O (0.16 g, 3.8 mmol). The reaction mixture was stirred at room temperature overnight. The solution was acidified to pH ~2 with concentrated HCl and diluted with H$_2$O. The aqueous layer was extracted with DCM (3×). The combined organic layers were dried over MgSO$_4$, filtered, and concentrated in vacuo to provide the title compound (0.21 g, 81%). MS (ESI): mass calculated for C$_{16}$H$_{10}$N$_4$O$_4$S, 354.0; m/z found, 353 [M–H]$^-$. HPLC (reverse phase): R$_T$=7.91 min. $^1$H NMR (400 MHz, CD$_3$OD): 8.94 (dd, J=10.7, 1.8 Hz, 2H), 8.64 (dd, J=7.4, 1.3 Hz, 1H), 8.34 (dd, J=8.5, 1.3 Hz, 1H), 8.03 (d, J=1.4 Hz, 1H), 7.97 (t, J=7.3 Hz, 2H), 7.28 (dd, J=8.2, 1.5 Hz, 1H).

H. (R)-4-Cyano-N-[1-(2,4-difluorophenyl)ethyl]-2-(Quinoxaline-5-sulfonylamino)-benzamide. To a solution of 4-cyano-2-(quinoxaline-5-sulfonylamino)-benzoic acid (0.025 g, 0.071 mmol) in DMF (0.40 mL) at room temperature was added pyridine (0.017 ml, 0.21 mmol) and HATU (0.053 g, 0.14 mmol). The reaction mixture was agitated for 1 h on a shaker. (R)-1-(2,4-Difluorophenyl)-ethylamine hydrochloride (EXAMPLE 2, Method 1, Step C; 0.027 g, 0.14 mmol) was added followed by Hünig's base (0.024 mL, 0.14 mmol). The reaction mixture was agitated for 2 h. TFA (0.10 mL) was added to quench the reaction. The mixture was diluted with DMF (1 mL) and the product was obtained by purification of the entire reaction mixture by preparative reverse-phase chromatography. The title amide was obtained as a solid (10 mg, 29%). MS (ESI): mass calculated for C$_{24}$H$_{17}$F$_2$N$_5$O$_3$S, 493.10; m/z found, 494/495/496 [M+H]$^+$; 516/517 [M+Na]$^+$. HPLC (reverse phase): R$_T$=9.19 min. $^1$H NMR (400 MHz, CDCl$_3$): 11.18 (s, 1H), 8.87 (d, J=1.8 Hz, 1H), 8.83 (d, J=1.8 Hz, 1H), 8.58 (dd, J=7.4, 1.3 Hz, 1H), 8.33 (dd, J=8.5, 1.4 Hz, 1H), 8.04 (d, J=1.4 Hz, 1H), 7.90 (dd, J=8.4, 7.4 Hz, 1H), 7.41 (d, J=8.1 Hz, 1H), 7.35-7.30 (m, 1H), 7.25-7.22 (m, 1H), 6.90-6.83 (m, 2H), 6.46 (d, J=7.8 Hz, 1H), 5.35-5.29 (m, 1H), 1.56 (d, J=7.0 Hz, 3H).

Example 39

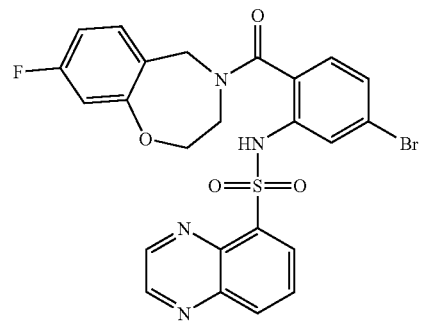

Quinoxaline-5-sulfonic acid [5-bromo-2-(8-fluoro-2,3-dihydro-5H-benzo[f][1,4]oxazepine-4-carbonyl)phenyl]-amide.

A. 3-(3-Fluorophenoxy)propionitrile. A solution of 3-fluorophenol (12.1 mL, 0.13 mol), Triton B (2.1 mL) and acrylonitrile (44 mL, 0.67 mol) was heated at reflux for 20 h. The mixture was cooled to room temperature, diluted with diethyl ether, and washed successively with 1 N NaOH, 1 N HCl, and H$_2$O. The organic extract was dried over MgSO$_4$, and concentrated to provide title compound (13.0 g, 59%). TLC (silica, 40% EtOAc/hexanes): R$_f$=0.54. HPLC (reverse phase): R$_T$=8.18 min. $^1$H NMR (400 MHz, CDCl$_3$): 7.28-7.23 (m, 1H), 6.74-6.69 (m, 2H), 6.64-6.61 (m, 1H), 4.17 (t, J=6.3 Hz, 2H), 2.84 (t, J=6.3 Hz, 2H).

B. 3-(3-Fluorophenoxy)propionic acid. A mixture of 3-(3-fluorophenoxy)-propionitrile (13 g, 0.079 mol) and concentrated HCl (60 mL) was heated at reflux for 16 h. The reaction mixture was cooled to room temperature and the resulting solid was collected, washed with H$_2$O, then diluted with 1 N NaOH (300 mL). The insolubles were removed by filtration. The filtrate was acidified with concentrated HCl. The solid was collected, washed with H$_2$O, and dried to afford title compound (12.3 g, 85%). TLC (silica, 50% EtOAc/hexanes): R$_f$=0.24. HPLC (reverse phase): R$_T$=7.82 min. $^1$H NMR (500 MHz, CDCl$_3$): 7.23-7.20 (m, 1H), 6.70-6.61 (m, 3H), 4.24 (t, J=6.2 Hz, 2H), 2.86 (t, J=6.2 Hz, 2H).

C. 7-Fluorochroman-4-one. To a solution of 3-(3-fluorophenoxy)propionic acid (2.2 g, 0.011 mol) in toluene (25 mL) was added thionyl chloride (4.0 mL, 0.054 mol). The solution was heated at reflux for 1.5 h and concentrated in vacuo. The residue was dissolved in CHCl$_3$ (25 mL), cooled to −65° C. and treated dropwise with trifluoromethanesulfonic acid (1.5 mL, 0.017 mol). The mixture was allowed to warm to room temperature with stirring for 2 h. After the addition of H$_2$O, the layers were separated, and the organic layers were washed with 1 N NaOH. The combined organic extracts were dried over MgSO$_4$, filtered, concentrated, and purified by flash chromatography (hexanes/EtOAc) to provide the title compound (0.96 g, 53%). HPLC (reverse phase): R$_T$=8.22 min. $^1$H NMR (500 MHz, CDCl$_3$): 7.92 (dd, J=8.8, 6.7 Hz, 1H), 6.75-6.72 (m, 1H), 6.66 (dd, J=9.9, 2.4 Hz, 1H), 4.55 (t, J=6.4 Hz, 2H), 2.80 (t, J=6.5 Hz, 2H).

D. 8-Fluoro-3,4-dihydro-2H-benzo[f][1,4]oxazepin-5-one. To an ice cold solution of 7-fluoro-chroman-4-one (0.94 g, 5.7 mmol) in H$_2$SO$_4$ (8 mL) was added NaN$_3$ (0.55 g, 8.5 mmol) in portions. The resulting mixture was stirred at 0° C. for 30 min, then was allowed to warm to room temperature and was stirred overnight. The reaction mixture was poured onto ice, basified to pH ~10 with 1 M NaOH, and extracted with DCM (3×). The combined organic layers were dried over MgSO$_4$, filtered, concentrated, and purified by flash chromatography (hexanes/EtOAc) to provide the title compound (0.33 g, 33%). HPLC (reverse phase): R$_T$=6.96 min. $^1$H NMR (500 MHz, CDCl$_3$): 8.07 (dd, J=9.0, 6.8 Hz, 1H), 6.85-6.81 (m, 1H), 6.71 (dd, J=9.9, 2.5 Hz, 1H), 6.39 (s, 1H), 4.41 (t, J=4.5 Hz, 2H), 3.55-3.52 (m, 2H).

E. 8-Fluoro-2,3,4,5-tetrahydro-benzo[f][1,4]oxazepine. To a 0° C. solution of 8-fluoro-3,4-dihydro-2H-benzo[f][1,4]oxazepin-5-one (0.33 g, 1.8 mmol) in THF (10 mL) was added lithium aluminum hydride (0.21 g, 5.5 mmol) in small portions. The resulting mixture was heated at reflux for 24 h, and then was cooled to room temperature. The reaction was quenched by the successive dropwise addition of H$_2$O (0.21 mL), 15% aq. NaOH solution (0.21 mL), and H$_2$O (0.63 mL). The salts were removed by filtration. The filtrate was dried over MgSO$_4$ and concentrated to yield the title compound (0.24 g, 80%). HPLC (reverse phase): R$_T$=5.81 min. $^1$H NMR (500 MHz, CDCl$_3$): 7.07 (dd, J=8.2, 6.7 Hz, 1H), 6.75 (dd, J=9.8, 2.6 Hz, 1H), 6.73-6.67 (m, 1H), 4.05 (t, J=4.4 Hz, 2H), 3.92 (s, 2H), 3.21 (t, J=4.5 Hz, 2H), 1.58 (br s, 1H).

F. Quinoxaline-5-sulfonic acid [5-bromo-2-(8-fluoro-2,3-dihydro-5H-benzo[f][1,4]oxazepine-4-carbonyl)-phenyl]-amide. The title compound was prepared from the HATU-mediated coupling of 4-bromo-2-(quinoxaline-5-sulfonylamino)benzoic acid (EXAMPLE 1, Step G) and 8-fluoro-2,3,4,5-tetrahydro-benzo[f][1,4]oxazepine and purified as described in Example 1, Step K. MS (ESI): mass calculated for C$_{24}$H$_{18}$BrFN$_4$O$_4$S, 556.0; m/z found, 557/559 [M+H]$^+$, 579/581 [M+Na]$^+$. HPLC (reverse phase): R$_T$=9.41 min. $^1$H NMR (500 MHz, CDCl$_3$, mixture of amide rotamers): 9.06-8.94 (m, 3H), 8.50 (br d, J=7.2 Hz, 1H), 8.36 (d, J=8.3 Hz, 1H), 7.89 (t, J=7.9, 1H), 7.85 (d, J=1.7 Hz, 1H), 7.36-7.30 (m, 0.3H), 7.14 (dd, J=8.2, 1.8 Hz, 1H), 6.86-6.80 (m, 0.7H), 6.76-6.71 (m, 2H), 6.69-6.63 (m, 0.7H), 6.59-6.53 (m, 0.3H), 4.51-4.45 (m, 0.6H), 4.12-4.06 (m, 1.4H), 3.91-3.60 (m, 3H), 3.44-3.37 (m, 1H).

Example 40

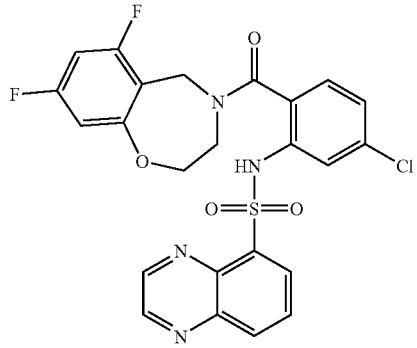

Quinoxaline-5-sulfonic acid [5-chloro-2-(6,8-difluoro-2,3-dihydro-5H-benzo[f][1,4]oxazepine-4-carbonyl)-phenyl]-amide.

A. 3-(3,5-Difluorophenoxy)propionitrile. A solution of 3,5-fluorophenol (2.8 mL, 0.021 mol), Triton B (0.83 mL), and acrylonitrile (7.0 mL, 0.11 mol) was heated at reflux for 20 h. The mixture was cooled to room temperature, diluted with diethyl ether, and washed successively with 1 N NaOH, 1 N HCl, and H$_2$O. The organic extract was dried over MgSO$_4$ and concentrated to provide title compound (1.33 g, 35%). HPLC (reverse phase): R$_T$=8.66 min. $^1$H NMR (400 MHz, CDCl$_3$): 6.84-6.43 (m, 3H), 4.16 (t, J=6.3 Hz, 2H), 2.85 (t, J=6.3 Hz, 2H).

B. 3-(3,5-Difluorophenoxy)propionic acid. A mixture of 3-(3,5-difluoro-phenoxy)propionitrile (1.33 g, 7.26 mmol) and concentrated HCl (10 mL) was heated at reflux for 16 h. After the reaction mixture was cooled to room temperature, the resulting solid was collected by filtration, washed with H$_2$O, and diluted with 1 N NaOH (30 mL). The remaining solids were removed by filtration. The filtrate was acidified with concentrated HCl. The resulting precipitate was collected, washed with H$_2$O, and dried to afford the title compound (1.11 g, 76%). TLC (silica, 50% EtOAc/hexanes): R$_f$=0.15. MS (ESI): mass calculated for C$_9$H$_8$F$_2$O$_3$, 202.04; m/z found, 201 [M–H]⁻. HPLC (reverse phase): $R_T$=8.02 min. ¹H NMR (400 MHz, CDCl₃): 6.45-6.41 (m, 3H), 4.21 (t, J=6.2 Hz, 2H), 2.86 (t, J=6.2 Hz, 2H).

C. 5,7-Difluorochroman-4-one. To a solution of 3-(3,5-difluorophenoxy)-propionic acid (1.11 g, 5.49 mol) in toluene (10 mL) was added thionyl chloride (2.0 mL, 27 mmol). The solution was heated at reflux for 1.5 h, then was concentrated in vacuo. The residue was dissolved in CHCl₃ (10 mL), cooled to −65° C., and treated dropwise with trifluoromethanesulfonic acid (0.73 mL, 8.2 mmol). The mixture was allowed to warm to room temperature with stirring over 2 h. After the addition of H₂O, the layers were separated. The organic layer was washed with 1 N NaOH, then dried over MgSO₄, filtered, concentrated, and purified by flash chromatography (hexanes/EtOAc) to provide the title compound (0.73 g, 73%). TLC (silica, 50% EtOAc/hexanes): $R_f$=0.43. ¹H NMR (400 MHz, CDCl₃): 6.52-6.47 (m, 2H), 4.54 (t, J=6.4 Hz, 2H), 2.80 (t, J=6.4 Hz, 2H).

D. 6,8-Difluoro-3,4-dihydro-2H-benzo[f][1,4]oxazepin-5-one. To an ice cold solution of 5,7-difluorochroman-4-one (0.73 g, 4.0 mmol) in H₂SO₄ (10 mL) was added NaN₃ (0.39 g, 5.9 mmol) in portions. The resulting mixture was allowed to stir at 0° C. for 30 min, then was warmed to room temperature and stirred overnight. The reaction mixture was poured onto ice, basified to pH ~10 with 1 M NaOH, and extracted with DCM (3×). The combined organic layers were dried over MgSO₄, filtered, concentrated, and purified by flash chromatography (hexanes/EtOAc) to provide the title compound (0.44 g, 56%). HPLC (reverse phase): $R_T$=6.64 min. ¹H NMR (500 MHz, CDCl₃): 6.98 (br s, 1H), 6.73-6.70 (m, 1H), 6.64-6.62 (m, 1H), 4.34 (t, J=5.5 Hz, 2H), 3.47-3.44 (m, 2H).

E. 6,8-Difluoro-2,3,4,5-tetrahydro-benzo[f][1,4]oxazepine. To a 0° C. solution of 6,8-fluoro-3,4-dihydro-2H-benzo[f][1,4]oxazepin-5-one (0.56 g, 2.8 mmol) in THF (15 mL) was added BH₃.THF (1 M in THF, 5.62 mL, 5.62 mmol). The resulting mixture was heated at reflux for 24 h, then cooled to room temperature. Excess borane was destroyed by careful addition of methanol (8 mL). The solvent was removed in vacuo, and the resulting oil was treated with HCl (4.0 M in 1,4-dioxane) and heated at reflux for 3 h. The mixture was concentrated, and the residue was suspended in H₂O, basified with 1 M NaOH, and extracted with DCM (3×). The combined organic extracts were dried over MgSO₄, filtered, and concentrated to yield title compound (0.45 g, 87%). ¹H NMR (400 MHz, CDCl₃): 6.59-6.50 (m, 2H), 4.11-4.08 (m, 2H), 4.00 (s, 2H), 3.23 (t, J=4.6 Hz, 2H), (NH hot observed).

F. Quinoxaline-5-sulfonic acid [5-chloro-2-(6,8-difluoro-2,3-dihydro-5H-benzo[f][1,4]oxazepine-4-carbonyl)-phenyl]-amide. The title compound was prepared from the HATU-mediated coupling of 4-chloro-2-(quinoxaline-5-sulfonylamino)benzoic acid (Example 3, Step B) and 8-fluoro-2,3,4,5-tetrahydro-benzo[f][1,4]oxazepine and purified as described in EXAMPLE 1, Step K. MS (ESI): mass calculated for $C_{24}H_{17}ClF_2N_4O_4S$, 530.1; m/z found, 531 [M+H]⁺, 553 [M+Na]⁺. HPLC (reverse phase): $R_T$=9.38 min. ¹H NMR (500 MHz, CDCl₃, mixture of amide rotamers): 9.0-8.9 (m, 3H), 8.51 (br d, J=6.7 Hz, 1H), 8.34 (dd, J=8.4, 1.3 Hz, 1H), 7.91-7.88 (m, 1H), 7.65 (d, J=1.6 Hz, 1H), 6.99-6.94 (m, 1H), 6.82-6.72 (m, 1H), 6.6-6.5 (m, 2H), 4.8-4.6 (m, 1H), 4.3-3.9 (m, 3H), 3.85-3.72 (m, 3H), 3.6-3.4 (m, 1H).

Examples 41 through 96 were prepared using the methods described above.

Assay Methods

Binding Assay

Assay Development

Zinc Finger Proteins (ZFP) specific for the CCK2R gene were identified by Sangamo Biosciences. The ZFP domain was fused with the herpes simplex virus VP16 activation domain, and the fusion protein was subsequently cloned into the pcDNA3 mammalian expression vector (Invitrogen, San Diego, Calif.). Tet-inducible cell lines expressing the coding region from the ZFP vector were created using the T-REx-293™ cell line (Invitrogen). After 2 weeks of selection in culture medium containing 400 mg/mL Zeocin (Invitrogen), sixty drug-resistant stable clones were isolated and analyzed for ZFP expression as well as CCK2R induction upon addition of doxycycline to the culture medium. The cell line with the most appropriate CCK2R ZFP construct was used in all further assays and was termed the HEKZFP cell line.

Cell Culture

HEKZFP cells were grown in DMEM supplemented with L-glutamine (2 mM), penicillin (50 units/mL) and streptomycin (50 μg/mL) and 10% FBS (v/v). HEKZFP cells were treated with 2 mM doxycycline (Sigma-Aldrich, MO; USA) for 2 days to de-repress the tet-regulated expression of the CCK2 receptor selective zinc finger proteins and were harvested using a rubber cell scraper.

Membrane Preparation

Membranes were prepared from the HEKZFP cells after induction. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from E. A. Harper et al. (Br. J. Pharmacol. (1996) 118(7):1717-1726). The thawed pellets were homogenized using a Polytron PT-10 (7×1 s). The homogenates were centrifuged for 5 min at 1500 rpm (600×g), and the resulting pellets were discarded. The supernatants were re-centrifuged in order to collect the receptor-membrane pellets (25 min 15,000 rpm; 39,800×g), which were re-suspended in buffer A.

Incubation Conditions

All assays were conducted in 96-well plates (GF/B millipore filter plates) using buffer A. For the optimal cell number determination experiments, cells in concentrations ranging from 2.5×10⁵ to 12.5×10⁵ cells/well were incubated with 20 pM [¹²⁵I]-BH-CCK-8S (50 μL 60 pM solution) in a total volume of 150 μL. Total binding of [¹²⁵I]-BH-CCK-8S was determined in the presence of 15 μL of buffer A. Non-specific binding of [¹²⁵I]-BH-CCK-8S was determined in the presence of 15 μL of 10 μM YF476, a CCK-2 receptor selective antagonist that is structurally unrelated to the radioligand [¹²⁵I]-BH-CCK-8S. The assay preparation was incubated for 1 h at 21±3° C., and then the assay was terminated by rapid filtration of the preparation under reduced pressure. The loaded filters were washed three times using undiluted PBS (100 μL), and then 100 μL of scintillation fluid was added to the filter plate. Bound radioactivity was determined using a Topcount (Packard BioScience, Meriden, Conn.) with a count time of 1 min. From these experiments a cell concentration of 1 pellet in 15 mL of buffer was chosen for use in other assays. To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

Data Analysis

The pKi values were determined using the equation of Y.-C. Cheng and W. H. Prusoff (Biochem. Pharmacol., 1973, 22(23):3099-3108):

$$K_i = \frac{IC_{50}}{1 + \frac{[L]}{K_D}}$$

To circumvent problems associated with computer-assisted data analysis of compounds with low affinity, the data obtained in the current study were weighted according to a method described by Morton. In brief, 100% and 0% specific binding were defined independently using total binding and binding obtained in the presence of a high concentration of the reference antagonist, 2-NAP.

TABLE 1

| EX | pK$_i$ |
|---|---|
| 1 | 8.1 |
| 2 | 7.7 |
| 3 | 7.9 |
| 4 | 7.6 |
| 5 | 7.8 |
| 6 | 7.5 |
| 7 | 7.5 |
| 8 | 7.4 |
| 9 | 7.4 |
| 10 | 7.3 |
| 11 | 7.2 |
| 12 | 7.1 |
| 13 | 6.8 |
| 14 | 6.5 |
| 15 | 7.9 |
| 16 | 7.4 |
| 17 | 7.2 |
| 18 | 7.2 |
| 19 | 7.1 |
| 20 | 7.1 |
| 21 | 6.9 |
| 22 | 6.8 |
| 23 | 6.6 |
| 24 | 6.5 |
| 25 | 6.5 |
| 26 | 6.5 |
| 27 | 6.5 |
| 28 | 6.4 |
| 29 | 6.3 |
| 30 | 6.2 |
| 32 | 7.2 |
| 33 | 7.9 |
| 34 | 8.1 |
| 35 | 7.8 |
| 36 | 7.6 |
| 37 | 6.7 |
| 38 | 6.5 |
| 39 | 7.1 |
| 40 | 6.6 |
| 42 | 7.6 |
| 43 | 8.0 |
| 45 | 7.5 |
| 48 | 7.7 |
| 50 | 7.2 |
| 53 | 7.6 |

TABLE 1-continued

| EX | pK$_i$ |
|---|---|
| 54 | 7.4 |
| 56 | 7.4 |
| 57 | 7.4 |
| 58 | 7.2 |
| 61 | 7.4 |
| 62 | 7.8 |
| 63 | 7.5 |
| 64 | 7.6 |
| 66 | 7.3 |
| 67 | 6.2 |
| 71 | 7.1 |
| 72 | 7.0 |
| 73 | 7.1 |
| 74 | 7.5 |
| 75 | 7.2 |
| 76 | 7.6 |
| 77 | 7.3 |
| 78 | 7.4 |
| 79 | 6.6 |
| 92 | 7.1 |
| 94 | 6.4 |
| 96 | 6.2 |

Guinea-Pig Gastric Corpeal Muscle Assay

CCK2 receptor-mediated muscle contraction was measured in an isolated muscle-strip assay of guinea-pig gastric corpeal muscle according to the methods described by Roberts et al. (S. P. Roberts, E. A. Harper, G. F. Watt, V. P. Gerskowitch, R. A. Hull, N. P. Shankley, and J. W. Black, Br. J. Pharmacol., 1996, 118(7):1779-1789). In brief, strips of muscle were dissected and suspended in isolated tissue organ baths for isotonic muscle contraction recording. The baths, containing Krebs-Henseleit solution, were maintained at 24° C. and gassed continuously with 95% $O_2$ and 5% $CO_2$. CCK1 receptors known to be present in this assay were blocked using a selective concentration of a suitable CCK1 receptor antagonist (e.g. 2-NAP). The effectiveness of the test compounds was assessed by measuring their effect on contractile concentration-response curves obtained using a well-characterized surrogate for the hormone gastrin (pentagastrin). The title compound of Example 2 behaved as a competitive antagonist in this assay with a pK$_B$ value of 8.8.

What is claimed is:

1. A compound having CCK2 antagonist activity of formula (I):

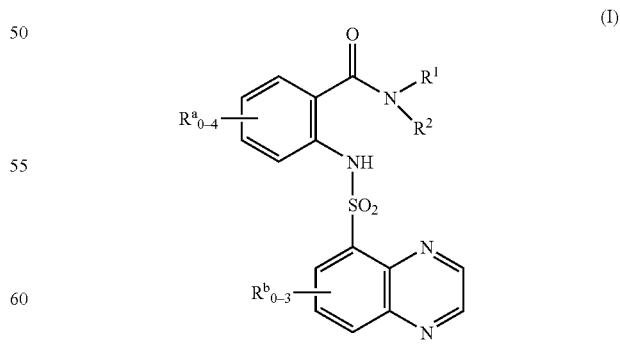

wherein

R$^1$ and R$^2$ are each independently selected from the group consisting of a) H, $C_{1-7}$alkyl, $C_{2-7}$alkenyl, $C_{2-7}$alkynyl, $C_{3-7}$cycloalkyl, $C_{3-7}$cycloalkenyl, benzo-fused$C_{4-7}$cycloalkyl where the point of attachment is a carbon atom adjacent to the ring junction, $C_{3-7}$cycloalkyl$C_{1-7}$alkyl,
b) naphthyl-$(CR^s_2)$—, benzoyl$C_{0-3}$alkyl-$(CR^s_2)$—, phenyl, said phenyl optionally fused at two adjacent carbon atoms to $R^f$, phenyl-$(CR^s_2)$—, said phenyl optionally fused at two adjacent carbon atoms to $R^f$,
$R^f$ is a linear 3- to 5-membered hydrocarbon moiety optionally mono or di-oxo substituted having 0 or 1 unsaturated bonds,
c) $Ar^6$—$(CR^s_2)$—, where $Ar^6$ is a 6-membered heteroaryl having carbon as a point of attachment, having 1 or 2 heteroatom members which are —N= and optionally benzo fused,
d) $Ar^5$—$(CR^s_2)$—, where $Ar^5$ is a 5-membered heteroaryl having carbon as a point of attachment, having 1 heteroatom member selected from the group consisting of O, S, >NH or >N$C_{1-4}$alkyl, having 0 or 1 additional heteroatom member which is —N= and optionally benzofused,
e) $Ar^{6-6}$—$(CR^s_2)$—, where $Ar^{6-6}$ is phenyl having the point of attachment and fused to a 6-membered heteroaryl having 1 or 2 heteroatom members which are —N=,
f) $Ar^{6-5}$—$(CR^s_2)$—, where $Ar^{6-5}$ is phenyl having the point of attachment and fused to a 5-membered heteroaryl having 1 heteroatom member selected from the group consisting of O, S, >NH or >N$C_{1-4}$alkyl and having 0 or 1 additional heteroatom member which is —N=,
g) $C_{1-4}$alkylO— and HS$C_{1-4}$alkyl,
where $R^1$ and $R^2$ are not simultaneously H and, except in positions where $R^s$ is indicated, each of a) to g) is substituted with 0, 1, 2, or 3 of $R^q$,
$R^q$ is independently selected from the group consisting of $C_{1-4}$alkyl, hydroxy, fluoro, chloro, bromo, iodo, trifluoromethyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy and $C_{1-4}$alkylS—,
$R^s$ is independently selected from the group consisting of H, $C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, HS—$C_{1-4}$alkyl, $C_{1-4}$alkylO-$C_{1-4}$alkyl, $C_{1-4}$alkylS—$C_{1-4}$alkyl and phenyl;
or, alternatively,
$R^1$ and $R^2$ may be taken together with the nitrogen to which they are attached and are selected from the group consisting of
i) 10-oxa-4-aza-tricyclo[5.2.1.0$^{2,6}$]dec-4-yl, optionally mono- or di-substituted with $R^p$,
$R^p$ is independently selected from the group consisting of hydroxy, $C_{1-4}$alkyl, hydroxy$C_{1-4}$alkyl, phenyl, mono-, di- or tri-halo substituted phenyl and hydroxyphenyl,
ii) a 4-7 membered heterocyclic ring said heterocyclic ring having 0 or 1 additional heteroatom members separated from the nitrogen of attachment by at least one carbon member and selected from O, S, —N=, >NH or >N$R^p$, having 0, 1 or 2 unsaturated bonds, having 0, 1 or 2 carbon members which is a carbonyl, optionally having one carbon member which forms a bridge and having 0, 1 or 2 substituents $R^p$,
iii) a benzo fused 4-7 membered heterocyclic ring said heterocyclic ring having 0 or 1 additional heteroatom members separated from the nitrogen of attachment by at least one carbon member and selected from O, S, —N=, >NH or >N$R^p$, having 0 or 1 additional unsaturated bonds, having 0, 1 or 2 carbon members which is a carbonyl, having 0, 1, 2, or 3 halo substituents on the benzene ring only and having 0 or 1 or 2 substituents $R^p$,
iv) a 4-7 membered heterocyclic ring said heterocyclic ring having 0 or 1 additional heteroatom members separated from the nitrogen of attachment by at least one carbon member and selected from O, S, —N=, >NH or >N$R^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N=, >NH or >N$R^p$, having 0, 1 or 2 unsaturated bonds, having 0, 1 or 2 carbon members which is a carbonyl and having 0, 1 or 2 substituents $R^p$;
v) 8-oxo-1,5,6,8-tetrahydro-2H,4H-1,5-methano-pyrido[1,2-a][1,5]diazocin-3-yl, optionally having 0, 1 or 2 substituents $R^p$;
$R^a$ is independently selected from the group consisting of $C_{1-6}$alkyl, $C_{2-6}$alkenyl, $C_{3-6}$cycloalkyl, phenyl, furanyl, thienyl, benzyl, pyrrol-1-yl, —OH, —O$C_{1-6}$alkyl, —O$C_{3-6}$cycloalkyl, -Ophenyl, -Obenzyl, —SH, —S$C_{1-6}$alkyl, —S$C_{3-6}$cycloalkyl, -Sphenyl, -Sbenzyl, —CN, —NO$_2$, —N($R^y$)$R^z$ (wherein $R^y$ and $R^z$ are independently selected from H, $C_{1-4}$alkyl or $C_{1-6}$cycloalkyl$C_{1-4}$alkyl), —(C=O)$C_{1-4}$alkyl, —SCF$_3$, halo, —CF$_3$, —OCF$_3$, and —COO$C_{1-4}$alkyl, or, alternatively, two adjacent $R^a$, may be taken together with the carbons of attachment to form a fused ring and selected from the group consisting of phenyl, pyridyl and pyrimidinyl;
or alternatively, $R^2$ and one of $R^a$ can be taken together to be —CH$_2$— or >C=O and to form a fused ring to the phenyl;
$R^b$ is, independently, selected from the group consisting of $C_{1-4}$alkyl and halogen;
and enantiomers, diastereomers, hydrates and pharmaceutically acceptable salts, esters and amides thereof.

2. The compound of claim 1 wherein $R^1$ and $R^2$ are independently selected from the group consisting of H,
a) $C_{1-7}$alkyl, ethenyl, propenyl, butenyl, ethynyl, propynyl, cyclobutyl, cyclopentyl, cyclohexyl, cycloheptyl, cyclopentenyl, cyclohexenyl, indan-1-yl, 1,2,3,4-tetrahydro-naphthalen-1-yl, 6,7,8,9-tetrahydro-5H-benzocyclohepten-5-yl, cyclobutyl$C_{1-4}$alkyl, cyclopentyl$C_{1-4}$alkyl, cyclohexyl$C_{1-4}$alkyl, cycloheptyl$C_{1-4}$alkyl,
b) phenyl, 6,7,8,9-tetrahydro-5H-benzocyclohepten-1,2,3 or 4-yl, optionally 5,6,7,8 or 9 oxo substituted, 5,6,7,8-tetrahydro-naphthalen-1,2,3 or 4-yl, optionally 5,6,7 or 8 oxo substituted, benzyl, 6,7,8,9-tetrahydro-5H-benzocyclohepten-1,2,3 or 4-ylmethyl, optionally 5,6,7,8 or 9 oxo substituted, 5,6,7,8-tetrahydro-naphthalen-1,2,3 or 4-ylmethyl, optionally 5,6,7 or 8 oxo substituted, 1-phenyleth-1-yl, benzhydryl, naphthylmethyl, benzoylmethyl, 1-benzoyleth-1-yl,
c) pyridylmethyl, pyrazinylmethyl, pyrimidinylmethyl, pyridazinylmethyl, quinolin-2,3 or 4-ylmethyl, isoquinolin-1,3 or 4-ylmethyl, quinazolin-2 or 4-ylmethyl, quinoxalin-2 or 3-ylmethyl,
d) furanylmethyl, thiophenylmethyl, 1-(H or $C_{1-4}$alkyl) pyrrolylmethyl, oxazolylmethyl, thiazolylmethyl, pyrazolylmethyl, imidazolylmethyl, isoxazolylmethyl, isothiazolylmethyl, benzofuran-2 or 3-ylmethyl, benzothiophen-2 or 3-ylmethyl, 1-(H or $C_{1-4}$alkyl)-1H-indol-2 or 3-ylmethyl, 1-(H or $C_{1-4}$alkyl)-1H-benzimidazol-2-ylmethyl, benzooxazol-2-ylmethyl, benzothiazol-2-ylmethyl, e) quinolin-5,6,7 or 8-ylmethyl, isoquinolin-5,6,7 or 8-ylmethyl, quinazolin-5,6,7 or 8-ylmethyl, quinoxalin-5,6,7 or 8-ylmethyl, f) benzofuran-4,5,6 or 7-ylmethyl, benzothiophen-4,5,6 or 7-ylmethyl, 1-(H or $C_{1-4}$alky)-1H-indol-4,5,6 or 7-ylmethyl, 1-(H or $C_{1-4}$alkyl)-1H-benzimidazol-4,5,6 or 7-ylmethyl, benzooxazol-4,5,6 or 7-ylmethyl, benzothiazol-4,5,6 or 7-ylmethyl, g) $C_{1-4}$alkylO- and $HSC_{1-4}$alkyl, where each of a) to g) is substituted with 0, 1, 2, or 3 of $R^q$ and for those groups in which $R^s$ is hydrogen, up to one $R^s$ may be other than hydrogen.

3. The compound of claim 1 wherein $R^1$ and $R^2$ are independently selected from the group consisting of hydrogen, methyl, ethyl, butyl, hexyl, phenyl, 6,7,8,9-tetrahydro-5H-benzocyclohepten-2-yl, optionally 5,6,7,8 or 9 oxo substituted, benzyl, 1-phenyleth-1-yl, furanylmethyl, benzoylethyl, 1-benzoyleth-1-yl, methylO-, cyclohexyl, cyclohexylmethyl, pyridylethyl, naphthylmethyl, 1,2,3,4-tetrahydro-naphthalen-1-yl, benzhydryl, where each member is substituted with 0, 1, 2, or 3 of $R^q$ and, optionally, for those groups in which $R^s$ is hydrogen, up to one $R^s$ may be other than hydrogen.

4. The compound of claim 1 wherein $R^1$ and $R^2$ are independently selected from the group consisting of hydrogen, methyl, ethyl, butyl, phenyl, benzyl, 2-bromobenzyl, 2-chlorobenzyl, 4-chlorobenzyl, 2,4-dichlorobenzyl, 3,4-dichlorobenzyl, 2,6-dichlorobenzyl, 2,4,6-trichlorobenzyl, 2-fluorobenzyl, 4-fluorobenzyl, 2,4-difluorobenzyl, 2,6-difluorobenzyl, 2,4,6-trifluorobenzyl, 2-chloro-4-fluorobenzyl, 2-fluoro-4-bromobenzyl, 2-fluoro-4-chlorobenzyl, 2-methylbenzyl, 2-methylsulfanylbenzyl, 2-trifluoromethylbenzyl, 1-phenyleth-1-yl, 1-phenylprop-1-yl, 1-(4-bromophenyl)eth-1-yl, 1-(4-fluorophenyl)eth-1-yl, 1-(2,4-dibromophenyl)eth-1-yl 1-(2,4-dichlorophenyl)eth-1-yl, 1-(3,4-dichlorophenyl)eth-1-yl, 1-(2,4-difluorophenyl)eth-1-yl, 2-fluoro-1-(2,4-difluorophenyl)eth-1-yl, 2-fluoro-1-(4-fluorophenyl)eth-1-yl, 1-(4-methylphenyl)eth-1-yl, 1-methyl-1-phenyleth-1-yl, 2,2,2-trifluoro-1-phenyleth-1-yl, 2,2,2-trifluoro-1-(2,4-difluorophenyl)eth-1-yl, 1-phenyl-2-dimethylaminoeth-1-yl, 1-benzoyleth-1-yl, cyclohexyl, 1-cyclohexyleth-1-yl, furan-2-ylmethyl, naphth-1-ylmethyl, methoxy, methylS-ethyl, 6-methyl-6-hydroxyhept-2-yl, pyrid-2-ylethyl, 1,2,3,4-tetrahydro-naphthalen-1-yl, 1-phenyl-2-hydroxyeth-1-yl, benzhydryl, 4-hydroxymethylpiperidin-1-yl, 1-furan-2-yl-2-phenyleth-1-yl and 9-oxo-6,7,8,9-tetrahydro-5H-benzocyclohepten-2-yl.

5. The compound of claim 1 wherein $R^1$ and $R^2$ is H or $C_{1-4}$alkyl where the other is not H or $C_{1-4}$alkyl.

6. The compound of claim 1 wherein one of $R^1$ and $R^2$ is H, methyl or ethyl.

7. The compound of claim 1 wherein at least one of $R^1$ and $R^2$ are selected from the groups consisting of

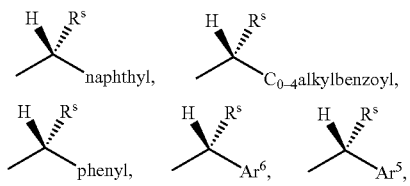

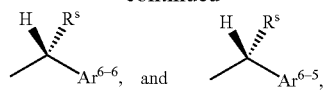

with the proviso that said $R^s$ is not hydrogen, said phenyl is optionally fused at two adjacent carbon atoms to $R^f$ and, except in positions where "$R^s$" or "H" is specifically indicated, each member is substituted with 0, 1, 2, or 3 of $R^q$.

8. The compound of claim 1 wherein $R^f$ is selected from the group consisting of $-CH_2CH_2CH_2-$, $-CH_2CH_2CH_2CH_2-$, $-CH_2CH_2CH_2CH_2CH_2-$ and $-(C=O)CH_2CH_2CH_2-$.

9. The compound of claim 1 wherein $R^s$ is selected from the group consisting of hydrogen, methyl, ethyl, propyl, trifluoromethyl, halomethyl, aminomethyl, methylaminomethyl, dimethylaminomethyl, hydroxymethyl, methoxymethyl, thiomethyl, methylthiomethyl and phenyl.

10. The compound of claim 1 wherein $R^s$ is selected from the group consisting of H, methyl, ethyl, hydroxymethyl, fluoromethyl and dimethylaminomethyl.

11. The compound of claim 1 wherein $R^q$ is selected from the group consisting of methyl, ethyl, propyl, t-butyl, hydroxy, fluoro, chloro, bromo, iodo, trifluoromethyl, aminomethyl, methylaminomethyl, dimethylaminomethyl, hydroxymethyl, methoxymethyl, thiomethyl, methyithiomethyl, methoxy, ethoxy, methylmercapto and ethylmercapto.

12. The compound of claim 1 wherein $R^q$ is selected from the group consisting of methyl, hydroxy, fluoro, chloro, bromo, iodo and trifluoromethyl.

13. The compound of claim 1 wherein $R^1$ and $R^2$ taken together with the nitrogen to which they are attached are selected from the group consisting of i) 10-oxa-4-aza-tricyclo[5.2.1.0$^{2,6}$]dec-4-yl, ii) 2-pyrrolin-1-yl, 3-pyrrolin-1-yl, pyrrolidin-1-yl, 2-imidazolin-1-yl, 3-(H or $R^p$)imidazolidin-1-yl, piperidin-1-yl, morpholin-4-yl, thiomorpholin-4-yl, 3-(H or $R^p$)piperazin-1-yl, azepan-1-yl, thiazolidin-3-yl, oxazolidin-3-yl, 2,5-dihydro-pyrrol-1-yl, azetidin-1-yl, where each member of ii) in each ring has 0 or 1 unsaturated bond and has 0, 1 or 2 carbon members which is a carbonyl, iii) 3,4-dihydro-2H-quinolin-1-yl, 3,4-dihydro-2H-quinolin-2-yl, 2,3-dihydro-indol-1-yl, 1,3-dihydro-isoindol-2-yl, 1-oxo-1,3-dihydro-isoindol-2-yl, tetrahydro-benzo[b, c or d]azepin-1-yl, 2,3-dihydro-benzo[e or f][1,4]oxazepin-4-yl, where each member of iii) in each ring has 0 or 1 unsaturated bond and has 0, 1 or 2 carbon members which are a carbonyl, iv) decahydro-quinolin-1-yl, octahydro-isoquinolin-2-yl, octahydro-[1 or 2]pyrindin-1 or 2-yl, octahydro-indol-1-yl, octahydro-isoindol2-yl, hexahydro-cyclopenta[b]pyrrol-1-yl, hexahydro-cyclopenta[c]pyrrol-2-yl, (5,6,7 or 8-H or $R^p$)-decahydro-[1,5 or 1,6 or 1,7 or 1,8]naphthyridin-1-yl, (5,6,7 or 8-H or $R^p$)-decahydro-[2,5 or 2,6 or 2,7 or 2,8]naphthyridin-2-yl, 1-H or $R^p$-octahydro-pyrollo[2,3-c]pyridin-6-yl, 2-H or $R^p$-octahydro-pyrrolo[3,4-c]pyridin-5-yl, 1-H or $R^p$-octahydro-pyrrolo[3,2-c]pyridin-5-yl, 1-H or $R^p$-octahydro-pyrrolo[2,3-b]pyridin-7-yl, 6-H or $R^p$-octahydro-pyrollo[3,4-b]pyridin-1-yl, 1-H or $R^p$-octahydro-pyrrolo[3,2-b]pyridin-4-yl, 5-H or $R^p$-octahydro-pyrrolo[3,4-c]pyridin-2-yl, 6-H or $R^p$-octahydro-pyrrolo[2,3-c]pyridin-1-yl, 1-H or $R^p$-octahydro-pyrrolo[3,4-b]pyridin-6-yl, 7-H or $R^p$-octahydropyrrolo[2,3-b]pyridin-1-yl, octahydro-1,5-methano-pyrido[1,2-a][1,5]diazocin-3-yl, where each member of iv) in each ring has 0, 1 or 2 carbon members which is a carbonyl, each ring of attachment has 0 or 1 unsaturated bonds and each secondary ring has 0, 1 or 2 unsaturated bonds, v) 8-oxo-1,5,6,8-tetrahydro-2H,4H-1,5-methano-pyrido[1,2-a][1,5]diazocin-3-yl, where each member of i), ii), iii), iv) or v) is further substituted with 0, 1 or 2 of $R^p$.

14. The compound of claim 1 wherein $R^1$ and $R^2$ taken together with the nitrogen to which they are attached are selected from the group consisting of 10-oxa-4-aza-tricyclo[5.2.1.0$^{2,6}$]dec-4-yl, 2-pyrrolin-1-yl, 3-pyrrolin-1-yl, pyrrolidin-1-yl, 2-imidazolin-1-yl, imidazolidin-1-yl, piperidin-1-yl, morpholin-4-yl, thiomorpholin-4-yl, piperazin-1-yl, azepan-1-yl, tetrahydro-benzo[c]azepin-1-yl, tetrahydro-halobenzo[c]azepin-1-yl, 2,3-dihydro-benzo[f][1,4]oxazepin-4-yl, 2,3-dihydro-halobenzo[f][1,4]oxazepin-4-yl, thiazolidin-3-yl, oxazolidin-3-yl, 2,5-dihydro-pyrrol-1-yl, 8-oxo-1,5,6,8-tetrahydro-2H,4H-1,5-methano-pyrido[1,2-a][1,5]diazocin-3-yl, azetidin-1-yl, octahydro-quinolin-1-yl, 3,4-dihydro-2H-quinolin-1-yl, 3,4-dihydro-2H-quinolin-2-yl, where each member is further substituted with 0, 1 or 2 of $R^p$.

15. The compound of claim 1 wherein $R^1$ and $R^2$ taken together with the nitrogen to which they are attached are selected from the group consisting of 1-methyl-10-oxa-4-aza-tricyclo[5.2.1.0$^{2,6}$]dec-4-yl, azetidin-1-yl, pyrrolidin-1-yl, 2-hydroxymethylpyrrolidin-1-yl, 2,4-dimethyl-3-ethylpyrrolidin-1-yl, piperidin-1-yl, 2-methylpiperidin-1-yl, 4-hydroxypiperidin-1-yl, 4-hydroxymethylpiperidin-1-yl, 4-phenylpiperidin-1-yl, azepan-1-yl, tetrahydro-benzo[c]azepin-1-yl, 7-fluoro-tetrahydro-benzo[c]azepin-1-yl, 2,3-dihydro-benzo[f][1,4]oxazepin-4-yl, 8-fluoro-2,3-dihydro-benzo[f][1,4]oxazepin-4-yl, 6,8-difluoro-2,3-dihydro-benzo[f][1,4]oxazepin-4-yl, 4-(2-hydroxyphenyl)piperazin-1-yl, morpholin-4-yl, 2-methylmorpholin-4-yl, 2,6-dimethylmorpholin-4-yl, octahydro-isoquinolin-2-yl, decahydro-quinolin-1-yl, thiazolidin-3-yl, 2,5-dimethyl-2,5-dihydro-pyrrol-1-yl, 8-oxo-1,5,6,8-tetrahydro-2H,4H-1,5-methano-pyrido[1,2-a][1,5]diazocin-3-yl and 3,4-dihydro-2H-quinolin-2-yl.

16. The compound of claim 1 wherein $R^p$ is selected from the group consisting of hydroxy, methyl, ethyl, propyl, hydroxymethyl, hydroxyethyl, phenyl, p-halophenyl, m-halophenyl, o-halophenyl, phenyl and p-hydoxyphenyl.

17. The compound of claim 1 wherein $R^p$ is selected from the group consisting of hydroxy, methyl, ethyl, hydroxymethyl, hydroxyethyl, phenyl, mono-fluorosubstituted phenyl and mono-chlorosubstituted phenyl.

18. The compound of claim 1 wherein $R^a$ is selected from the group consisting of methyl, ethyl, propyl, ethenyl, propenyl, cyclopropyl, cyclobutyl, phenyl, furanyl, thienyl, pyrrol-1-yl, benzyl, methoxy, ethoxy, propoxy, cyclopropoxy, cyclobutoxy, cyclopentoxy, phenoxy, benzoxy, —SH, -Smethyl, -Sethyl, —S-t-butyl, -Scyclopropyl, -Sphenyl, -Sbenzyl, nitro, cyano, amino, dimethylamino, (cyclohexylmethyl)amino, acetyl, —SCF$_3$, I, F, Cl, Br, trifluoromethyl, —OCF$_3$ and carboxymethyl.

19. The compound of claim 1 wherein there is one $R^a$.

20. The compound of claim 1 wherein there is one $R^a$ positioned on the ring para to the amide substituent.

21. The compound of claim 1 wherein two adjacent $R^a$ are taken together with the carbons of attachment to form a fused ring, the fused ring is phenyl.

22. The compound of claim 1 wherein $R^a$ is selected from the group consisting of nitro, cyano, F, Cl, Br, fused phenyl, I, CF$_3$, methoxy, ethoxy, propoxy, i-propoxy, ethenyl, cyclopentoxy, 2-propenyl, phenyl, furanyl, thienyl, amino, pyrrol-1-yl, dimethylamino, (cyclohexylmethyl)amino, —SCH$_3$, -Sethyl, —S-t-butyl, -Sbenzyl, —SCF$_3$, i-propyl and methyl.

23. The compound of claim 1 wherein $R^b$ is absent or selected from the group consisting of methyl, ethyl, I, F, Cl and Br.

24. The compound of claim 1 wherein $R^b$ is absent.

25. The compound of claim 1 wherein said pharmaceutically acceptable salt is an amino addition salt.

26. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

27. The compound of claim 1 selected from the group consisting of:
(R)-4-Bromo-N-[1-(2,4-dichlorophenyl)-ethyl]-2-(quinoxaline-5-sulfonylamino)-benzamide;
(R)-4-Bromo-N-[1-(2,4-difluoro-phenyl)-ethyl]-2-(quinoxaline-5-sulfonylamino)-benzamide;
(R)-4-Chloro-N-[1-(2,4-difluorophenyl)-ethyl]-2-(quinoxaline-5-sulfonylamino)-benzamide;
(R)-4,5-Dichloro-N-[1-(2,4-difluorophenyl)ethyl]-2-(quinoxaline-5-sulfonylamino)-benzamide;
(R)-4-Chloro-N-[1-(4-fluorophenyl)-ethyl]-2-(quinoxaline-5-sulfonylamino)-benzamide;
(R)-4-Bromo-N-[1-(4-fluorophenyl)-ethyl]-2-(quinoxaline-5-sulfonylamino)-benzamide;
(S)-4-Chloro-N-[1-(2,4-dichlorophenyl)ethyl]-2-(quinoxaline-5-sulfonylamino)-benzamide;
(R)-N-[1-(2,4-Difluorophenyl)-ethyl]-4-iodo-2-(quinoxaline-5-sulfonylamino)-benzamide;
4-Bromo-N-(2-chloro-4-fluoro-benzyl)-2-(quinoxaline-5-sulfonylamino)-benzamide;
4-Bromo-N-(2,4-difluoro-benzyl)-2-(quinoxaline-5-sulfonylamino)-benzamide;
(S)-4-Chloro-N-[1-(2,4-difluoro-phenyl)-2,2,2-trifluoro-ethyl]-2-(quinoxaline-5-sulfonylamino)-benzamide;
(S)-4-Bromo-N-[1-(2,4-difluoro-phenyl)-2,2,2-trifluoro-ethyl]-2-(quinoxaline-5-sulfonylamino)-benzamide;
(R)-4-Bromo-N-methyl-N-(1-phenyl-ethyl)-2-(quinoxaline-5-sulfonylamino)-benzamide;
(R)-4-Iodo-N-methyl-N-(1-phenyl-ethyl)-2-(quinoxaline-5-sulfonylamino)-benzamide;
N-(4-Fluorobenzyl)-4-iodo-N-methyl-2-(quinoxaline-5-sulfonylamino)-benzamide;
(R)-N-[1-(2,4-Difluorophenyl)ethyl]-2-(quinoxaline-5-sulfonylamino)-4-trifluoromethylbenzamide;
(R)-N-[1-(2,4-Dichloro-phenyl)-ethyl]-4-fluoro-2-(quinoxaline-5-sulfonylamino)-benzamide;
(R)-4-Cyano-N-[1-(2,4-difluoro-phenyl)ethyl]-2-(quinoxaline-5-sulfonylamino)-benzamide;
N-Benzyl-4-bromo-N-methyl-2-(quinoxaline-5-sulfonylamino)-benzamide;
N-Benzyl-4-iodo-N-methyl-2-(quinoxaline-5-sulfonylamino)-benzamide;
(R)-4-Chloro-N-[1-(2,4-dichloro-phenyl)-ethyl]-2-(quinoxaline-5-sulfonylamino)-benzamide;
4-Chloro-N-(4-fluoro-benzyl)-N-methyl-2-(quinoxaline-5-sulfonylamino)-benzamide;
4-Bromo-N-(4-fluoro-benzyl)-N-methyl-2-(quinoxaline-5-sulfonylamino)-benzamide;
4-Chloro-N-(4-chloro-benzyl)-N-methyl-2-(quinoxaline-5-sulfonylamino)-benzamide;

4-Bromo-N-(4-chloro-benzyl)-N-methyl-2-(quinoxaline-5-sulfonylamino)-benzamide;
N-(4-Chloro-benzyl)-4-iodo-N-methyl-2-(quinoxaline-5-sulfonylamino)-benzamide;
4-Chloro-N-[1-(4-chloro-phenyl)-ethyl]-2-(quinoxaline-5-sulfonylamino)-benzamide;
4-Bromo-N-[1-(4-chloro-phenyl)-ethyl]-2-(quinoxaline-5-sulfonylamino)-benzamide;
N-[1-(4-Chloro-phenyl)-ethyl]-4-iodo-2-(quinoxaline-5-sulfonylamino)-benzamide;
4-Chloro-N-[1-(4-fluoro-phenyl)-ethyl]-2-(quinoxaline-5-sulfonylamino)-benzamide;
4-Bromo-N-[1-(4-fluoro-phenyl)-ethyl]-2-(quinoxaline-5-sulfonylamino)-benzamide;
N-[1-(4-Fluoro-phenyl)-ethyl]-4-iodo-2-(quinoxaline-5-sulfonylamino)-benzamide;
4-Chloro-N-(2,4-difluoro-benzyl)-2-(quinoxaline-5-sulfonylamino)-benzamide;
N-(2,4-Difluoro-benzyl)-4-iodo-2-(quinoxaline-5-sulfonylamino)-benzamide;
N-(2,4-Difluoro-benzyl)-4-iodo-2-(quinoxaline-5-sulfonylamino)-benzamide;
4-Chloro-N-(2,4-dichloro-benzyl)-2-(quinoxaline-5-sulfonylamino)-benzamide;
4-Bromo-N-(2,4-dichloro-benzyl)-2-(quinoxaline-5-sulfonylamino)-benzamide;
N-(2,4-Dichloro-benzyl)-4-iodo-2-(quinoxaline-5-sulfonylamino)-benzamide;
4-Chloro-N-(2-chloro-4-fluoro-benzyl)-2-(quinoxaline-5-sulfonylamino)-benzamide;
(R)-4-Chloro-N-methyl-N-(1-phenyl-ethyl)-2-(quinoxaline-5-sulfonylamino)-benzamide;
(R)-N-[1-(4-Fluoro-phenyl)-ethyl]-4-iodo-2-(quinoxaline-5-sulfonylamino)-benzamide;
(R)-N-[1-(2,4-Dichloro-phenyl)-ethyl]-4-iodo-2-(quinoxaline-5-sulfonylamino)-benzamide;
(S)-4-Bromo-N-[1-(2,4-dichloro-phenyl)-ethyl]-2-(quinoxaline-5-sulfonylamino)-benzamide;
(S)-N-[1-(2,4-Dichloro-phenyl)-ethyl]-4-iodo-2-(quinoxaline-5-sulfonylamino)-benzamide;
(S)-N-[1-(2,4-Difluoro-phenyl)-2,2,2-trifluoro-ethyl]-4-iodo-2-(quinoxaline-5-sulfonylamino)-benzamide;
(R)-N-[1-(2,4-Dichloro-phenyl)-ethyl]-2-(quinoxaline-5-sulfonylamino)-4-trifluoromethyl-benzamide;
(R)-4-Cyano-N-[1-(2,4-dichloro-phenyl)-ethyl]-2-(quinoxaline-5-sulfonylamino)-benzamide;
(R)-N-[1-(2,4-Difluoro-phenyl)-ethyl]-4-fluoro-2-(quinoxaline-5-sulfonylamino)-benzamide;
(S)-4-Bromo-N-[2-fluoro-1-(4-fluoro-phenyl)-ethyl]-2-(quinoxaline-5-sulfonylamino)-benzamide;
(S)-4-Chloro-N-[2-fluoro-1-(4-fluoro-phenyl)-ethyl]-2-(quinoxaline-5-sulfonylamino)-benzamide;
(S)-N-[2-Fluoro-1-(4-fluoro-phenyl)-ethyl]-4-iodo-2-(quinoxaline-5-sulfonylamino)-benzamide;
4-Bromo-N-[1-(2,4-difluoro-phenyl)-2-fluoro-ethyl]-2-(quinoxaline-5-sulfonylamino)-benzamide;
N-[1-(2,4-Difluoro-phenyl)-2-fluoro-ethyl]-4-iodo-2-(quinoxaline-5-sulfonylamino)-benzamide;
(S)-4-Bromo-N-[1-(2,4-difluoro-phenyl)-2-fluoro-ethyl]-2-(quinoxaline-5-sulfonylamino)-benzamide;
(S)-N-[1-(2,4-Difluoro-phenyl)-2-fluoro-ethyl]-4-iodo-2-(quinoxaline-5-sulfonylamino)-benzamide;
(S)-4-Chloro-N-[1-(2,4-difluoro-phenyl)-2-fluoro-ethyl]-2-(quinoxaline-5-sulfonylamino)-benzamide; and
Quinoxaline-5-sulfonic acid [6-bromo-2-(2,4-difluoro-benzyl)-1,3-dioxo-2,3-dihydro-1H-isoindol-4-yl]-amide.

28. The compound of claim 1 selected from the group consisting of:
Quinoxaline-5-sulfonic acid [5-iodo-2-(piperidine-1-carbonyl)-phenyl]-amide;
Quinoxaline-5-sulfonic acid [5-iodo-2-(morpholine-4-carbonyl)-phenyl]-amide;
Quinoxaline-5-sulfonic acid [5-bromo-2-(1,3,4,5-tetrahydrobenzo[c]azepine-2-carbonyl)phenyl]-amide;
(R)-Quinoxaline-5-sulfonic acid [5-bromo-2-(morpholine-4-carbonyl)-phenyl]-amide;
(R)-Quinoxaline-5-sulfonic acid [5-bromo-2-(3-methyl-morpholine-4-carbonyl)-phenyl]-amide;
(R)-Quinoxaline-5-sulfonic acid [5-chloro-2-(3-methyl-morpholine-4-carbonyl)-phenyl]-amide;
(R)-Quinoxaline-5-sulfonic acid [5-chloro-2-(morpholine-4-carbonyl)phenyl]-amide;
Quinoxaline-5-sulfonic acid [2-(azepane-1-carbonyl)-5-iodophenyl]-amide;
(R)-Quinoxaline-5-sulfonic acid [5-iodo-2-(3-methyl-morpholine-4-carbonyl)-phenyl]-amide;
Quinoxaline-5-sulfonic acid [4,5-dichloro-2-(morpholine-4-carbonyl)-phenyl]-amide;
Quinoxaline-5-sulfonic acid [2-(azepane-1-carbonyl)-5-bromophenyl]-amide;
Quinoxaline-5-sulfonic acid [5-chloro-2-(2,3-dihydro-5H-benzo[f][1,4]oxazepine-4-carbonyl)-phenyl]-amide;
(S)-Quinoxaline-5-sulfonic acid [5-iodo-2-(3-methylmorpholine-4-carbonyl)-phenyl]-amide;
Quinoxaline-5-sulfonic acid [5-bromo-2-(7-fluoro-1,3,4,5-tetrahydro-benzo[c]azepine-2-carbonyl)-phenyl]-amide;
(R,S)-Quinoxaline-5-sulfonic acid [2-(3,5-dimethylmorpholine-4-carbonyl)-5-iodophenyl]-amide;
Quinoxaline-5-sulfonic acid [2-(4-hydroxy-piperidine-1-carbonyl)-5-iodo-phenyl]-amide;
meso-Quinoxaline-5-sulfonic acid [2-(3,5-dimethylmorpholine-4-carbonyl)-5-bromophenyl]-amide;
(S)-Quinoxaline-5-sulfonic acid [5-bromo-2-(3-methyl-morpholine-4-carbonyl)-phenyl]-amide;
Quinoxaline-5-sulfonic acid [2-(4-hydroxy-piperidine-1-carbonyl)-5-bromo-phenyl]-amide;
Quinoxaline-5-sulfonic acid [5-bromo-2-(piperidine-1-carbonyl)-phenyl]-amide;
Quinoxaline-5-sulfonic acid [5-bromo-2-(8-fluoro-2,3-dihydro-5H-benzo[f][1,4]oxazepine-4-carbonyl)phenyl]-amide;
Quinoxaline-5-sulfonic acid [5-chloro-2-(6,8-difluoro-2,3-dihydro-5H-benzo[f][1,4]oxazepine-4-carbonyl)-phenyl]-amide;
Quinoxaline-5-sulfonic acid [5-chloro-2-(piperidine-1-carbonyl)-phenyl]-amide;
Quinoxaline-5-sulfonic acid [5-chloro-2-(1,3,4,5-tetrahydro-benzo[c]azepine-2-carbonyl)-phenyl]-amide;
Quinoxaline-5-sulfonic acid [5-iodo-2-(1,3,4,5-tetrahydro-benzo[c]azepine-2-carbonyl)-phenyl]-amide;
Quinoxaline-5-sulfonic acid [5-bromo-2-(2,3-dihydro-5H-benzo[f][1,4]oxazepine-4-carbonyl)-phenyl]-amide;
Quinoxaline-5-sulfonic acid [2-(2,3-dihydro-5H-benzo[f][1,4]oxazepine-4-carbonyl)-5-iodo-phenyl]-amide;
(S)-Quinoxaline-5-sulfonic acid [5-chloro-2-(3-methyl-morpholine-4-carbonyl)-phenyl]-amide;

meso-Quinoxaline-5-sulfonic acid [5-chloro-2-(3,5-dimethyl-morpholine-4-carbonyl)-phenyl]-amide;

Quinoxaline-5-sulfonic acid [5-chloro-2-(7-fluoro-1,3,4,5-tetrahydro-benzo[c]azepine-2-carbonyl)-phenyl]-amide;

Quinoxaline-5-sulfonic acid [2-(7-fluoro-1,3,4,5-tetrahydro-benzo[c]azepine-2-carbonyl)-5-iodo-phenyl]-amide;

Quinoxaline-5-sulfonic acid [2-(azepane-1-carbonyl)-5-chloro-phenyl]-amide;

Quinoxaline-5-sulfonic acid [5-chloro-2-(8-fluoro-2,3-dihydro-5H-benzo[f][1,4]oxazepine-4-carbonyl)-phenyl]-amide;

Quinoxaline-5-sulfonic acid [2-(8-fluoro-2,3-dihydro-5H-benzo[f][1,4]oxazepine-4-carbonyl)-5-iodo-phenyl]-amide;

Quinoxaline-5-sulfonic acid [2-(piperidine-1-carbonyl)-5-trifluoromethyl-phenyl]-amide;

Quinoxaline-5-sulfonic acid [2-(morpholine-4-carbonyl)-5-trifluoromethyl-phenyl]-amide;

Quinoxaline-5-sulfonic acid [5-bromo-2-(6,8-difluoro-2,3-dihydro-5H-benzo[f][1,4]oxazepine-4-carbonyl)-phenyl]-amide;

Quinoxaline-5-sulfonic acid [2-(6,8-difluoro-2,3-dihydro-5H-benzo[f][1,4]oxazepine-4-carbonyl)-5-iodo-phenyl]-amide; and Quinoxaline-5-sulfonic acid [2-(6,8-difluoro-2,3-dihydro-5H-benzo[f][1,4]oxazepine-4-carbonyl)-5-trifluoromethyl-phenyl]-amide.

29. A pharmaceutical composition comprising a pharmaceutically acceptable carrier and a therapeutically effective amount of a compound of claim 1.

30. A method for the treatment of pancreatic adenocarcinoma, pain, gastro-esophageal reflux disease, gastroduodenal ulcers, reflux esophagitis, anxiety, colon cancer, peptic ulcers, pancreatic tumors, gastric tumors, Barrett's esophagus, antral G cell hyperplasia and Zollinger-Ellison syndrome in mammals comprising the step of administering to a mammal suffering therefrom a therapeutically effective amount of a compound of claim 1.

31. A method for the treatment of pancreatic adenocarcinoma, pain, gastro-esophageal reflux disease, gastroduodenal ulcers, reflux esophagitis, anxiety, colon cancer, peptic ulcers, pancreatic tumors and gastric tumors in mammals comprising the step of administering to a mammal suffering therefrom a therapeutically effective amount of a compound of claim 1.

32. A method for making amidophenyl-sulfonylamino-quinoxalines of claim 1 comprising the steps of reducing compound A6:

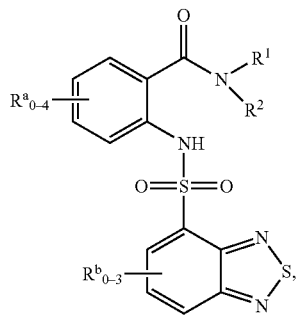

with zinc and acetic acid, and condensing resultant compound A7:

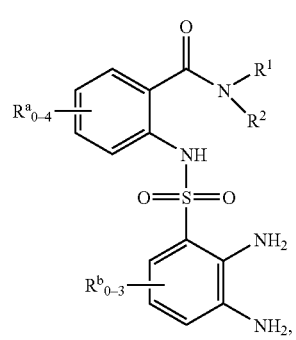

with glyoxal, wherein $R^1$ and $R^2$ are each independently selected from the group consisting of a) H, $C_{1-7}$alkyl, $C_{2-7}$alkenyl, $C_{2-7}$alkynyl, $C_{3-7}$cycloalkyl, $C_{3-7}$cycloalkenyl, benzo-fused$C_{4-7}$cycloalkyl where the point of attachment is a carbon atom adjacent to the ring junction, $C_{3-7}$cycloalkyl$C_{1-7}$alkyl, b) naphthyl-$(CR^s_2)$—, benzoyl$C_{0-3}$alkyl-$(CR^s_2)$—, phenyl, said phenyl optionally fused at two adjacent carbon atoms to $R^f$, phenyl-$(CR^s_2)$—, said phenyl optionally fused at two adjacent carbon atoms to $R^f$, $R^f$ is a linear 3- to 5-membered hydrocarbon moiety optionally mono or di-oxo substituted having 0 or 1 unsaturated bonds, c) $Ar^6$-$(CR^s_2)$—, where $Ar^6$ is a 6-membered heteroaryl having carbon as a point of attachment, having 1 or 2 heteroatom members which are —N═ and optionally benzo fused, d) $Ar^5$—$(CR^s_2)$—, where $Ar^5$ is a 5-membered heteroaryl having carbon as a point of attachment, having 1 heteroatom member selected from the group consisting of O, S, >NH or >N$C_{1-4}$alkyl, having 0 or 1 additional heteroatom member which is —N═ and optionally benzofused, e) $Ar^{6-6}$—$(CR^s_2)$—, where $Ar^{6-6}$ is phenyl having the point of attachment and fused to a 6-membered heteroaryl having 1 or 2 heteroatom members which are —N═, f) $Ar^{6-5}$—$(CR^s_2)$—, where $Ar^{6-5}$ is phenyl having the point of attachment and fused to a 5-membered heteroaryl having 1 heteroatom member selected from the group consisting of O, S, >NH or >N$C_{1-4}$alkyl and having 0 or 1 additional heteroatom member which is —N═, g) $C_{1-4}$alkylO- and HS$C_{1-4}$alkyl, where $R^1$ and $R^2$ are not simultaneously H and, except in positions where $R^s$ is indicated, each of a) to g) is substituted with 0, 1, 2, or 3 of $R^q$, $R^q$ is independently selected from the group consisting of $C_{1-4}$alkyl, hydroxy, fluoro, chloro, bromo, iodo, trifluoromethyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO-$C_{1-4}$alkyl, HS—$C_{1-4}$alkyl, $C_{1-4}$alkylS—$C_{1-4}$alkyl, $C_{1-4}$alkoxy and $C_{1-4}$alkylS-, $R^s$ is independently selected from the group consisting of H, $C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$ alkylaminoC$_{1-4}$alkyl, HO—C$_{1-4}$alkyl, HS—C$_{1-4}$alkyl, C$_{1-4}$alkylO—C$_{1-4}$alkyl, C$_{1-4}$alkylS—C$_{1-4}$alkyl and phenyl;

or, alternatively,

R$^1$ and R$^2$ may be taken together with the nitrogen to which they are attached and are selected from the group consisting of i) 10-oxa-4-aza-tricyclo[5.2.1.0$^{2,6}$]dec-4-yl, optionally mono- or di-substituted with R$^p$, R$^p$ is independently selected from the group consisting of hydroxy, C$_{1-4}$alkyl, hydroxyC$_{1-4}$alkyl, phenyl, mono-, di- or tri-halo substituted phenyl and hydroxyphenyl, ii) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl, optionally having one carbon member which forms a bridge and having 0, 1 or 2 substituents R$^p$, iii) a benzo fused 4-7 membered heterocyclic ring said heterocyclic ring having 0 or 1 additional heteroatom members separated from the nitrogen of attachment by at least one carbon member and selected from O, S, —N═, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents R$^p$, iv) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N═, >NH or >NR$^p$, having 0, 1 or 2 unsaturated bonds, having 0, 1 or 2 carbon members which is a carbonyl and having 0, 1 or 2 substituents R$^p$;

v) 8-oxo-1,5,6,8-tetrahydro-2H,4H-1,5-methano-pyrido[1,2-a][1,5]diazocin-3-yl, optionally having 0, 1 or 2 substituents R$^p$;

R$^a$ is independently selected from the group consisting of C$_{1-6}$alkyl, C$_{2-6}$alkenyl, C$_{3-6}$cycloalkyl, phenyl, furanyl, thienyl, benzyl, pyrrol-1-yl, —OH, —OC$_{1-6}$alkyl, —OC$_{3-6}$cycloalkyl, -Ophenyl, -Obenzyl, —SH, —SC$_{1-6}$alkyl, —SC$_{3-6}$cycloalkyl, -Sphenyl, -Sbenzyl, —CN, —NO$_2$, —N(R$^y$)R$^z$ (wherein R$^y$ and R$^z$ are independently selected from H, C$_{1-4}$alkyl or C$_{1-6}$cycloalkylC$_{1-4}$alkyl), —(C═O)C$_{1-4}$alkyl, —SCF$_3$, halo, —CF$_3$, —OCF$_3$, and —COOC$_{1-4}$alkyl, or, alternatively, two adjacent R$^a$, may be taken together with the carbons of attachment to form a fused ring and selected from the group consisting of phenyl, pyridyl and pyrimidinyl;

or alternatively, R$^2$ and one of R$^a$ can be taken together to be —CH$_2$— or >C═O and to form a fused ring to the phenyl;

R$^b$ is, independently, selected from the group consisting of C$_{1-4}$alkyl and halogen; and enantiomers, diastereomers, hydrates and pharmaceutically acceptable salts, esters and amides thereof.

33. A method for making amidophenyl-sulfonylamino-quinoxalines of claim 1 comprising the steps of sulfonylating compound A5:

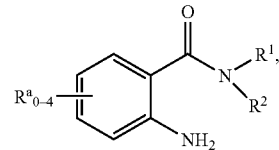

with compound D1:

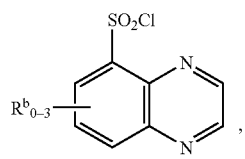

wherein

R$^1$ and R$^2$ are each independently selected from the group consisting of a) H, C$_{1-7}$alkyl, C$_{2-7}$alkenyl, C$_{2-7}$alkynyl, C$_{3-7}$cycloalkyl, C$_{3-7}$cycloalkenyl, benzo-fusedC$_{4-7}$cycloalkyl where the point of attachment is a carbon atom adjacent to the ring junction, C$_{3-7}$cycloalkylC$_{1-7}$alkyl, b) naphthyl-(CR$^s_2$)—, benzoylC$_{0-3}$alkyl-(CR$^s_2$)—, phenyl, said phenyl optionally fused at two adjacent carbon atoms to R$^f$, phenyl-(CR$^s_2$)—, said phenyl optionally fused at two adjacent carbon atoms to R$^f$, R$^f$ is a linear 3- to 5-membered hydrocarbon moiety optionally mono or di-oxo substituted having 0 or 1 unsaturated bonds, c) Ar$^6$—(CR$^s_2$)—, where Ar$^6$ is a 6-membered heteroaryl having carbon as a point of attachment, having 1 or 2 heteroatom members which are —N═ and optionally benzo fused, d) Ar$^5$—(CR$^s_2$)—, where Ar$^5$ is a 5-membered heteroaryl having carbon as a point of attachment, having 1 heteroatom member selected from the group consisting of O, S, >NH or >NC$_{1-4}$alkyl, having 0 or 1 additional heteroatom member which is —N═ and optionally benzofused, e) Ar$^{6-6}$—(CR$^s_2$)—, where Ar$^{6-6}$ is phenyl having the point of attachment and fused to a 6-membered heteroaryl having 1 or 2 heteroatom members which are —N═, f) Ar$^{6-5}$—(CR$^s_2$)—, where Ar$^{6-5}$ is phenyl having the point of attachment and fused to a 5-membered heteroaryl having 1 heteroatom member selected from the group consisting of O, S, >NH or >NC$_{1-4}$alkyl and having 0 or 1 additional heteroatom member which is —N═, g) C$_{1-4}$alkylO- and HSC$_{1-4}$alkyl, where R$^1$ and R$^2$ are not simultaneously H and, except in positions where R$^s$ is indicated, each of a) to g) is substituted with 0, 1, 2, or 3 of R$^q$, R$^q$ is independently selected from the group consisting of C$_{1-4}$alkyl, hydroxy, fluoro, chloro, bromo, iodo, trifluoromethyl, aminoC$_{1-4}$alkyl, C$_{1-4}$alkylaminoC$_{1-4}$alkyl, diC$_{1-4}$alkylaminoC$_{1-4}$alkyl, HO—C$_{1-4}$alkyl, $C_{1-4}$alkylO-$C_{1-4}$alkyl, HS—$C_{1-4}$alkyl, $C_{1-4}$alkylS-$C_{1-4}$alkyl, $C_{1-4}$alkoxy and $C_{1-4}$alkylS-, $R^s$ is independently selected from the group consisting of H, $C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, HS—$C_{1-4}$alkyl, $C_{1-4}$alkylO-$C_{1-4}$alkyl, $C_{1-4}$alkylS-$C_{1-4}$alkyl and phenyl;

or, alternatively, $R^1$ and $R^2$ may be taken together with the nitrogen to which they are attached and are selected from the group consisting of i) 10-oxa-4-aza-tricyclo[5.2.1.0$^{2,6}$]dec-4-yl, optionally mono- or di-substituted with $R^p$, $R^p$ is independently selected from the group consisting of hydroxy, $C_{1-4}$alkyl, hydroxy$C_{1-4}$alkyl, phenyl, mono-, di- or tri-halo substituted phenyl and hydroxyphenyl, ii) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl, optionally having one carbon member which forms a bridge and having 0, 1 or 2 substituents $R^p$, iii) a benzo fused 4-7 membered heterocyclic ring said heterocyclic ring having 0 or 1 additional heteroatom members separated from the nitrogen of attachment by at least one carbon member and selected from O, S, —N═, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents $R^p$, iv) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N═, >NH or >NR$^p$, having 0, 1 or 2 unsaturated bonds, having 0, 1 or 2 carbon members which is a carbonyl and having 0, 1 or 2 substituents $R^p$;

v) 8-oxo-1,5,6,8-tetrahydro-2H,4H-1,5-methano-pyrido[1,2-a][1,5]diazocin-3-yl, optionally having 0, 1 or 2 substituents $R^p$;

$R^a$ is independently selected from the group consisting of $C_{1-6}$alkyl, $C_{2-6}$alkenyl, $C_{3-6}$cycloalkyl, phenyl, furanyl, thienyl, benzyl, pyrrol-1-yl, —OH, —O$C_{1-6}$alkyl, —O$C_{3-6}$cycloalkyl, -Ophenyl, -Obenzyl —SH, —S$C_{1-6}$alkyl, —S$C_{3-6}$cycloalkyl, -Sphenyl, -Sbenzyl, —N, —NO$_2$, —N(R$^y$)R$^z$ (wherein R$^y$ and R$^z$ are independently selected from H, $C_{1-4}$alkyl or $C_{1-6}$cycloalkyl$C_{1-4}$alkyl), —(C═O)$C_{1-4}$alkyl, —SCF$_3$, halo, —CF$_3$, —OCF$_3$, and —COO$C_{1-4}$alkyl, or, alternatively, two adjacent $R^a$, may be taken together with the carbons of attachment to form a fused ring and selected from the group consisting of phenyl, pyridyl and pyrimidinyl;

or alternatively, $R^2$ and one of $R^a$ can be taken together to be —CH$_2$— or >C═O and to form a fused ring to the phenyl;

$R^b$ is, independently, selected from the group consisting of $C_{1-4}$alkyl and halogen;

and enantiomers, diastereomers, hydrates, and pharmaceutically acceptable salts, esters and amides thereof.

34. A method for making amidophenyl-sulfonylamino-quinoxalines of claim 1 comprising the step of peptide coupling compound C3:

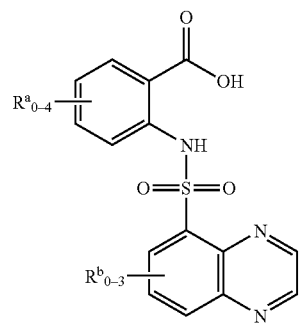

with an amine of the formula $R^1R^2NH$, wherein $R^1$ and $R^2$ are as defined above, wherein $R^a$ is independently selected from the group consisting of $C_{1-6}$alkyl, $C_{2-6}$alkenyl, $C_{3-6}$cycloalkyl, phenyl, furanyl, thienyl, benzyl, pyrrol-1-yl, —OH, —O$C_{1-6}$alkyl, —O$C_{3-6}$cycloalkyl, -Ophenyl, -Obenzyl —SH, —S$C_{1-6}$alkyl, —S$C_{3-6}$cycloalkyl, -Sphenyl, -Sbenzyl, —CN, —NO$_2$, —N(R$^y$)R$^z$ (wherein R$^y$ and R$^z$ are independently selected from H, $C_{1-4}$alkyl or $C_{1-6}$cycloalkyl$C_{1-4}$alkyl), —(C═O)$C_{1-4}$alkyl, —SCF$_3$, halo, —CF$_3$, —OCF$_3$, and —COO$C_{1-4}$alkyl, or, alternatively, two adjacent $R^a$, may be taken together with the carbons of attachment to form a fused ring and selected from the group consisting of phenyl, pyridyl and pyrimidinyl;

or alternatively, $R^2$ and one of $R^a$ can be taken together to be —CH$_2$— or >C═O and to form a fused ring to the phenyl;

$R^b$ is, independently, selected from the group consisting of $C_{1-4}$alkyl and halogen;

and enantiomers, diastereomers, hydrates, and pharmaceutically acceptable salts, esters and amides thereof.

35. The method of claim 34, which comprises the initial steps of reducing compound B3:

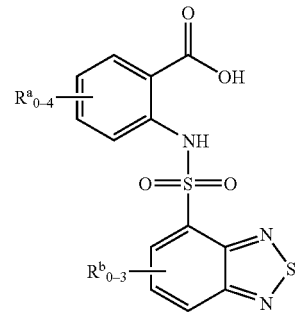

with zinc and acetic acid, and condensing resultant compound B4:

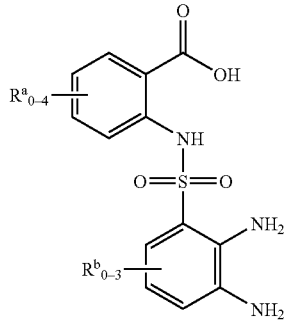

with glyoxal, to produce compound C3.

36. A method for making amidophenyl-sulfonylaminoquinoxalines of claim 1 comprising the steps of sulfonylating compound C1:

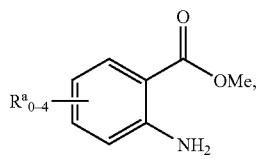

with compound D1:

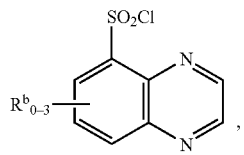

to produce a compound C2:

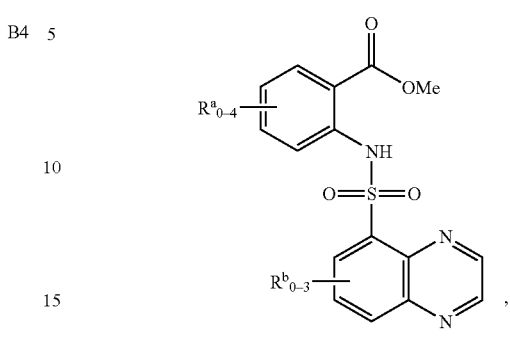

wherein $R^a$ is independently selected from the group consisting of $C_{1-6}$alkyl, $C_{2-6}$alkenyl, $C_{3-6}$cycloalkyl, phenyl, furanyl, thienyl, benzyl, pyrrol-1-yl, —OH, —OC$_{1-6}$alkyl, —OC$_{3-6}$cycloalkyl, -Ophenyl, -Obenzyl —SH, —SC$_{1-6}$alkyl, —SC$_{3-6}$cycloalkyl, -Sphenyl, -Sbenzyl, —CN, —NO$_2$, —N(R$^y$)R$^z$ (wherein R$^y$ and R$^z$ are independently selected from H, $C_{1-4}$alkyl or $C_{1-6}$cycloalkylC$_{1-4}$), —(C=O)C$_{1-4}$alkyl, —SCF$_3$, halo, —CF$_3$, —OCF$_3$, and —COOC$_{1-4}$alkyl, or, alternatively, two adjacent $R^a$, may be taken together with the carbons of attachment to form a fused ring and selected from the group consisting of phenyl, pyridyl and pyrimidinyl;

or alternatively, $R^2$ and one of $R^a$ can be taken together to be —CH$_2$— or >C=O and to form a fused ring to the phenyl;

$R^b$ is, independently, selected from the group consisting of $C_{1-4}$alkyl and halogen;

and enantiomers, diastereomers, hydrates, and pharmaceutically acceptable salts, esters and amides thereof.

* * * * *